(12) United States Patent
Crockett et al.

(10) Patent No.: US 10,448,963 B2
(45) Date of Patent: Oct. 22, 2019

(54) DEVICES, SYSTEMS AND METHODS FOR TISSUE REPAIR

(75) Inventors: Heber Crockett, Kearney, NE (US);
John Wright, Kearney, NE (US);
James G. Whayne, Chapel Hill, NC (US); Kevin L. Ohashi, Jamaica Plain, MA (US); Sidney D. Fleischman, Durham, NC (US)

(73) Assignee: Bay Innovation Group, LLC, Mountain View, CA (US)

( * ) Notice: Subject to any disclaimer, the term of this patent is extended or adjusted under 35 U.S.C. 154(b) by 0 days.

(21) Appl. No.: 13/184,310

(22) Filed: Jul. 15, 2011

(65) Prior Publication Data
US 2012/0158020 A1    Jun. 21, 2012

Related U.S. Application Data

(60) Continuation of application No. 12/621,872, filed on Nov. 19, 2009, now abandoned, which is a division of
(Continued)

(51) Int. Cl.
*A61B 17/29* (2006.01)
*A61B 17/00* (2006.01)
(Continued)

(52) U.S. Cl.
CPC ........ *A61B 17/29* (2013.01); *A61B 17/00234* (2013.01); *A61B 17/0469* (2013.01);
(Continued)

(58) Field of Classification Search
CPC ...... A61B 17/1285; A61B 2017/00827; A61B 2017/0488; A61B 2017/0409; A61B 17/29
(Continued)

(56) References Cited

U.S. PATENT DOCUMENTS

| 4,957,498 A | 9/1990 | Caspari et al. |
| 5,015,249 A | 5/1991 | Nakao et al. |
| (Continued) | | |

FOREIGN PATENT DOCUMENTS

| WO | WO 1996/027331 | 9/1996 |
| WO | WO 1999/003402 | 1/1999 |
| (Continued) | | |

OTHER PUBLICATIONS

Bradley, et al. "Arthroscopic Treatment of Multidirectional Instability: Thermal Technique", Shoulder Arthroscopy, edited by Tibone et al., Aug. 2003.
(Continued)

*Primary Examiner* — Thomas M McEvoy
(74) *Attorney, Agent, or Firm* — Levine Bagade Han LLP

(57) ABSTRACT

Devices, systems and methods are disclosed for repairing soft tissue. The surgical system allows for the creation of tissue repair by grasping, aligning and sewing or fixing tissue. For example, this system may be used for clipping together excessive capsular tissue and reducing the overall capsular volume. The deployment device includes a central grasping mechanism and an outer clip delivery system. The clip embodiments may be single or multi-component (penetration and locking base components) that penetrate tissue layers and deploy or lock to clip the tissue together. An example of the system is used to reduce the joint capsule tissue laxity and reduces the potential for subluxation or dislocation of the joint by either restricting inferior laxity (anterior or posterior) and resolving or eliminating pathologic anterior or posterior translation.

10 Claims, 57 Drawing Sheets

Related U.S. Application Data application No. 11/045,209, filed on Jan. 31, 2005, now abandoned.

(60) Provisional application No. 60/584,585, filed on Jul. 1, 2004, provisional application No. 60/570,627, filed on May 13, 2004.

(51) Int. Cl.
*A61B 17/04* (2006.01)
*A61B 17/064* (2006.01)
*A61B 17/08* (2006.01)
*A61B 17/128* (2006.01)
*A61B 17/068* (2006.01)
*A61B 17/06* (2006.01)
*A61B 17/30* (2006.01)
*A61F 2/08* (2006.01)

(52) U.S. Cl.
CPC ........ *A61B 17/0643* (2013.01); *A61B 17/083* (2013.01); *A61B 17/1285* (2013.01); *A61B 17/0682* (2013.01); *A61B 2017/00004* (2013.01); *A61B 2017/00243* (2013.01); *A61B 2017/00349* (2013.01); *A61B 2017/00827* (2013.01); *A61B 2017/00867* (2013.01); *A61B 2017/0419* (2013.01); *A61B 2017/0454* (2013.01); *A61B 2017/0458* (2013.01); *A61B 2017/0464* (2013.01); *A61B 2017/0618* (2013.01); *A61B 2017/0647* (2013.01); *A61B 2017/2901* (2013.01); *A61B 2017/306* (2013.01); *A61F 2/0811* (2013.01)

(58) Field of Classification Search
USPC ........ 606/213, 219, 139, 142, 144, 148, 150
See application file for complete search history.

(56) References Cited

U.S. PATENT DOCUMENTS

| | | | |
|---|---|---|---|
| 5,085,661 A | 2/1992 | Moss | |
| 5,188,636 A | 2/1993 | Fedotov | |
| 5,254,126 A | 10/1993 | Filipi et al. | |
| 5,281,237 A | 1/1994 | Gimpelson | |
| 5,336,231 A | 8/1994 | Adair | |
| 5,403,326 A | 4/1995 | Harrison et al. | |
| 5,431,666 A | 7/1995 | Sauer et al. | |
| 5,439,467 A | 8/1995 | Benderev et al. | |
| 5,674,230 A * | 10/1997 | Tovey et al. | 606/139 |
| 6,494,888 B1 | 12/2002 | Laufer et al. | |
| 6,533,795 B1 | 3/2003 | Tran et al. | |
| 6,551,330 B1 | 4/2003 | Bain et al. | |
| 6,770,084 B1 | 8/2004 | Bain et al. | |
| 6,921,361 B2 | 7/2005 | Suzuki et al. | |
| 7,063,715 B2 | 6/2006 | Onuki et al. | |
| 7,510,559 B2 | 3/2009 | Deem et al. | |
| 2002/0095199 A1 | 7/2002 | West et al. | |
| 2002/0120188 A1 | 8/2002 | Brock et al. | |
| 2002/0128533 A1 | 9/2002 | Barker | |
| 2003/0078599 A1 | 4/2003 | O'Quinn et al. | |
| 2003/0083695 A1 | 5/2003 | Morris et al. | |
| 2003/0236535 A1 | 12/2003 | Onuki et al. | |
| 2004/0034371 A1 | 2/2004 | Lehman et al. | |
| 2004/0059352 A1 | 3/2004 | Burbank et al. | |
| 2004/0092968 A1 | 5/2004 | Caro et al. | |
| 2004/0260314 A1 | 12/2004 | Lizardi et al. | |
| 2008/0077162 A1 | 3/2008 | Domingo | |
| 2008/0140118 A1 | 6/2008 | Martinek | |

FOREIGN PATENT DOCUMENTS

| | | |
|---|---|---|
| WO | WO 2000/018320 | 4/2000 |
| WO | WO 2001/089370 | 11/2001 |
| WO | WO 2006/007576 | 1/2006 |
| WO | WO 2008/113076 | 9/2008 |
| WO | WO 2009/005527 | 1/2009 |

OTHER PUBLICATIONS

Tibone, et al. "Surgical Technique," *Shoulder Arthroscopy*, pp. 116-119, Springer-Verlag, New York, Inc., 2003.

PCT International Patent Application No. PCT/US2005/0 23619 filed Jul. 1, 2005, International Search Report dated Aug. 3, 2007.

U.S. Appl. No. 12/621,872, filed Nov. 19, 2009 in the name of Crocket et al., Non-final Office Action dated Jan. 21, 2011.

* cited by examiner

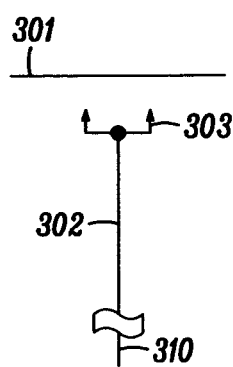
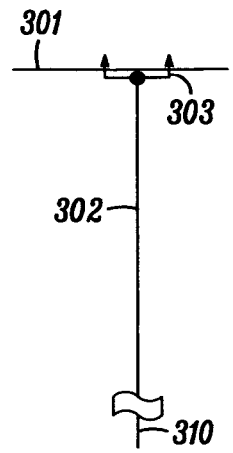
*FIG. 3A*  *FIG. 3B*
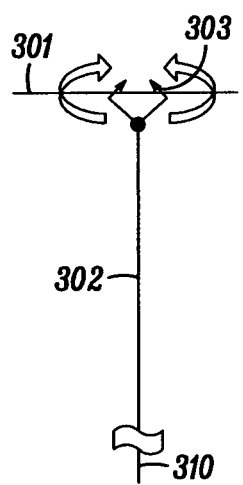
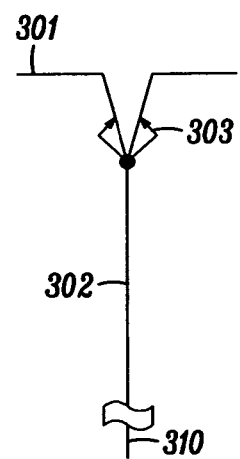
*FIG. 3C*  *FIG. 3D*

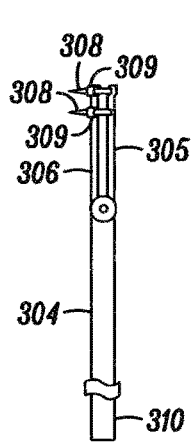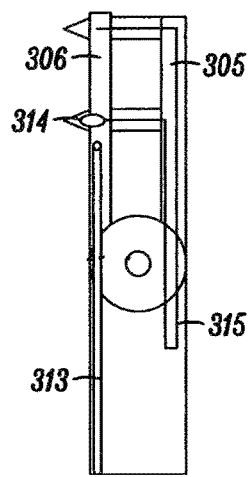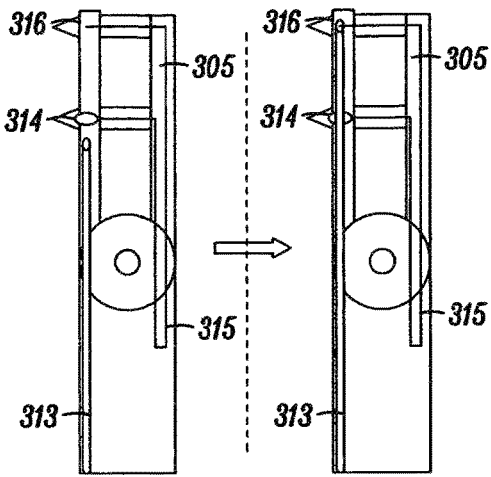
FIG. 5A                    FIG. 5B
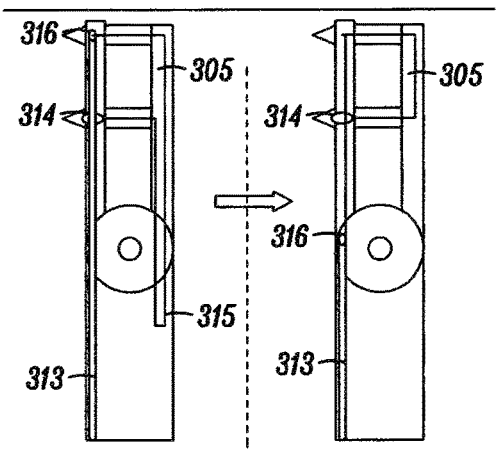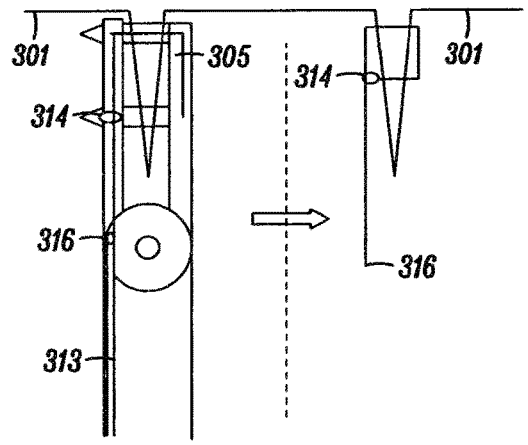
FIG. 5C                    FIG. 5D
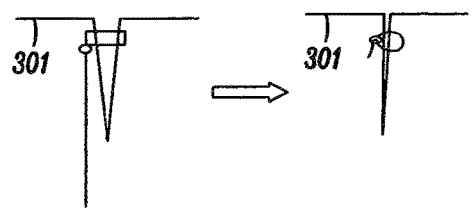
FIG. 5E

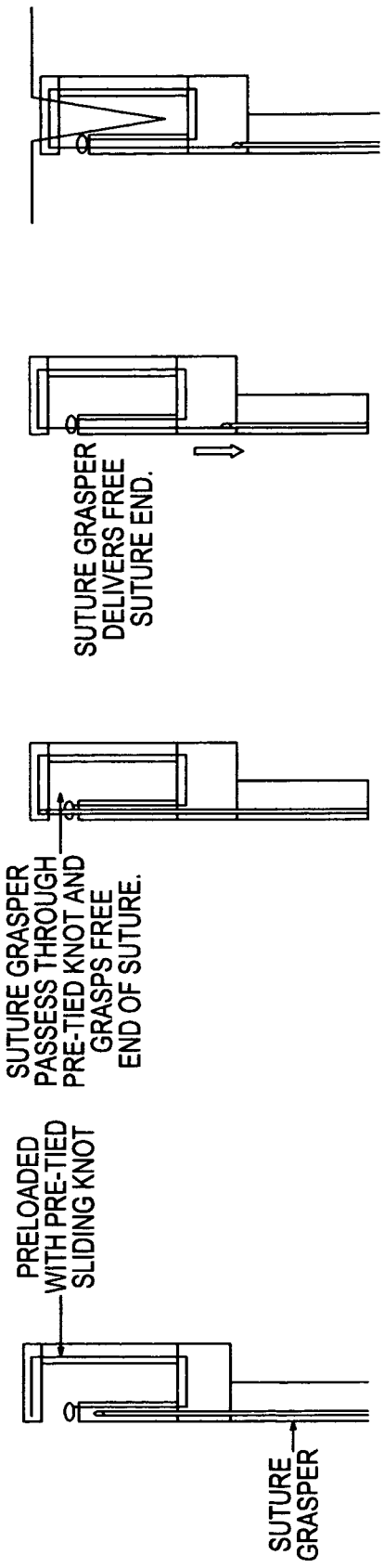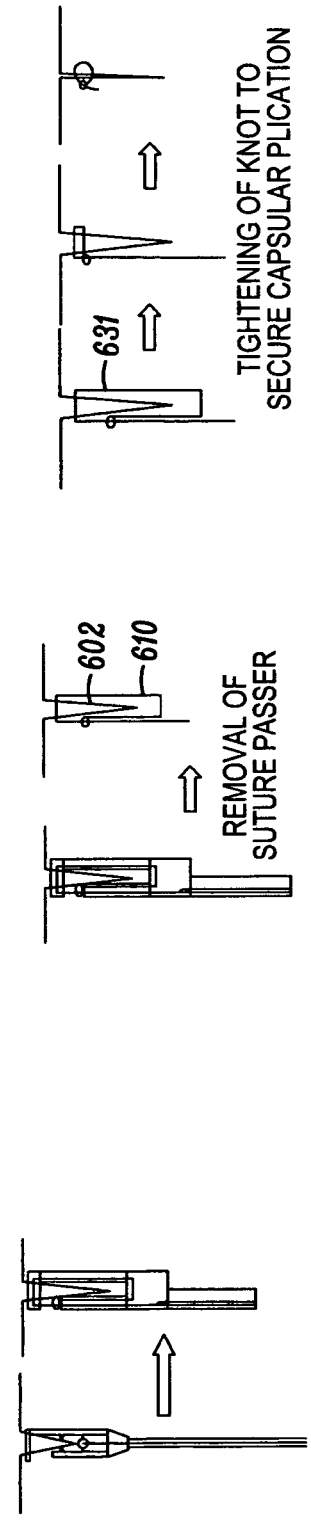

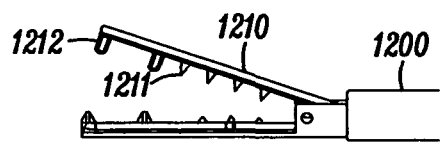 
FIG. 12A     FIG. 12B
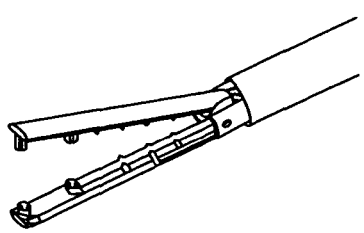
FIG. 12C
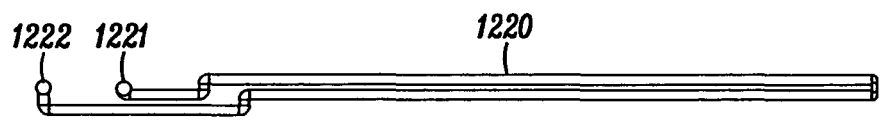
FIG. 12D
FIG. 12E

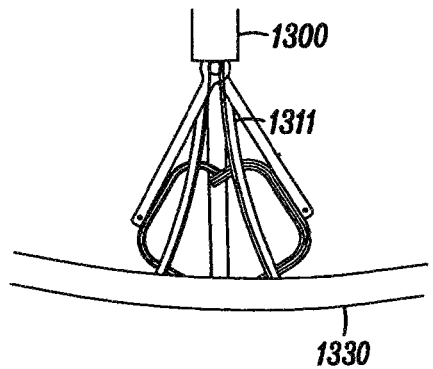
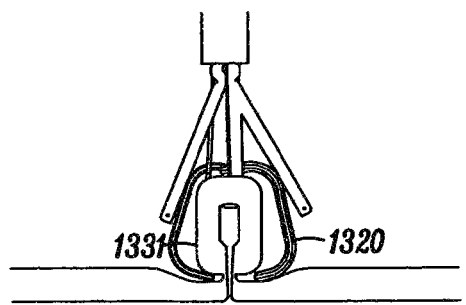
*FIG. 13A*  *FIG. 13B*
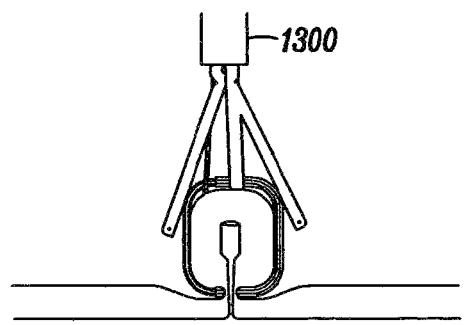
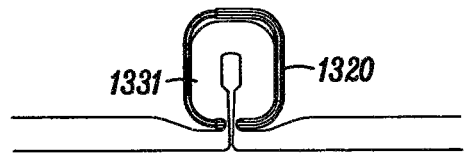
*FIG. 13C*  *FIG. 13D*

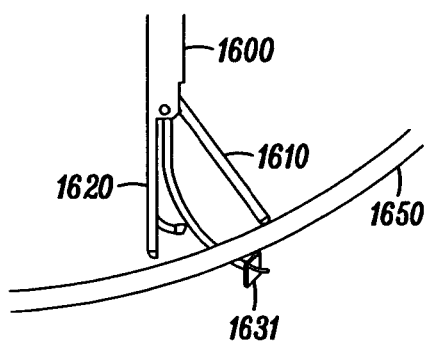
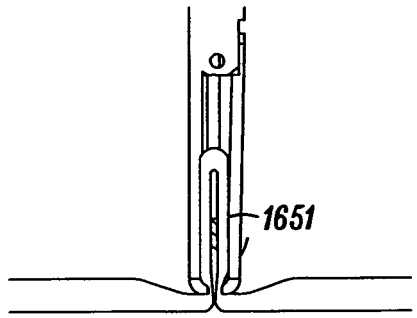
FIG. 17A FIG. 17B
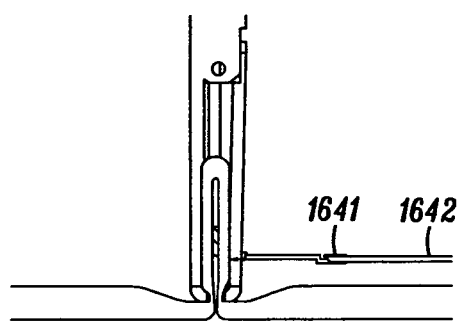
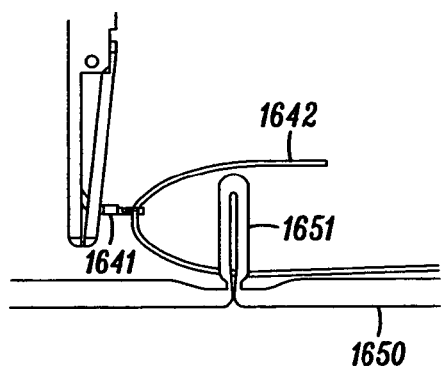
FIG. 17C FIG. 17D

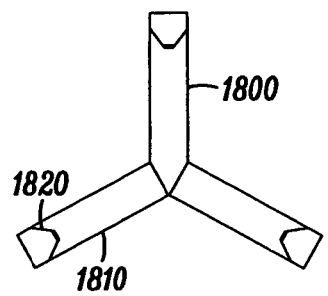
FIG. 18A  FIG. 18B
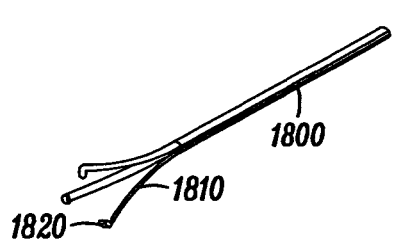
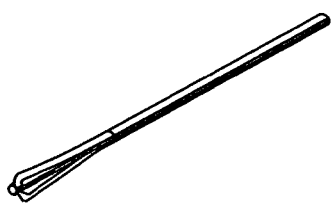
FIG. 18C  FIG. 18D

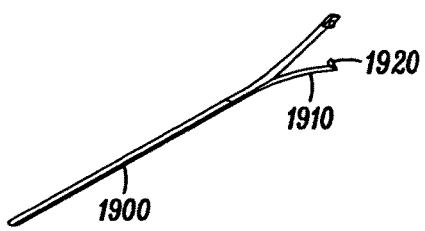
FIG. 19A     FIG. 19B
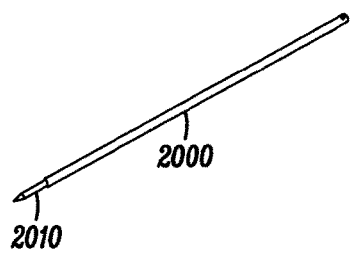
FIG. 20A     FIG. 20B

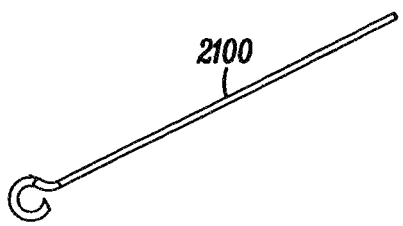 
*FIG. 21A*  *FIG. 21B*
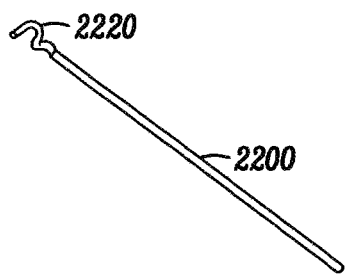 
*FIG. 22A*  *FIG. 22B*

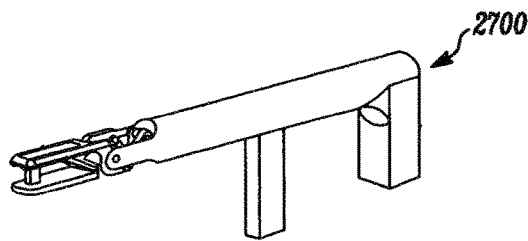 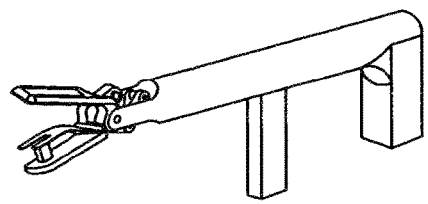
FIG. 27A  FIG. 27B
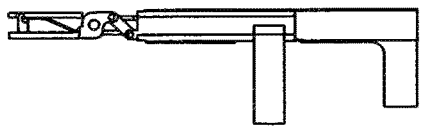 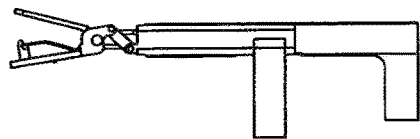
FIG. 27C  FIG. 27D
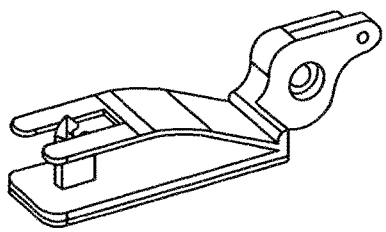 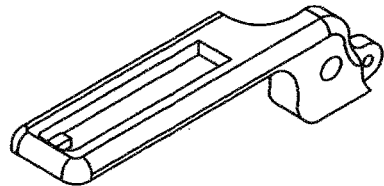
FIG. 27E  FIG. 27F

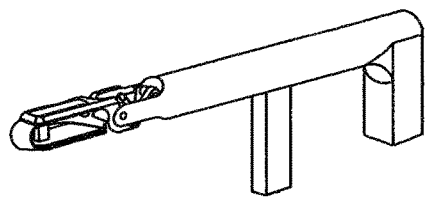
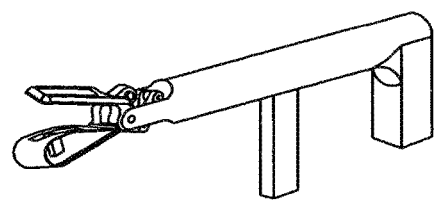
FIG. 28A                FIG. 28B
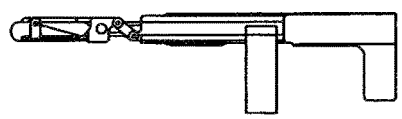
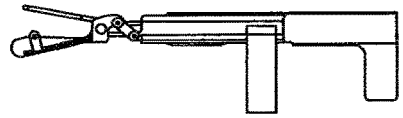
FIG. 28C                FIG. 28D

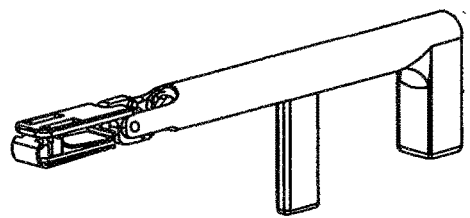
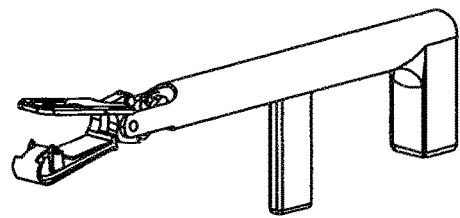
FIG. 30A  FIG. 30B
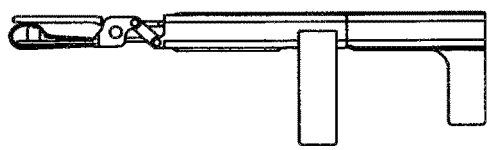
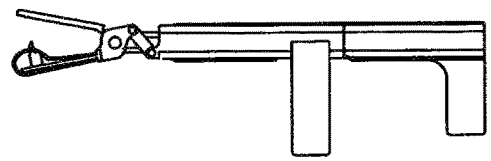
FIG. 30C  FIG. 30D
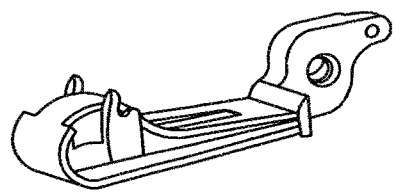
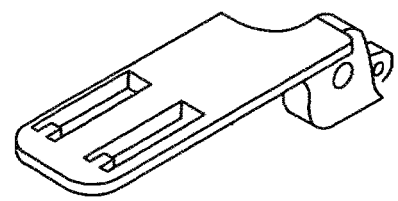
FIG. 30E  FIG. 30F

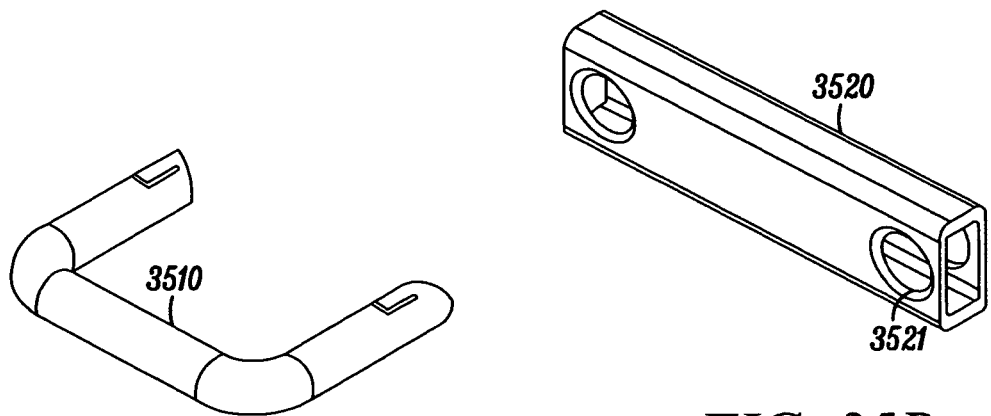
FIG. 35A
FIG. 35B
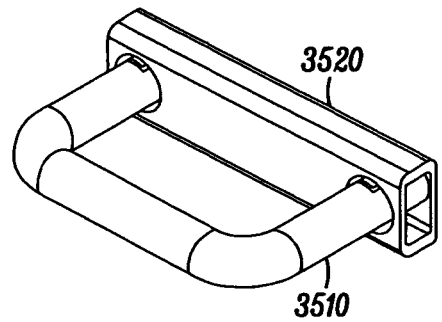
FIG. 35C

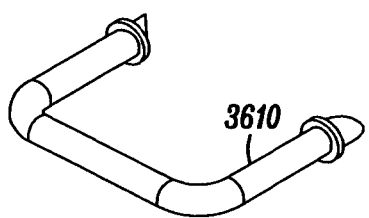 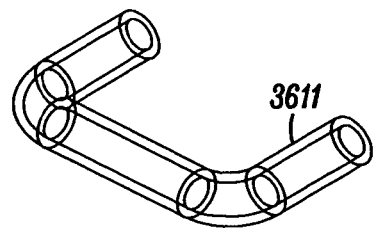
FIG. 36A  FIG. 36B
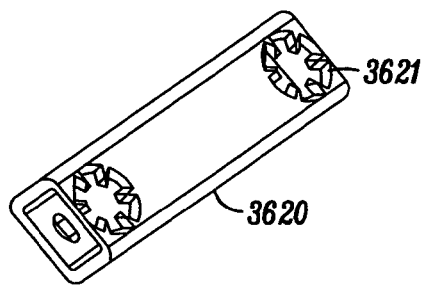 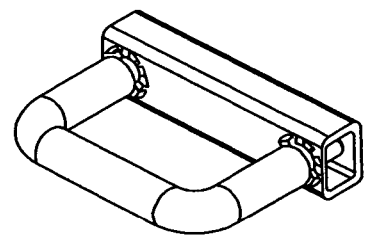
FIG. 36C  FIG. 36D
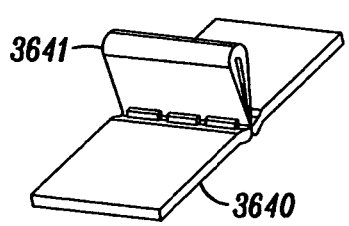 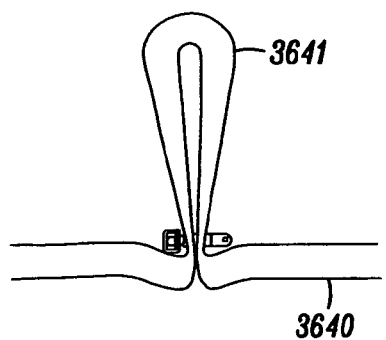
FIG. 36E  FIG. 36F

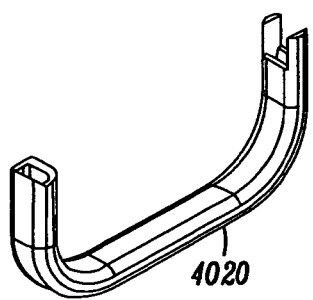
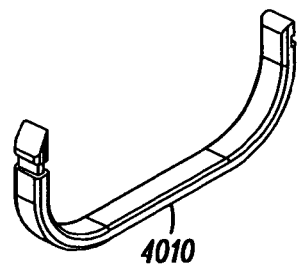
*FIG. 40A*     *FIG. 40B*
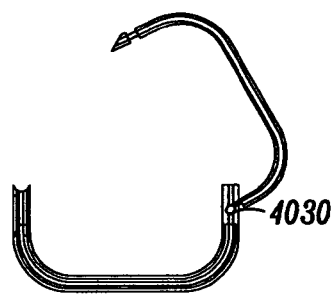
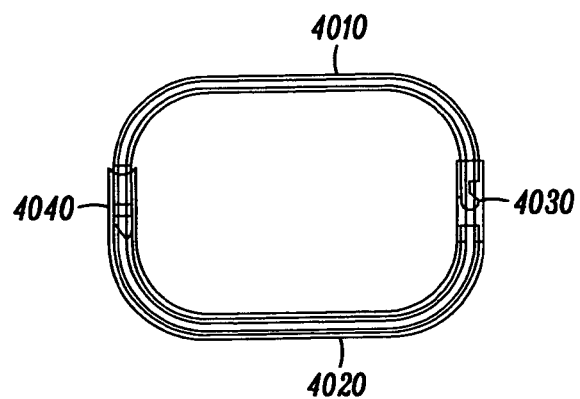
*FIG. 40C*     *FIG. 40D*

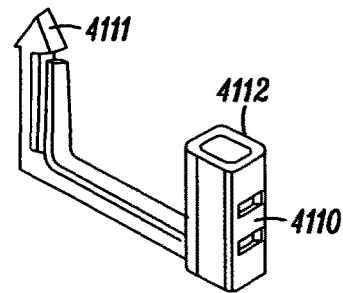
FIG. 41A              FIG. 41B
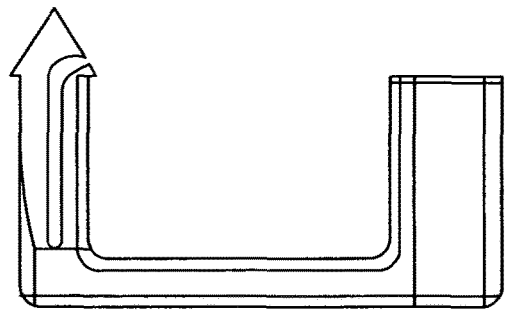
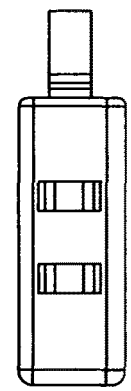
FIG. 41C              FIG. 41D
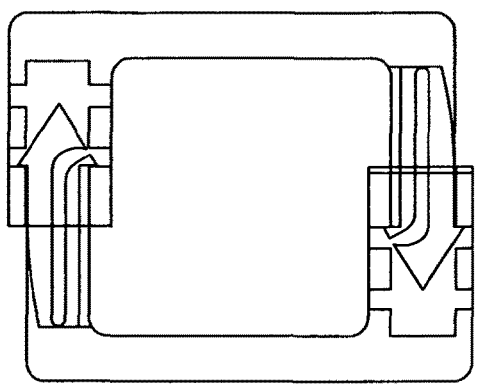
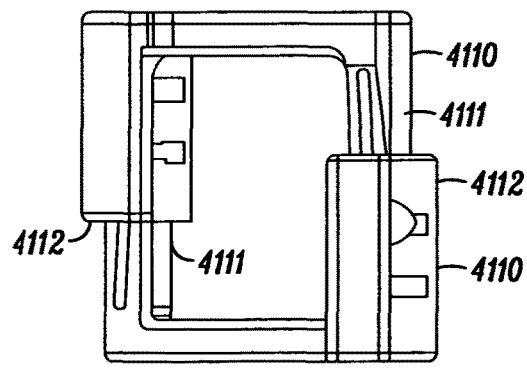
FIG. 41E              FIG. 41F

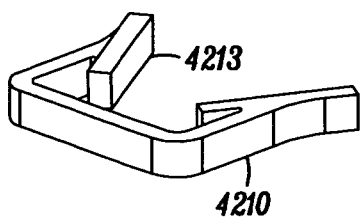
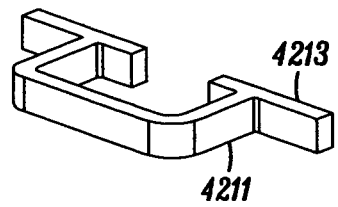
FIG. 42A    FIG. 42B
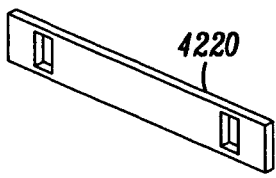
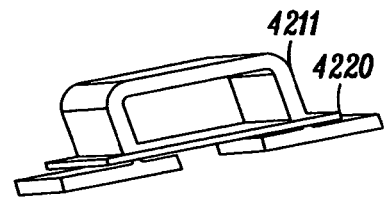
FIG. 42C    FIG. 42D
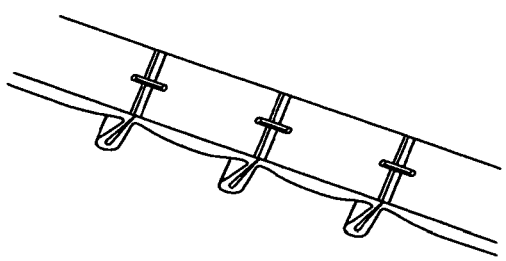
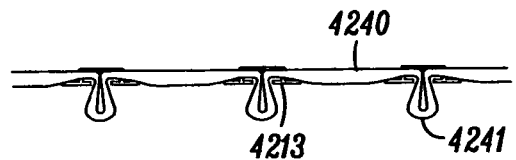
FIG. 42E    FIG. 42F

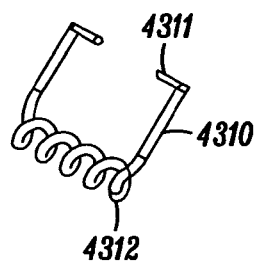
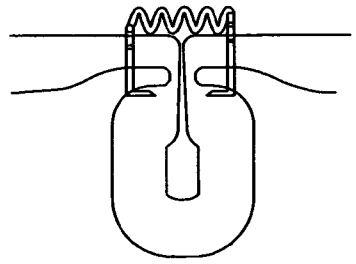
FIG. 43A　　　　FIG. 43B
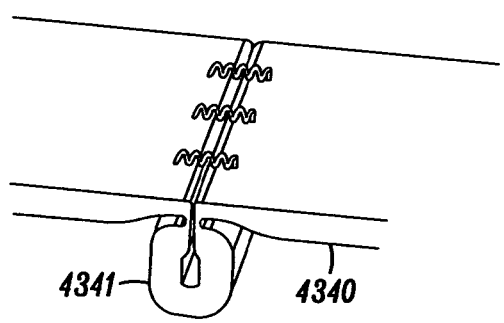
FIG. 43C

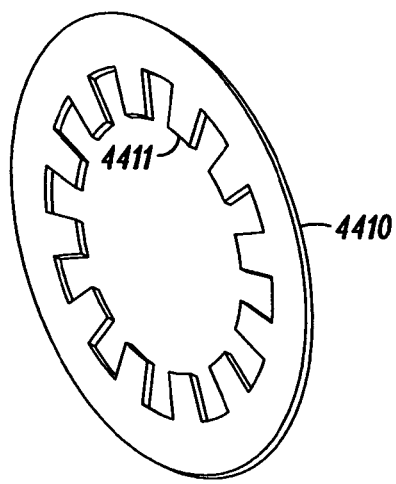 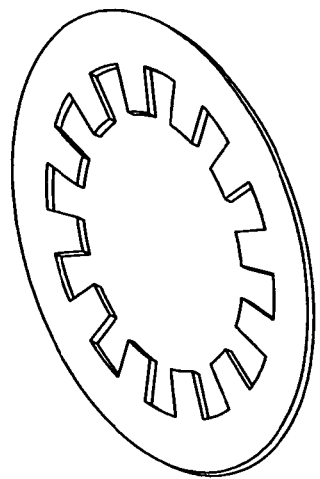
FIG. 44A  FIG. 44B
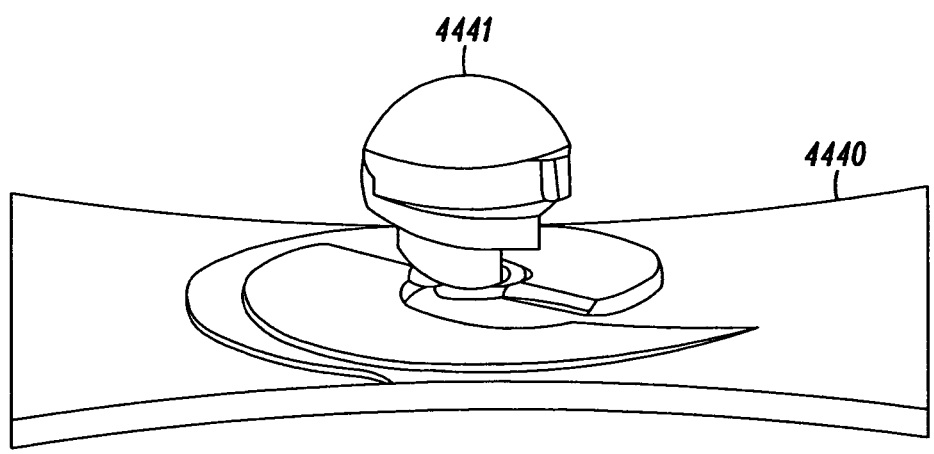
FIG. 44C

DEVICES, SYSTEMS AND METHODS FOR TISSUE REPAIR

CROSS-REFERENCE TO RELATED APPLICATIONS

This application is a continuation of Ser. No. 12/621,872 filed Nov. 19, 2009, which is a divisional of U.S. patent application Ser. No. 11/045,209, filed on Jan. 31, 2005, which claims the benefit of priority of U.S. Provisional Application No. 60/584,585 filed on Jul. 1, 2004 and U.S. Provisional Application No. 60/570,627 filed on May 13, 2004, the content of which is incorporated herein by reference in its entirety.

FIELD OF INVENTION

The present invention relates generally to devices, systems and methods for tissue repair. More particularly, the present invention relates to devices, systems and methods for treating unidirectional and multidirectional instability of tissue structures.

BACKGROUND OF THE INVENTION

Tissue instability or compromise is a common occurrence in all persons, whether induced by age, repeated use, disease, accident or natural and abnormal formation. Such instability may include, for example, intentional or accidental tears, cuts, stretching, loosening, deterioration of structure, loss of firmness, and the like. Furthermore, such tissue may relate to orthopedics, as in the skeletal system and its associated muscles, joints and ligaments and the like, or non-orthopedic systems, such as smooth muscles, gastrointestinal, cardiac, pulmonary, neural, dermal, ocular and the like.

No matter what type of instability is present or whether the tissue to be repaired is classified as orthopedic or non-orthopedic, similar issues and objectives are encountered by the surgeon, namely, creating a stable and reliable structure and doing so in as easy and reliable manner as possible. For example, a neurosurgeon aims to create a stable and reliable adhesion of two neural tissue structures, while at the same time creating minimal damage. The neurosurgeon desires a technique that is minimally invasive, highly reproducible and reliable, and highly effective in connecting the tissue to itself or other similar or dissimilar tissue. It would be even more beneficial to somehow have the tissue become induced to adhere to itself or the other tissue.

In another similar example, in orthopedics soft tissue surgery, the surgeon desires to repair the damaged or diseased tissue in such a manner such that the tissue binds with itself or other tissue in a firm but minimally damaging manner. In muscle or ligament repair, for example, it is necessary to suture the tissue together to promote strength and unity in the structure while at the same time, allow for natural movement to occur.

More broadly, traditional soft tissue repair is a common procedure that typically involves some form of conventional suturing or stapling. For example, certain joints, such as hips, knees, shoulders and elbows contain tissues that are common sources of problems, whether natural or induced, that require extensive physical therapy or surgery to correct. There are similarities between such examples of tissues that present a uniform set of issues for the health care worker such that a treatment of one type of tissue will be in many ways similar to the treatment of another type of tissue, even though the shape, properties and architecture of each tissue is uniquely different. Of such tissues or tissue structures, a common source of medical problems occurs in the joints. Although the below example will be described with respect to the shoulder joint as an example, similar problems are inherent in other soft tissue areas and one having ordinary skill in the art would be cognizant of such problems and how to apply the principles of the present invention to address the problems in such other tissues or tissue systems.

Joint instability is a complex clinical problem associated with a variety of treatment options that include the use of arthroscopic and open surgical methods. For example, for the shoulder joint, open surgical methods for producing a capsular shift to increase the capsular ligament tension and improving the joint stability have been demonstrated. However, adequate arthroscopic methods that approximate the clinical outcome achieved by open surgical methods for reducing excessive joint laxity have been slow to develop or have begun to show less than optimal long term clinical outcomes (e.g., thermal methods).

The shoulder joint, in particular, has inherent instability because of its large range and motion combined with the relatively shallow joint bony socket (glenoid). Anatomically, the rotator cuff acts as the primary dynamic joint stabilizer, while the inferior glenohumeral ligament acts as the primary static shoulder joint stabilizer. Damage to or laxity of one of these stabilizing structures can result in the presentation of clinically relevant shoulder instability.

The onset of shoulder instability is generally associated with a traumatic injury, an atraumatic motion injury, or chronic overuse of the shoulder. Most typically, the instability of the shoulder stems from disruption and/or looseness (excessive capsule laxity) of the shoulder capsule. The resulting subluxation or dislocation of the joint can be painful and debilitating for the individual. The overall approach of shoulder stabilization surgery is to first repair the disrupted/torn capsule and second to tighten the loose capsule ligaments. Of note there are instances where the capsule is intact (e.g., no tear) and only tightening of the capsule ligaments is required to restore joint stability. The ultimate goals of shoulder stabilization include restoring appropriate capsule tension, limiting of humeral head translation, and excessively decreasing range of motion.

Up to 98% of all shoulder joint dislocations occur in the anterior direction, 95% of which are first time dislocations. Over 70% of these individuals will have recurrent instability (subluxation or dislocation) within two years after the first event, potentially requiring surgical intervention.

Certain conventional devices serve to assist with repair of the shoulder capsule when it is disrupted, such as in the case of Bankart Lesions. It is noted that Bankart Lesions are identified by the characteristic stripping/tearing of the anterior inferior labrum from the glenoid. Treatment of these lesions is typically accomplished through a standard open incision or with existing arthroscopic technology.

Clinically described excessive joint laxity in the joint capsule can range from 1.0 to more than 20.0 mm in ligament elongation, resulting in recurrent glenohumeral subluxation or dislocation. A loose shoulder capsule may be tightened readily when a standard open incision is used, but tightening the shoulder capsule arthroscopically poses significant challenges with existing instruments. For example, the acute angles at which the surgical devices are able to approximate the soft tissue and identify regions where suturing would be desirable are limiting. Furthermore, the ability to pass a suture and tie snug surgical knots that compress the tissue in the desired plane with a reasonable suture time is difficult if not cumbersome. Finally, the ability to dictate the level of tissue tied is limited to the tissue needle bite size and remains difficult for the surgeon to reproducibly specify the level of tissue compression desired.

A recently introduced technology, thermal capsulorrhaphy, initially held significant promise as a means of facilitating and expediting arthroscopic shoulder capsule tightening. The premise of this technique is to manipulate the characteristics of the approximately 90% Type I collagen structure of ligaments by thermal exposure. It has been demonstrated that at temperatures above 65 degrees Celsius, collagen begins to denature (e.g., unwinding of the helical structure), resulting in tissue shrinkage. Collagen shrinkage of up to 50% has been demonstrated using thermal energy. However, this technology has yielded equivocal results and progressive skepticism from shoulder surgeons. Specifically, concerns related to long term clinical outcomes for shoulder instability with altered capsular structure have been noted. There is a strong current sentiment among shoulder surgeons that tightening the shoulder capsule by plication with sutures will prove to be more efficacious and more reproducible than the use of thermal mechanisms to reduce the ligament laxity in the capsule.

Additional concerns of thermal capsulorrhaphy application include potential injury to the axillary nerve, bleeding, pain, and excessive swelling of the capsule. More importantly, the technical methods used during thermal capsulorrhaphy do not allow the surgeon to control the level of plication that is desired or anticipated. Specifically, thermal methods are technique-specific and have a required learning curve associated with obtaining specified clinical plication outcomes. Moreover, once treated, the level or resulting tissue alteration achieved is irreversible. The paucity of data demonstrating the long-term mechanical characteristics and viability of these treated ligaments limits the confident and continued use of this technique.

Conventional methods for arthroscopic plication of the shoulder capsule with sutures typically involve freehand techniques that are technically challenging and often time-consuming. An additional shortcoming common to both thermal capsular shrinkage and existing suturing techniques is that neither method can effectively control the amount of capsular tightening in a calibrated fashion. "Over-tightening" of the anterior capsule can lead to problems such as excessive loss of external rotation, limiting shoulder joint function.

Thus, a need exists in the art for an alternative to the conventional methods of tissue repair. There is a need in the art for novel systems and methods for arthroscopic soft tissue repair and/or plication that is adaptable to any soft tissue or soft tissue system and can overcome the shortcomings of conventional methods and improve the clinical outcome as well as be generally adopted by surgeons.

SUMMARY OF THE INVENTION

The present invention provides an alternative and enhancement to conventional methods of tissue repair. More specifically, the present invention presents devices, systems and methods for arthroscopically treating unidirectional and multidirectional instability of tissue in general, and through suturing and/or plication by non-limiting example. An essential and powerful aspect of this invention is its wide applicability to a non-limiting extent of tissues and tissue systems of any shape or size, such as, for example the plication of loose tissue from the interior surface of a spheroidal capsule. One having ordinary skill in the art is cognizant of the applicability of the present invention to as diverse fields as reduction in gastric reflux to lung volume reduction to atrial valve repair and shoulder joint plication. The present invention is not limited to the examples set forth in this disclosure but is extended to all other procedures that would benefit from the devices, systems and methods as described herein. Thus, the scope of the present invention extends beyond the non-limiting examples set forth herein and encompasses that which would be or should be within the purview of one having ordinary skill in the art of tissue repair.

In one described embodiment, the invention relates to suture structures and related deployment devices to repair, plicate and/or reduce the capsular laxity at the glenohumeral joint, improving joint stability. However, the techniques disclosed in the examples below are adaptable and usable for all tissues and tissue systems where repair is beneficial to improve the health and function of the tissue or tissue system. Such techniques and uses, particularly relating to embodiments of the present invention, are particularly useful in applications requiring transdermal access to a particular internal tissue by penetrating one or more layers of tissue. However, such transdermal access is not limiting and the present invention may be applicable in non-transdermal applications as well, such as in fundoplication. Further, "repair" of such tissue, as defined herein and throughout this disclosure, is a slowing down or reversal of the instability such that the tissue is somehow manipulated to deal with or overcome the instability, usually involving some form of surgery. Common, but not limiting, examples include suturing, plicating, stapling, restructuring, adhering, tightening, attaching, firming or the like.

In one exemplary embodiment, the present invention is a system for transdermal repair of soft tissue. The system comprises a first element to pinch a portion of soft tissue that is to be repaired; a second element to repair the portion of soft tissue that is pinched by the first element, such portion of soft tissue being accessed transdermally; and a third element to deploy the first element and the second element in turn to repair the portion of soft tissue that is being pinched.

In another exemplary embodiment, the present invention is a system for plicating a capsular structure. The system comprises a pinching element to pinch a portion of an interior surface of a capsular structure to be plicated; a plicating element to plicate the portion of the interior surface of the capsular structure that is pinched by the pinching element; and a deployment element to deploy the pinching element and the plicating element in turn to plicate the portion of the interior surface of the capsular structure that is being pinched.

In yet another exemplary embodiment, the present invention is a method for arthroscopic plication of an interior concave surface of a capsular structure. The method comprises pinching a portion of the interior concave surface of the capsular structure; and securing the portion of the interior surface that is pinched.

In yet another exemplary embodiment, the present invention is a method for arthroscopic repair of soft tissue within a hollow structure. The method comprises pinching a portion of soft tissue on the interior surface of the hollow organ; and fixing the portion of soft tissue that is pinched.

BRIEF DESCRIPTION OF THE DRAWINGS

FIGS. 3A to 3D show an exemplary grasper mechanism according to the present invention during advancement and grasping of a tissue pleat.

FIGS. 5A to 5E show a distal end of an exemplary deployment device according to the present invention demonstrating a method of tissue plication.

FIGS. 6A to 6L show a distal end of an exemplary deployment device according to the present invention demonstrating a method of tissue plication.

FIGS. 12A to 12E show exemplary deployment device jaws with needle retrieval elements according to the present invention.

FIGS. 13A to 13D show a procedural deployment of a hinge lock plication clip using a grasping mechanism according to an exemplary embodiment of the present invention.

FIGS. 17A to 17D show an exemplary procedural use of an exemplary device according to the device shown in FIG. 16.

FIGS. 18A to 18D show a three-pronged grasper device mechanism according to an exemplary embodiment of the present invention.

FIGS. 19A and 19B show a two pronged grasper device mechanism according to an exemplary embodiment of the present invention.

FIGS. 20A and 20B show an undeployed single armed grasper anchor mechanism according to an exemplary embodiment of the present invention.

FIGS. 21A and 21B show a deployed single armed grasper anchor mechanism according to an exemplary embodiment of the present invention.

FIGS. 22A and 22B show a deployed single armed grasper anchor mechanism according to an exemplary embodiment of the present invention.

FIGS. 27A to 27F show an embodiment of the plication delivery device according to an exemplary embodiment of the present invention with a distal tip in the closed and open positions and a bottom flange having a flexible member that may be displaced to expose a penetrating element.

FIGS. 28A to 28D show a plication delivery device according to an exemplary embodiment of the present invention with a distal tip in the closed and open positions and a bottom flange having a flexible member that may be displaced to expose a penetrating element.

FIGS. 30A to 30F show a plication delivery device according to an exemplary embodiment of the present invention with a distal tip in the closed and open positions and a bottom flange having a flexible member that may be displaced to expose a penetrating element.

FIGS. 35A to 35C show perspective, top, and side views of a two component plication device according to an exemplary embodiment of the present invention that has two points of penetration, extending the region of attachment and distributing the stresses on the device.

FIGS. 36A to 36F show perspective, top, and side views of a two component plication device according to an exemplary embodiment of the present invention that has two points of penetration, extending the region of attachment and distributing the stresses on the device.

FIG. 40A to 40D show perspective and side views of a two component hinged plication device according to an exemplary embodiment of the present invention.

FIGS. 41A to 41F show a two component sleeve-lock device with multiple stages according to an exemplary embodiment of the present invention.

FIGS. 42A to 42F show a perspective, top, and side views of a single component plication device according to an exemplary embodiment of the present invention in the undeployed and deployed configuration. This embodiment can also include use with a pledget backing making it a two component plication device.

FIGS. 43A to 43C show perspective and side views of a single component spring plication device according to an exemplary embodiment of the present invention along with illustrations of device implementation.

FIG. 44A to 44C show a perspective view of a single component plication device according to an exemplary embodiment of the present invention.

DETAILED DESCRIPTION OF THE INVENTION

Figure 1:
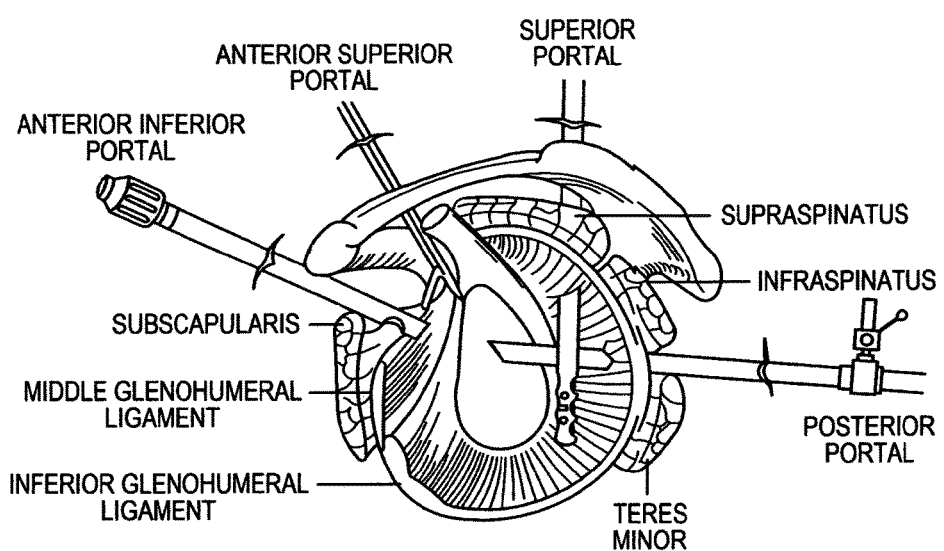
FIG. 1 shows a graphical cross-sectional illustration of conventional arthroscopic instrument position relative to anatomic structures.

The present invention relates to devices, systems, and methods that address deficiencies in conventional methods of tissue repair. The present invention may be applied to a number of different medical applications, including but not limited to repair and/or plication or attachment of soft tissue, such as lung reduction or resection, gastric reduction, intestinal, liver reduction or resection, kidney reduction or resection, esophageal modification, atrial appendage isolation or removal, and anatomic structures. These are mere examples of locations where such devices, systems and methods may be used and in no way are limiting of the broader scope of the present invention.

The devices, systems and methods according to the present invention may be applied to any tissue or tissue structure in any geometry. For example, exemplary embodiments of the present invention may be used to plicate a capsular joint from the interior concave surface of the capsular joint by connection to and mending or suturing of the interior capsular tissue. This ability is one of the advantages of the present invention and is characteristic of its diverse range of application in terms of tissue targets as well as target shape and/or geometry. Conventional methods of plication are either limited to repair from an exterior convex surface of a capsular joint or by traditional hand suturing.

For sake of demonstration, exemplary embodiments of the present invention are shown by providing a technically facile means of arthroscopic plication of the shoulder capsule using a tissue clip or suturing device deployed with a single calibrated hand-held device for the treatment of unidirectional and multidirectional instability of the shoulder joint. The exemplary embodiments of the invention address deficiencies in shoulder capsule ligament plication for shoulder joint stabilization. The same or similar techniques as shown with respect to the shoulder capsule may also be used in virtually any other tissue or tissue structure that could benefit from the embodiments of the present invention. In addition, the exemplary embodiments address similar deficiencies that are apparent in other applications involving plication of tissues such as lung reduction or resection, gastric reduction or bypass, intestinal modifications, liver reduction or resection, kidney, esophageal, atrial appendage isolation or removal, cardiac tissue plication or attachment, and other soft tissue attachment or plication reductions.

A primary purpose of the present invention as shown in some of the exemplary embodiments is to better enable the tightening of the shoulder capsule ligaments either concomitantly or as a primarily course of treatment rather than to specifically repair a disrupted capsule. The expected clinical outcome includes reducing or eliminating any excess anterior inferior translation of the joint as well as resolving any pathologic anterior or posterior translation of the joint, thereby stabilizing the shoulder.

The exemplary plication systems according to the present invention may also be used to reduce or plicate, or attach soft tissue structures for other applications including, but not limited to, applying tension to remove slack in other joint ligaments (e.g., anterior cruciate ligament, medial collateral ligament), re-attaching partially or completely torn soft tissue structures during applications such as meniscus repair, re-attaching partially or completely detached soft tissue structures to bones via bone anchors during rotator cuff repair, Bankart Lesion repair, or other soft tissue to bone attachment procedure, plicating hernias, clipping lung tissue during lung reduction or resection procedures that result in reduced lung volume, gastric reduction or bypass procedures involving plication of the stomach or intestines to reduce the volume of the anatomy, atrial appendage isolation or removal involving clipping the atrial appendage at the orifice to reduce the atrial volume and isolate the interior of the atrial appendage from the circulating blood pool, vessel ligation procedures, tubal ligation procedures, resection of cancer tissue (e.g., liver, breast, lung, colon, etc.), mitral valve repair (leaflet and annular ring) and other procedures which may require soft tissue plication or attachment.

Additionally, various exemplary embodiments of the present invention are described that may be used to repair, plicate and reduce capsular laxity by attaching the capsule to the glenoid labrum or surrounding bony structures in the glenohumeral joint. The deployment devices are capable of grasping the capsular tissues, aligning capsular tissues into the plication region of the device, and deploying a plication clip into the tissue to securely attach the folded tissues. The exemplary deployment devices have the ability to adjust the level of plication by variable pull back of the grasping element or by variable adjustment of the clip device. Furthermore, the exemplary deployment devices may be used to abrade the plicated tissue section to irritate the synovium, eliciting the biological healing and remodeling response of the soft tissue. The dimensions of the exemplary devices may be tailored for orthopedic access with standard arthroscopic equipment. Additionally, the exemplary deployment devices may reposition capsular tissue, or other tissue, and secure tensioned capsular tissue, or other soft tissue, to the labrum, bone, or other anatomy.

By example, the present invention relates to devices, systems and methods that enable plication of ligaments, tendons, and/or other soft tissue structures to reduce unidirectional and multidirectional instability of the shoulder, or other anatomic structure. The region of interest includes the entire 360 degrees of the joint capsule. However, more typically the repair covers approximately 180 degrees (from the 8 o'clock to 2 o'clock anterior position of the capsule). In the instance of multidirectional instability it is common for a surgeon to close the rotator interval that will restrict the anterior and posterior inferior joint laxity and thereby restricting or limiting translation.

In exemplary embodiments of the present invention relating to the shoulder joint, capsular tensioning regions of interest include, but are not limited to, the posterior-inferior and anterior-inferior quadrants of the glenohumeral joint capsule as well as the rotator cuff interval. Capsular plication with device clip embodiments or suture embodiments includes, but is not limited to, capsule-to-labrum plication and capsule-to-capsule interval closure/reduction. An advantage of the capsule-to-labrum plication includes augmentation of the labral shelf by increasing the size of the labral "bumper," reducing the potential for joint subluxation or dislocation.

To accomplish joint stability using the exemplary devices, systems and methods described herein, standard surgical preparation of the site and arthroscopic portals for access of the shoulder joint are performed. The joint may be dilated with an arthroscopic pump. The deployment device is introduced through a standard 5, 6 or 8 mm cannula placed in the anterosuperior arthroscopy portal. The anterior and posterior sections of the capsule may be visualized via placement of the arthroscope through the accessory anterior inferior portal or the posterior portal. Regions of the anterior and posterior inferior glenohumeral ligament are assessed and identified for removal of excess capsule laxity by plication with the primary goal of reducing the overall capsular volume. The deployment device is moved into position over the ligament region to be reduced/plicated. The tissue grasping mechanism is deployed through the centerline of the deployment device jaws, creating a tissue fold that is drawn up to and into the jaws of the deployment device. To improve the angle of approach of the deployment device in relation to the capsular plication region, the shaft of the device can be designed to have different configurations, including but not limited to straight, angled, or curved (S or C-shaped) shaft or angled distal jaw region.

Various embodiments can be utilized for the tissue grasping mechanism and include, but are not limited to, jaw clamp with or without an active hinge, J-hook (made of deformable metal, superelastic material, or plastic), penetrating tip element with a deploying end (e.g., umbrella, balloon, or T-shaped) that resists pullout of the device, or a corkscrew design (made of deformable metal, superelastic material, or plastic). A common ability with tissue grasping mechanisms is the ability to grab, hold, and move tissue into the jaws of the deployment device. The advantage of using a grasping mechanism to align the tissue and bring the tissue into the deployment device jaws is the ability to adjust the level of plication that will be employed. The force required to pull back the tissue into the deployment device jaws is maintained by the grasping mechanism through a spring or elastic joint/hinge. The jaw of the deployment device may have a center channel which enables closing of the jaw without being impeded by the grasper.

An exemplary embodiment of the deployment device includes an electrode stimulator that can be engaged along with the grasping mechanism or the clamping mechanism. (See, for example, FIG. 15.) The purpose of the stimulator is to identify the potential proximity of the axillary nerve (other nerve or muscle tissue) to the plication region prior to deploying the tissue plication clip. The axillary nerve is typically located within 1-2 cm of the inferior capsule. In short, the grasping mechanism can include coupling of a stimulator element that can be excited to a level that would invoke activation of the axillary nerve and corresponding muscular response (e.g., deltoid muscle contraction) if the area of plication is located at or near the position of the axillary nerve. Any indication of muscle stimulation will provide a warning mechanism to the surgeon of the close proximity of the axillary nerve structure and potentially prevent unintended damage to the nerve.

Several strategic locations along the deployment device jaw will have embodiments that allow for tissue penetration (e.g., needles, barb) and/or abrasion (e.g., rasp or roughened) of select regions of the ligament tissue. This stimulation/abrasion of the ligament is intended to occur simultaneous with engagement of the deployment device jaw. The purpose of this penetration and/or abrasion is to elicit a biological response that promotes more rapid healing and remodeling/scarring of the plicated ligament tissue by irritating the synovium.

Some exemplary embodiments of the suture device may include the use of flexible and rigid elements, suture or suture materials, and pledget backings that may allow for proper securing of the plicated or attached soft tissue. The embodiments of the deployment device jaw may include mechanisms to engage the suture to the jaws (e.g., at the distal tip, along the jaw flange). One flange of the jaws holds the penetrating element of the suture device, while the opposite side has locking ports to grab the suture tips. Engagement of the jaws is performed by user actuation of the proximal handle. Upon engagement of the deployment device jaw, with the plicated tissue grasped and aligned, the suture tips engage the tissue between the jaws, penetrate the tissue, and engages with the opposite locking ports. Once full engagement of the deployment jaw has been achieved, the suture ends have been fully deployed through the tissue fold to be plicated, the suture tips will be locked into the jaw flange. The deployment device jaw is then opened, and tissue released. The deployment device is then withdrawn from the site along with the suture ends. The suture ends are retrieved by the surgeon and standard sliding knots are tightened and locked by pulling the free end of the suture and advancing the knot to the plication site. The shoulder is then placed through a trial range of motion while the tension portion of the capsule is visualized with the arthroscope. Adequate fixation of the capsular plications is verified.

Exemplary embodiments of the suturing device mechanism may also include various locking port configurations which do not require passing of rigid suture tips, but rather suture ends. Further embodiments also includes passing of multiple sutures during one deployment that can be distributed in different configurations along the phalanges of the jaw (e.g., perpendicular, parallel, overlapped, cross-over, etc.). Other embodiments may also include pre-tied suture devices and/or pledget backings.

Surgically, the reduction in ligament laxity is continued and repeated along and round the capsule, deploying as many suture devices that may be required and in any 3-dimensional geometric pattern around the capsule to reduce capsular volume and stabilize the joint. Deployment of multiple devices can be required during the capsular laxity treatment procedure. This is particularly true for the treatment of multidirectional instability of the shoulder. The number, orientation and position of deployed clip devices will be user defined, no limitation is specified. Furthermore, the level of capsular plication or reduction in capsular laxity will be user defined, no limitation is specified. Furthermore, it should be noted that various embodiments of the suture device may be deployed in each case, particularly in cases where a combination of capsule to capsule and capsule to labrum or capsule to glenoid plication are indicated.

It should be appreciated that the plication devices described, including sutures and deployment mechanisms, can be applicable for use in other indications involving devices that are used for plicating and attaching tissue layers where small arthroscopic access is required. The embodiments of this invention can be tailored to human anatomy, however, they may also be tailored for use in other species such as horses, dogs, sheep, and pigs as well as invertebrates.

These plication systems can be used to reduce or plicate soft tissue structures or attach tissue layers for application including, but not limited to, other joint ligaments (e.g., anterior cruciate ligament, medial collateral ligament), rotator cuff repair, Bankart Lesions, meniscus repair, hernias, lung resection, gastric reduction procedures, cancer tissue removal (e.g., liver, breast, colon, lung, etc.), and other procedures which may require soft tissue plication. One having ordinary skill in the art would be cognizant of the procedure to use in performing the above operations using the exemplary devices described herein.

The exemplary embodiments of the present invention provide additional advantages that include, but are not limited to: providing an arthroscopic approach for the plication and reduction in ligament laxity; reducing the visible scars associated with open surgical procedures by small port access required by the deployment device; reducing the complexity associated with arthroscopic knot tying; reducing the incidence of axillary nerve damage by a verification of device positioning; enabling a maneuverable and rapid deployment of plication sutures, reducing the required surgical time as well as the level of complexity associated with the procedure; allowing for adjustable and reproducible levels of tissue plication; adding the option of releasability and removability of a device from the plication region; minimizing potential damage to the articular surface by using devices and materials that can be secured to the tissue as well as have less abrasive properties relative to tissue; and using active embodiments of the device which may allow for diagnostic measurement of positioning relative to neuromuscular tissues and active tensioning of plication regions.

Although many examples below are provided with respect to the shoulder capsule and using a plication procedure, these are only exemplary and are used for their sake of simplicity. Wherever the term "plication" is used with respect to the examples, the broader term "repair" may be substituted to refer to surgical procedures that may not necessarily be plication. Similarly, the shoulder capsule, as described in the examples below, may be substituted by any other tissue or tissue structure that could also benefit from the procedure as described below.

A conventional arthroscopic approach to the glenohumeral joint with the humeral head removed for clarity is shown in FIG. 1. A standard posterior portal for diagnostic arthroscopy is shown along with two anterior portals created using an outside-inside technique, approaching the joint through the rotator interval area above the subscapularis tendon. An additional accessory superior posterior inferior portal can also be created. From a combination of these portal positions, a standard diagnostic glenohumeral arthroscopic examination can be performed. This includes examination of glenohumeral ligament laxity or damage at the glenoid labrum region of the joint. Excessive ligament laxity or excessive capsular volume is identified by the ability to move the arthroscope from the posterior to anterior inferior glenohumeral ligament space without much difficulty. Once capsular laxity is identified, methods for plication or reduction in the excessive tissue are performed in order to improve the joint stability. Clinical results suggest that the combination of arthroscopic plication of the glenohumeral ligaments in combination with thermal shrinkage procedures can provide results similar to those observed with open surgical procedures. However, as is typically the case, open surgical techniques have an increased risks associated with further tissue damage and infection than through arthroscopic means.

Figure 2A:
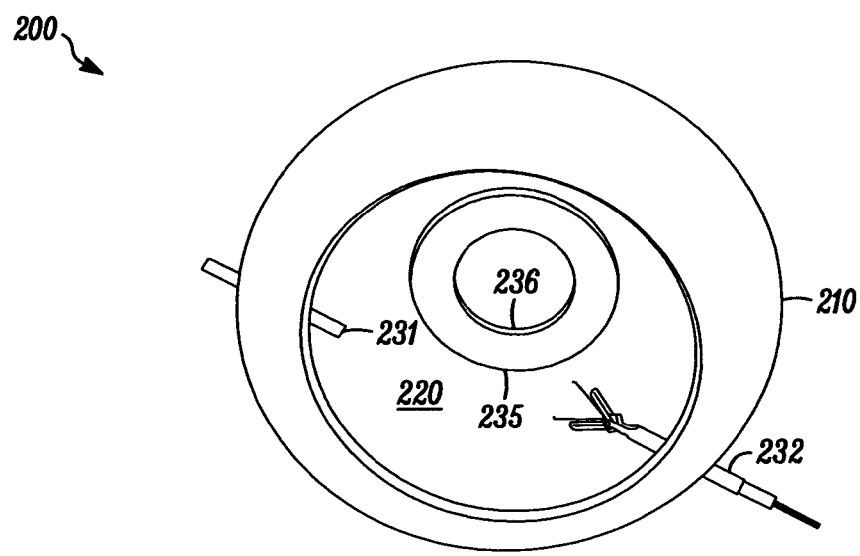
FIGS. 2A and 2B show an exemplary arthroscopic plication deployment device according to the present invention in a capsular region with clips positioned in the areas of plication.
Figure 2B:
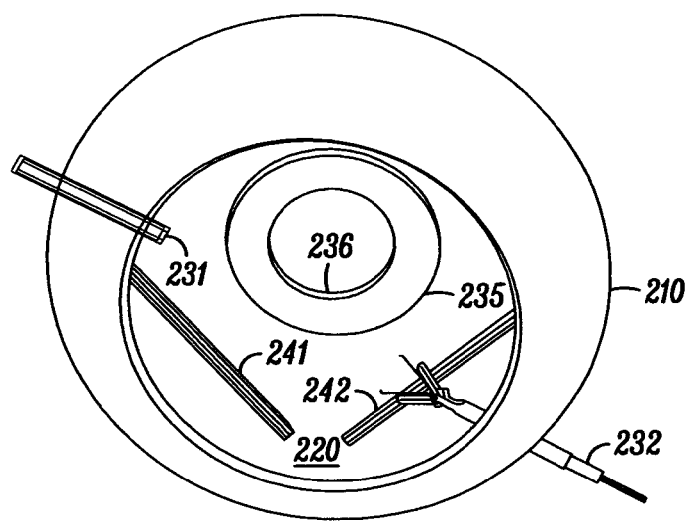
Figure 4A:
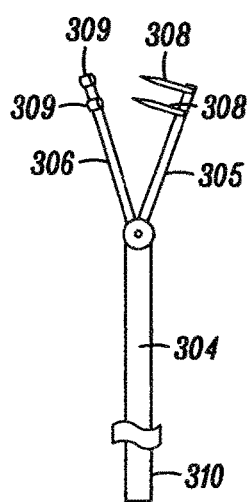
FIGS. 4A and 4F show an exemplary embodiment of the deployment device according to the present invention.
Figure 4B:
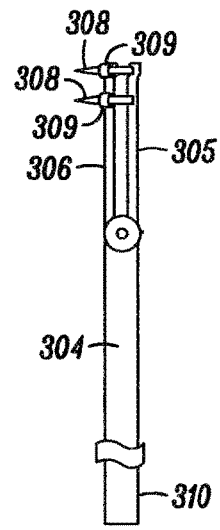
Figure 4C:
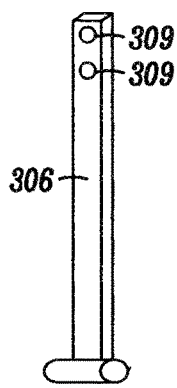
Figure 4D:
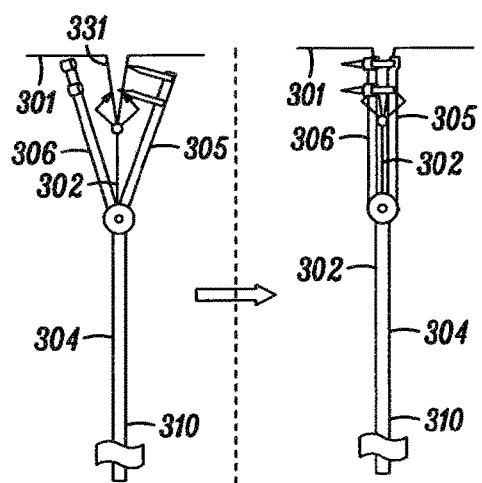
Figure 4E:
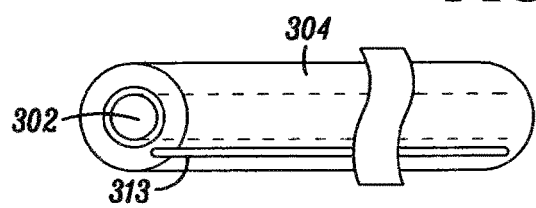
Figure 4F:
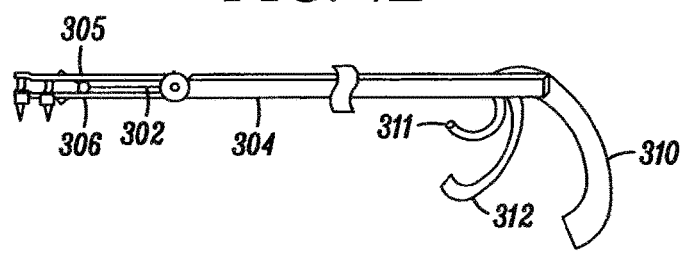
Figure 6B:
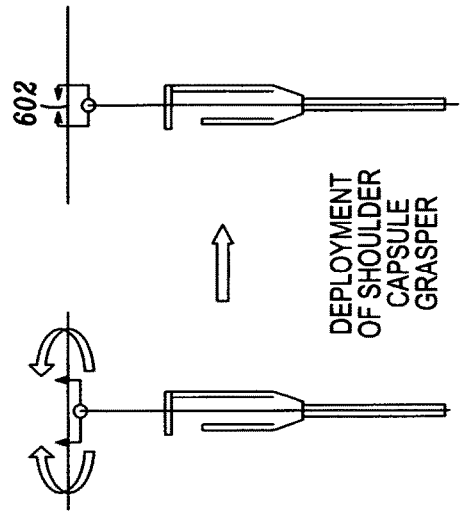
Figure 6E:
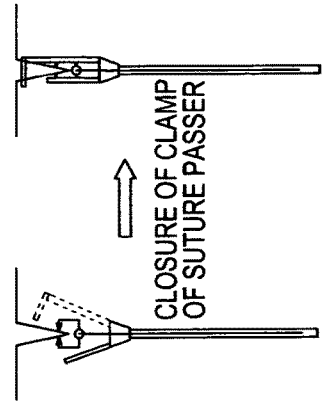
Figure 6D:
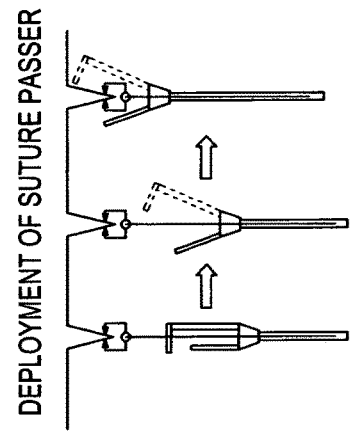
Figure 6A:
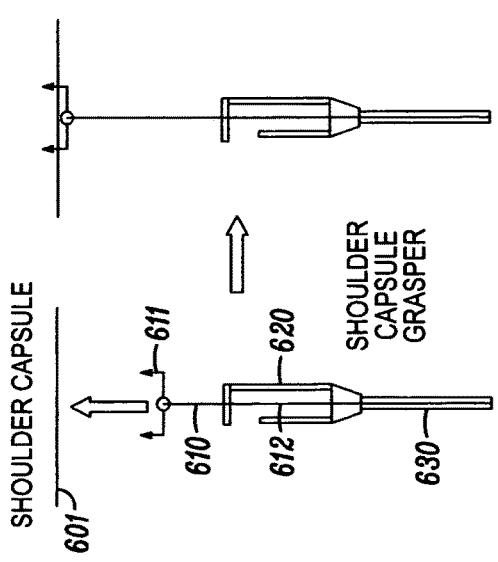
Figure 6C:
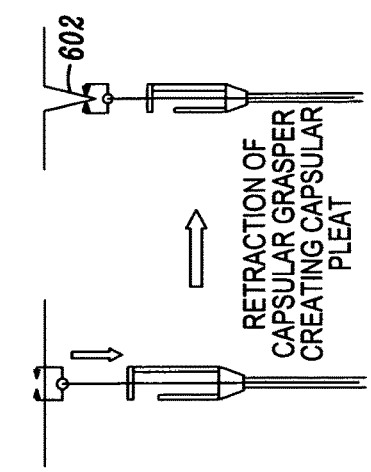
Figure 7A:
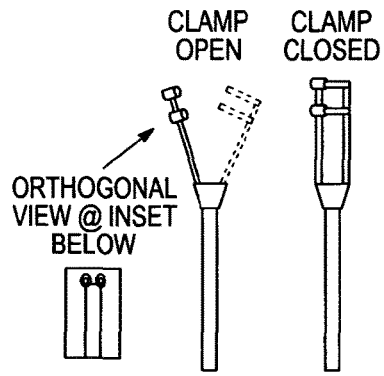
FIGS. 7A to 7J show a distal end of an exemplary deployment device according to the present invention demonstrating a method of tissue plication.
Figure 7B:
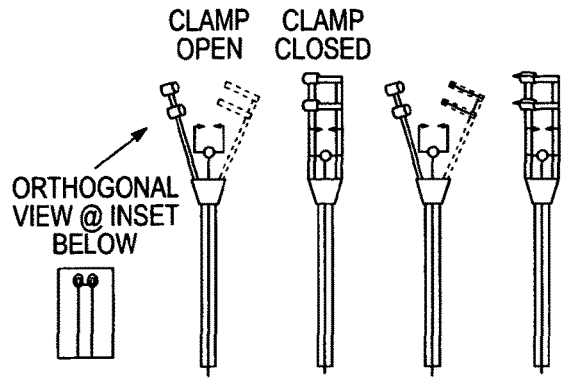
Figure 7C:
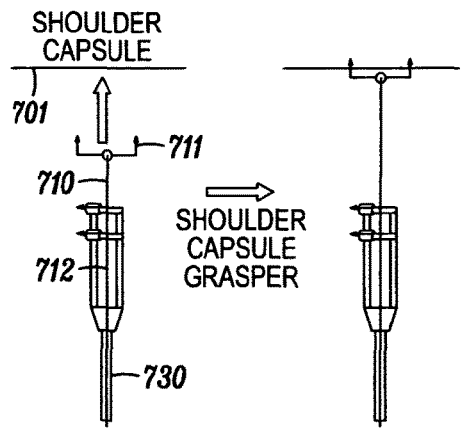
Figure 7D:
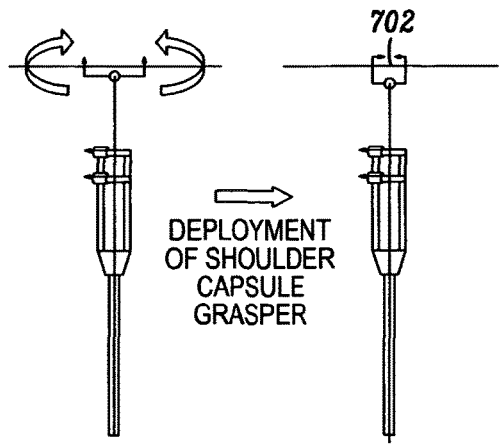
Figure 7E:
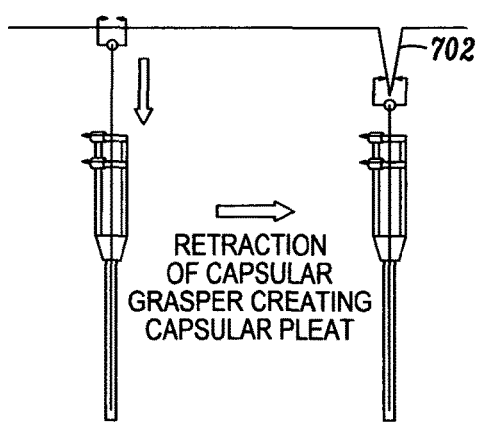
Figure 7F:
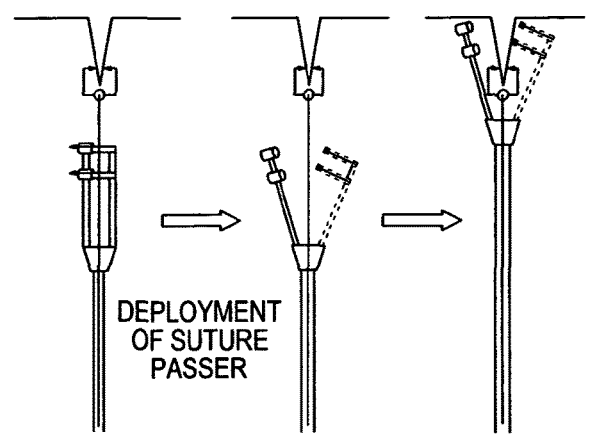
Figure 7G:
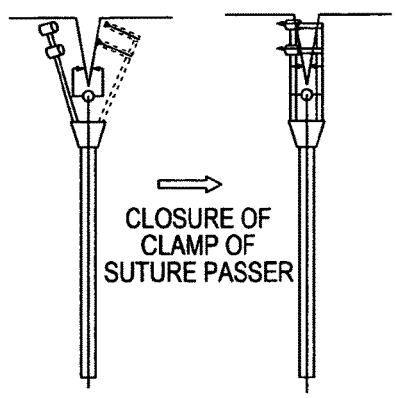
Figure 7H:
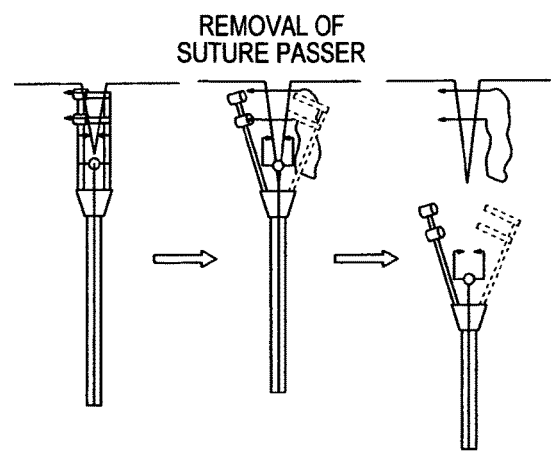
Figure 7I:
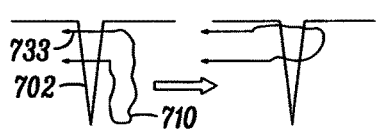
Figure 7J:
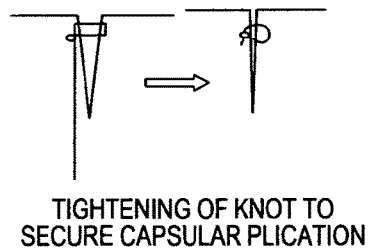
Figure 8A:
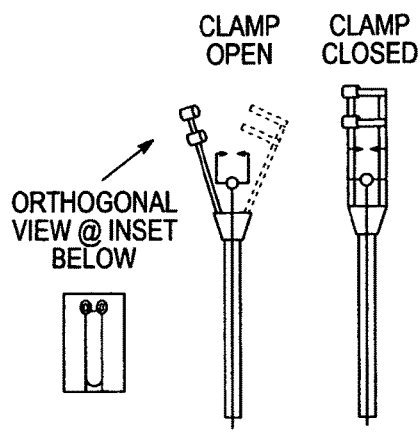
FIGS. 8A to 8I show a distal end of an exemplary deployment device according to the present invention demonstrating a method of tissue plication.
Figure 8B:
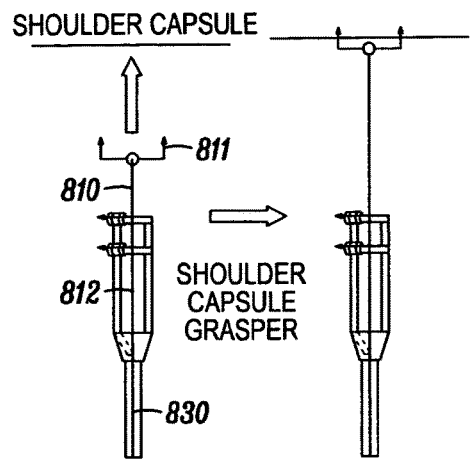
Figure 8C:
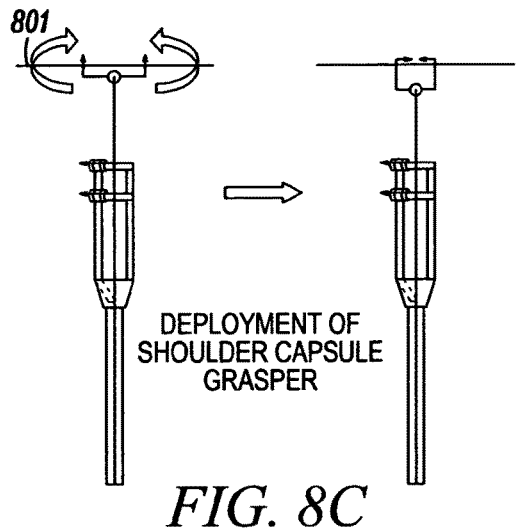
Figure 8D:
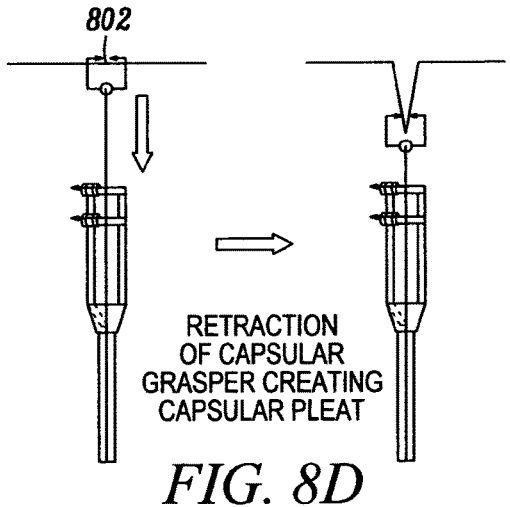
Figure 8E:
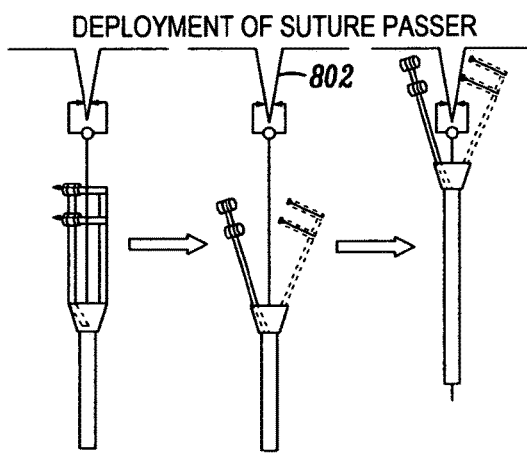
Figure 8F:
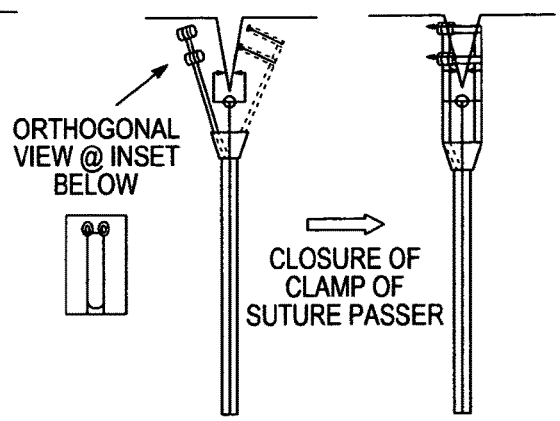
Figure 8G:
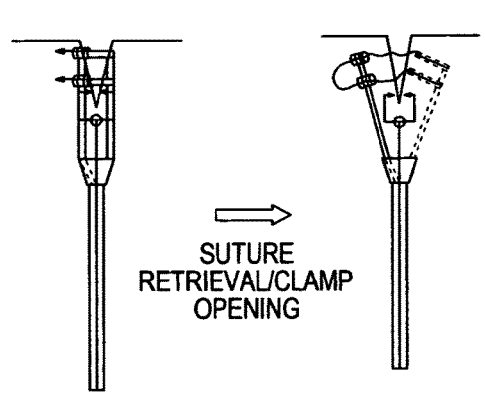
Figure 8H:
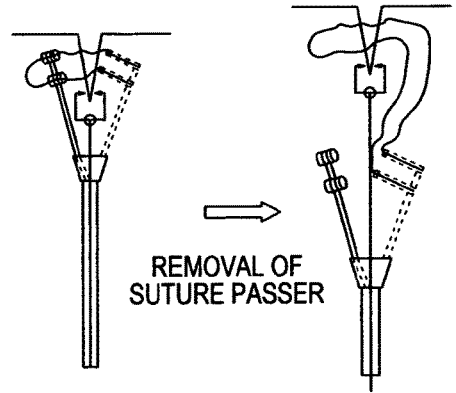
Figure 8I:
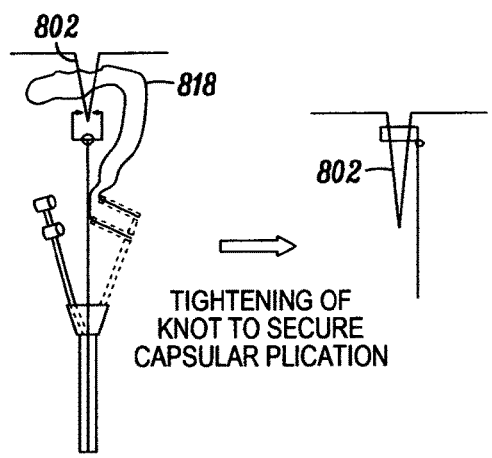
Figure 9A:
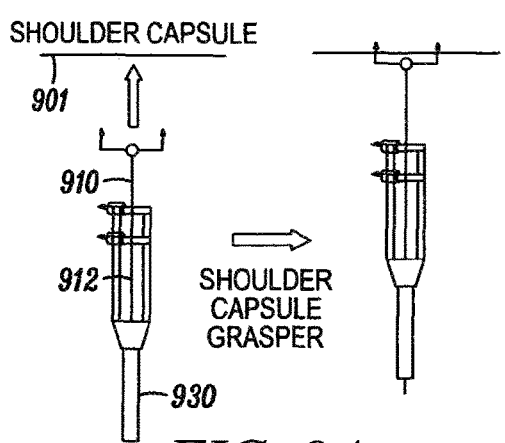
FIGS. 9A to 9G show a distal end of an exemplary deployment device according to the present invention demonstrating a method of tissue plication.
Figure 9B:
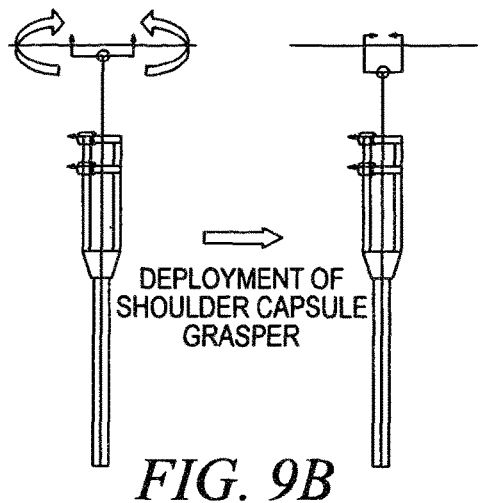
Figure 9C:
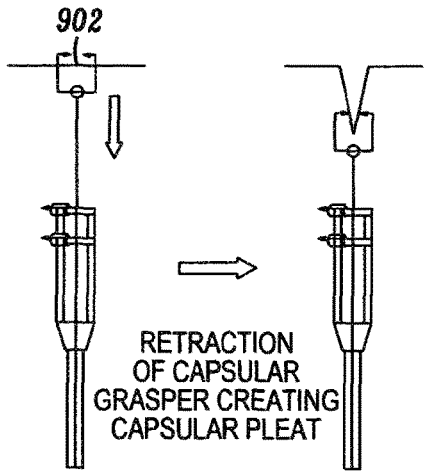
Figure 9D:
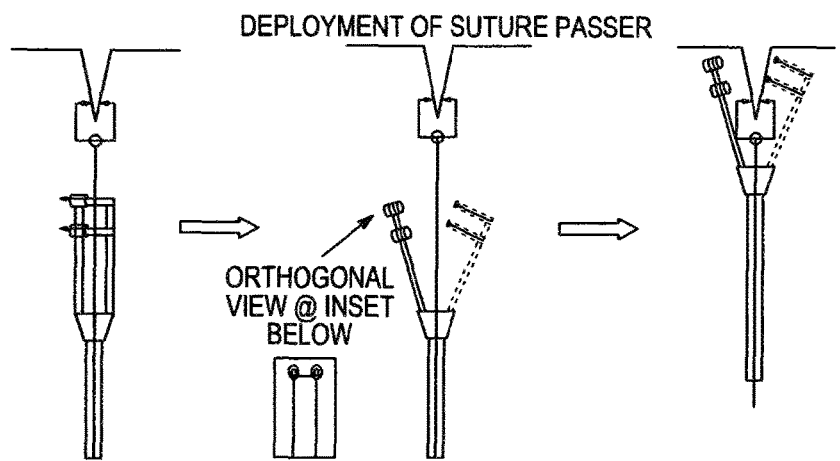
Figure 9E:
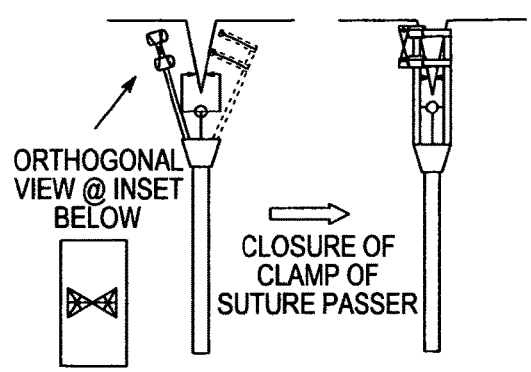
Figure 9F:
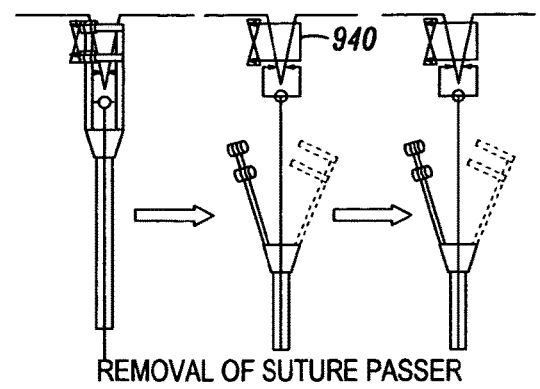
Figure 9G:
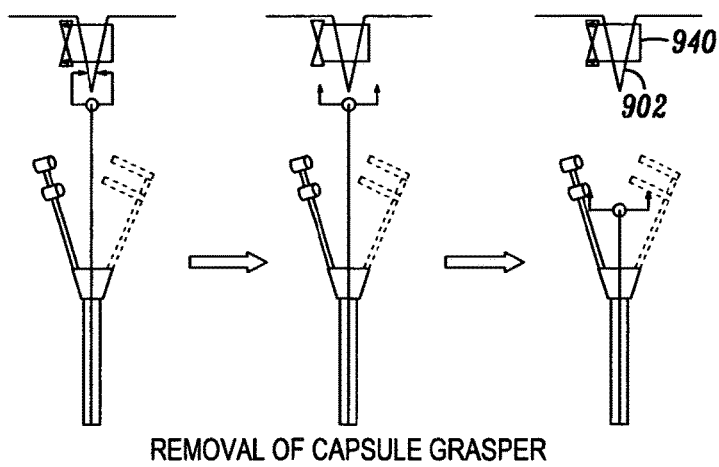
Figure 10A:
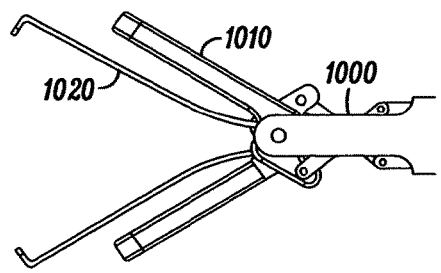
FIGS. 10A to 10D show an embodiment of the distal tip and shaft of the plication deployment device according to the present invention.
Figure 10B:
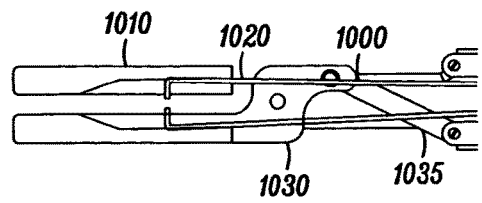
Figure 10C:
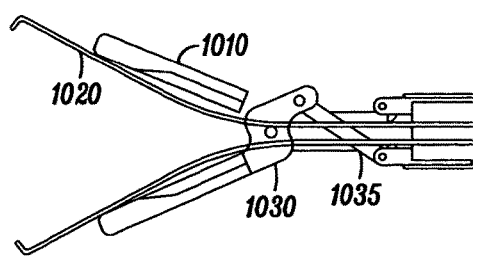
Figure 10D:
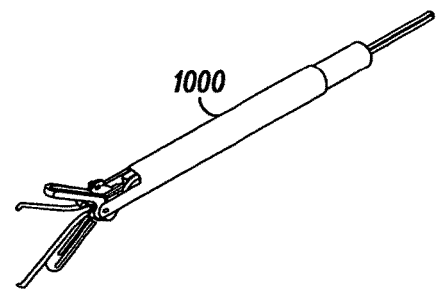

The present invention may be used arthroscopically, shown in FIGS. 2A to 2B as a schematic cross-sectional drawing of an arthroscopic approach of the glenohumeral joint with the humeral head removed for clarity. These figures demonstrate the insertion and position of an exemplary embodiment of an arthroscopic deployment device 232 according to the present invention in position (A) during pre-deployment and in position (B) during post-deployment of exemplary clip plication devices according to the present invention. The clip plication devices shown in these figures are a single example of the many exemplary embodiments that may be used herein and are described in this disclosure. Additionally, the position, orientation, and location of the clip devices are intended only for representation, and do not limit or dictate the positions, orientations, location, and number of devices that should be used. One having ordinary skill in the art would be cognizant of the position, orientation, location and number to use for a specific purpose without undue experimentation. Furthermore, the figures shown here and throughout this disclosure are not intended to be drawn to scale, but rather are for illustrative purposes.

An exemplary embodiment of the capsular grasper is shown in FIG. 3. This embodiment is comprised of a distal tip 302 that has articulating cantilevered arms 303 with teeth that can perforate the shoulder capsule tissue 301 when deployed using a handle 310 (shown partially). The grasper is advanced forward to position it in contact with the capsule tissue 301. The cantilevered arms 303 with teeth engage the capsule tissue 301 and clasp the tissue as the articulation is closed forming a tissue pleat, such as shown in FIG. 3D. Articulation of the grasper mechanism is controlled at the proximal handle 310. The grasping of the tissue pleat permits the ability to provide traction on the shoulder capsule and mobilize the pleat into the jaws of the plication deployment device embodiment.

In another exemplary embodiment of the invention shown in FIG. 4, a distal tip of a plication deployment device 304 is shown in more detail. The device is composed of a grasping embodiment positioned at the centerline of the jaws and two articulating phalanges 305 and 306 (forming the device jaw). The grasping embodiment as shown, can be extended beyond the mouth of the device jaw, grasp tissue, and bring the tissue back into the jaws. The upper and lower phalanges 305 and 306 of the device are articulating elements that are controlled at the device handle 310 by the user. In an exemplary embodiment, one phalange 308 embodies two hollow spikes 308 that upon closure of the jaw will perforate a retracted capsular pleat 331. The phalange on the opposite side 306 embodies two circular orifices 309 that are in-line with the spikes 308 and act to capture the spikes of the other phalange when the jaw is closed, as shown in FIG. 4B. To facilitate the jaws ability to completely close, the phalanges 305 and 306 have channels that can be through thickness, allowing the grasper to sit within the jaws, but not impede actuation or closure of the jaws. In other embodiments, one of the phalanges may be fixed, thereby having only one articulating phalange of the jaw. In other embodiments, the spiked phalange can have only one hollow spike or more, for example, up to 6 hollow spikes.

It should be appreciated that in the embodiment shown in FIG. 4, the shaft of the capsular grasper 302 is contained in the shaft of the plication deployment device 304. In other embodiments, the shaft of the capsular grasper 302 may also be contained adjacent or off center to the jaws of the plication deployment device. In the embodiment where the capsular grasper is at the centerline of the device, this relationship permits the grasper to piston axially within the passer so that retraction of the deployed grasper delivers the capsular pleat into the jaws of the deployment device. Furthermore, in another embodiment, the extent of pistoning or displacement of the capsular grasper within the shaft of the deployment device can be calibrated. This calibration permits quantification of the length (size) of the capsular pleat and, hence, the amount of tightening of the shoulder capsule (e.g., more retraction of the grasper creates a larger pleat which, in turn affects the tightness of the capsule). The handle 310 may have various triggers 311 and 312 to allow the movement of the shafts of the grasper 302, the suture passer 304 and the suture retriever 313 relative to one another.

Another exemplary embodiment for passing suture to secure the pleat of the capsule is shown in FIG. 5. In this figure, a suture retrieval arm 313 is contained within one of the phalanges 306 in the plication deployment device. An embodiment of the suture retrieval arm has a distal tip that allows for catching of the suture in one preferential direction. The suture retrieval arm 313 may be advanced in a piston motion axially within the shaft of the plication deployment arm 313. An embodiment of the suture (including a pre-tied sliding knot) is pre-loaded into the plication deployment device in the form of a reloadable cartridge 315. The pre-tied sling knot can be loaded into the proximal spike of the phalange 314, and the positioning of the knot ensures that the suture retrieval arm passes through the loop of the knot when the arm is deployed. After the free end of the suture is hooked, the suture arm is retracted. The integrated instrument is removed, leaving a horizontal mattress suture 314 at the base of the capsular pleat. The sliding knot is tightened by pulling the free end of the suture, as shown in FIG. 5E. Various embodiments can use either resorbable or non-resorbable suture types as well as varying suture sizes. In addition, instead of sliding knots, anchors (not shown) that pass over the suture ends and prevent retraction of the suture can be advanced over the suture ends until the knot is secured.

An alternate embodiment includes the phalange spikes having a pre-loaded U-shaped short suture segment whose ends are attached to elastic barbs. The opposite phalange is pre-loaded with a short suture segment with rigid rings attached at both ends. The orifices of the non-spiked phalange dictate the position of the two suture rings. When the jaws of the plication deployment device are closed, the two barbs deploy into their two respective rings. This creates a closed ring of suture (in a horizontal mattress pattern) through the base of the capsular pleat.

FIG. 6 depicts a series of exemplary steps that may be used to repair or plication tissue 601 using a repair deployment device 610 according to the present invention. After advancing the repair deployment device 610 to the region of interest, the grasper mechanism 611 is deployed. The grasper is advanced beyond the jaws of the device, as shown in FIG. 3, and the cantilevered arms of the grasper engages the tissue 602, as shown in FIG. 6. The grasper 611 is then retracted, forming a tissue pleat 602 as it is drawn into the jaws of the repair deployment device 610.

In the exemplary embodiment shown, the jaws of the device 610 open as the grasper is retracted 611. In other embodiments, the jaws may be manipulated independently to the grasper mechanisms from the proximal handle of the device. The retracted grasper draws the tissue pleat 602 into position within the jaws of the device. As mentioned in the embodiment described in FIG. 4, the amount of plication or tightening of the capsule is a function of the amount of pleat that is drawn into the jaws, which is controlled by the position of the grasper. Once the tissue pleat is in position, the jaws of the repair deployment device are engaged.

In the embodiment shown, there may be one, two or more hollow penetrating spikes positioned in a horizontal or vertical position at the distal tip of the device, such as shown in FIG. 3 and FIG. 7. Upon engaging of the jaws, these spikes will penetrate the tissue pleat. Similar to the mechanism described in FIG. 5, a preloaded suture 612 with a pre-tied sliding knot, extending through the suture grasper 620 and anchored to a suture grasper 630, can be loaded into the spikes. A suture retrieval arm is advanced along the jaw of the deployment device and as previously described can engage the suture. After the free end of the suture is hooked, the suture arm is retracted. The integrated instrument is removed, leaving a horizontal mattress suture 631 at the base of the capsular pleat. The sliding knot is tightened and locked by pulling the free end of the suture and advancing the knot. Various embodiments can use either resorbable or non-resorbable suture types as well as varying suture sizes.

FIG. 7 depicts another exemplary embodiment 710 of the suture clip with a grasper 711 engaging tissue 701 with a suture 712 anchored supplied through a suture grasper 730. Shown in this example is a suture element with both ends having spikes or needles that allow for loading into the repair deployment device distal tip and deployment through the capsule tissue upon engagement of the jaws, as described in the previous embodiments. In this embodiment, the dual spiked suture clip is passed through the tissue pleat 702 from phalange to phalange. The ends are retrieved and standard sliding knots are tightened and locked by pulling the free end 733 of the suture and advancing the knot.

FIG. 8 shows another exemplary embodiment of a suture clip and repair deployment device 810 wherein the suture 812 or clip material is loaded into a non-spiked phalange 811. In this embodiment, the spiked ends of the opposite phalange will engage the suture or clip material when full jaw engagement is performed. As a result, the spikes will penetrate the tissue pleat 802 then engage the suture 812 or clip material. Opening of the jaw will result in the suture or clip material to be withdrawn with the spiked phalange, pulling the material through the tissue pleat. The device would then be withdrawn. The suture slack 818 and ends are retrieved and standard sliding knots are tightened and locked by pulling the free end of the suture and advancing the knot.

The exemplary embodiment shown in FIG. 9 shows another suture clip according to the present invention. Similar to the previously described systems of FIGS. 3 to 8, the embodiment here utilizes the same grasping mechanisms to generate the tissue pleat 902 and pull the pleat within the jaws of the repair deployment device 910. The difference in this embodiment is the use of a suture clip 940 or a U-shaped clip that can be loaded into the distal end of the spiked jaws. In this case, the spikes can be a characteristic of the jaws or a characteristic of the distal tips of the suture clip or U-shaped clip devices. In either case, the purpose of the spiked ends is to penetrate the tissue pleat. On the opposite jaw, a locking base is loaded to mate with the suture clip or U-shaped clip. Once the grasper mechanism has been deployed and the tissue pleat is in position within the jaws of the repair deployment device, the jaws can be engaged. Engagement of the jaws results in the suture clip or U-shaped clip to penetrate the tissue pleat and lock into the base on the opposite phalange. The locking of the clip into the base then does not require knot tying, but rather a firm repair of the tissue pleat is generated. The pleat is then released from the grasper and plication deployment device withdrawn.

In the exemplary embodiment shown in FIGS. 10A to 10D and FIGS. 11A to 11H, a repair deployment device 1000 is shown without and with a clip device 1030 at the distal tip of the device jaw, respectively. The proximal end of the deployment device 1000 is not shown for sake of simplicity. Note that the proximal handle of the device will allow for actuation of the distal tip jaws as well as manipulation of the grasper mechanism. This actuation can be independently controlled or interconnected so a single handle actuates both mechanisms, similar to the handle shown in FIG. 4F.

The overall dimensions of the deployment shaft for device 1000 include the ability to be delivered through a 5 to 8 mm arthroscopic cannula. In addition, embodiments of the proximal end of the device can include a rotational translating mechanism associated with the shaft, allowing for adjustment in the rotational alignment of the shaft and hence the jaws with respect to the actuating handle. This rotational adjustment can be located at or adjacent to the pivot point of the jaws to the shaft, or along the shaft.

Alternatively, the shaft can be fabricated from a shape memory alloy configured to exhibit martensitic properties at the operational temperatures (e.g., 37 degrees Celsius). Therefore, the shaft can be bent into the desired curve, along with the inner cabling components. After the procedure, the device may be heated above the austenitic transformation temperature such that the instrument returns to its memory straight position. A primary purpose of changing the jaw actuation axis versus the handle axis is to allow the user to change the angle or position of the jaws relative to the ligament tissue without requiring the user to perform macroscopic manipulate the actuating handle, which is confined by the cannula and access point into the working cavity. In addition, a ratcheting rotating mechanism for positioning of the device shaft over up to 360 degrees enables locking the device shaft at a specified rotational position to the handle so the operator can access more capsular locations than would be available with a rigid straight shaft. The instrument shaft can alternatively be fabricated with a curve or bend, the instrument can be fabricated from a malleable alloy that doesn't exhibit shape memory properties provided the permanent bends do not affect the fatigue lifecycle of the instrument or render it aesthetically inadequate.

In practice, various clip device embodiments (see clip design embodiments) could be implemented at the distal tip of the device jaws. The centerline grasper embodiment has variations (see grasper embodiments). In the grasper embodiment shown, the deflection of the grasper is inherent in the design. The grasper may be constructed of material(s) that allow for elastic deformation of the arm elements (e.g., super-elastic materials such as Nitinol, stainless steel, 17-7, stainless steel 304, stainless steel 316, or other biocompatible stainless steel, other alloy, aluminum, superelastic polymers, sintered metals, machined metals, carbon fiber, gas impregnated nylon, polycarbonate, ABS, other polymers, or insert molded composite materials).

The end of the grasper may be pre-shaped into the open position, opening to an angle from 0 to 90 degrees. The distal tip length of the grasper (which is deformed to a predetermined opening angle) may range, from, for example, from 1 to 50 mm in length. The grasper may be positioned in a central lumen of the deployment device. As shown in the figures, the upper and lower jaws of the deployment device may have tapered channels or guiding channels in which the undeployed grasper arms can sit during the initial advancement of the deployment device through the arthroscopic cannula. Furthermore, the shape of these channels aid in the guiding of the deployed grasper back into the jaws. Note the spacing between jaws allows room for both the clip device at the distal tip as well as the thickness of tissue drawing into the jaws with the grasper. The capsular tissue thickness varies between 1 and 7 mm.

Upon deployment (e.g., forward push out) of the centerline grasper, the specified angular deformation of the grasper tip will open up the arms 1010 because they are no longer constrained by the centerline channel. Pull back of the centerline grasper will result in closing of the clamps and pull back of a specified segment 1101 of tissue 1100 into the jaws of the deployment device. The level of plication will depend on the distance at which the grasper arms are drawn into the deployment device. The range of plication distance for capsular plication application is typically between 1 and 25 mm, more specifically between 2 and 10 mm. More or less tissue plication can be chosen by adjustment in the position of the grasper arms. The length of tissue plicated (e.g., plication distance), depending on the application and extent of the capsular laxity, will typically range between 1 and 50 mm; more specifically between 5 and 20 mm. It should be noted that for this and other non-capsular plication applications, the plication distance can be greater than 25 mm, depending on the application and soft tissue characteristics. The amount of tissue plication can be chosen by adjusting the position of the grasper arms relative to the plication clamp jaws. Force gauges can be connected to the grasper to measure the tension placed on the capsule during plication.

Alternatively, springs (static or adjustable) can be connected to the grasper to direct a specified amount of tension applied to the capsule by the grasper thereby producing a specific amount of tissue plication. In addition, axial distance of grasper movement relative to the plication clamp can be regulated to control the amount of plication as determined by distance as opposed to tension as described above.

The actuation of the jaws 1010 and grasper deployment 1020 can be linked or can be independent in motion. The benefit of individual independent motion is augmentation in clamping that the jaws can provide with this embodiment of grasping. In other embodiments, the benefit of independent motion may not demonstrate this distinct advantage. The mechanism of actuation of the deployment device jaws includes both forward and backward linkage actuation by simple linear motion from the actuating handle. The arrangement of the hinge linkage allow for considerable force generation at the distal tip of the deployment device. Moreover, the simplicity in design provides a relatively problem free hinge mechanism that can be cleaned easily. The shaft of the deployment device is made to have characteristics that allow for easy insertion though the arthroscopic cannula and no clinically relevant abrasion to the surrounding soft tissues.

Figure 11A:
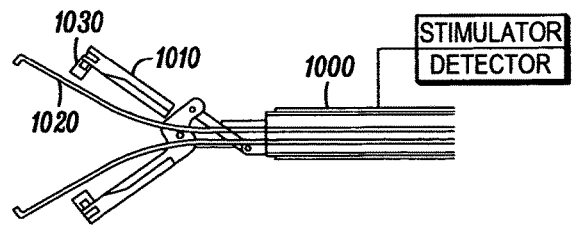
FIGS. 11A to 11H show an exemplary embodiment of the distal tip and shaft of the plication deployment device according to the present invention with an exemplary embodiment of a clip device at a distal tip of the jaws.
Figure 11B:
Figure 11C:
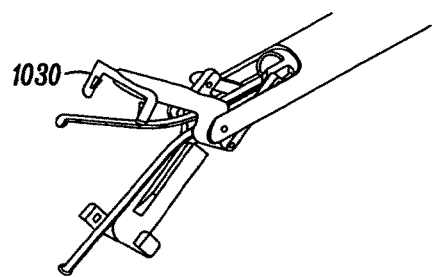
Figure 11D:
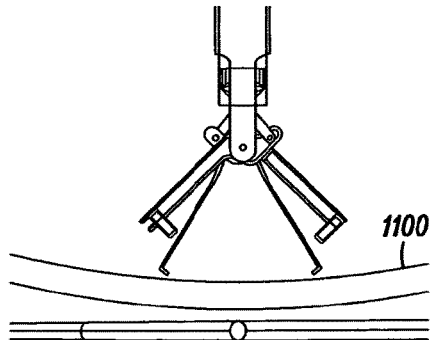
Figure 11E:
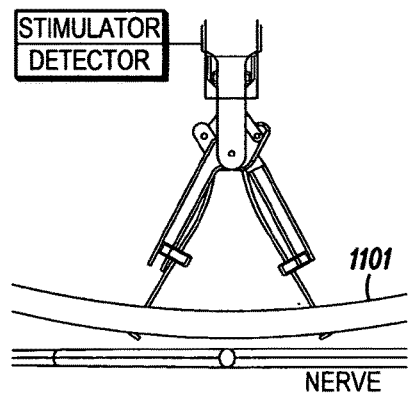
Figure 11F:
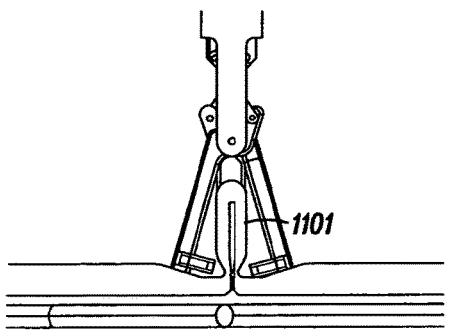
Figure 11G:
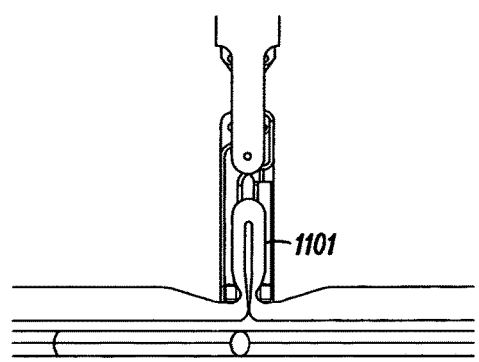
Figure 11H:
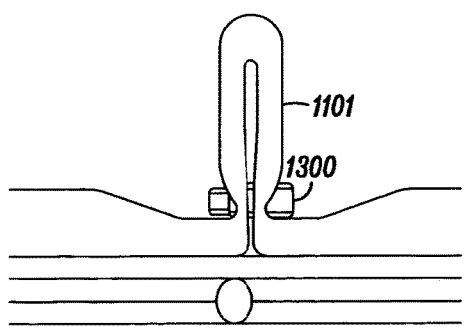
Figure 14A:
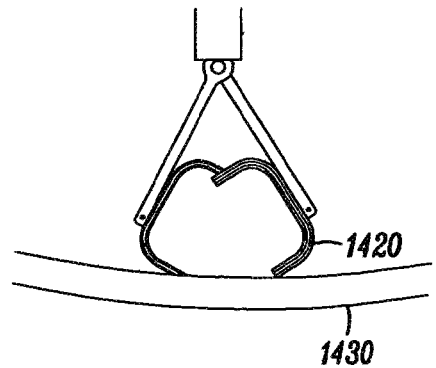
FIGS. 14A to 14D show a procedural deployment of a hinge lock plication clip without a grasping mechanism according to an exemplary embodiment of the present invention.
Figure 14B:
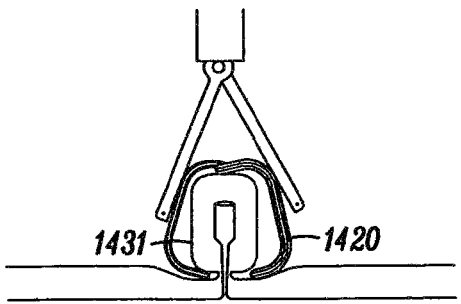
Figure 14C:
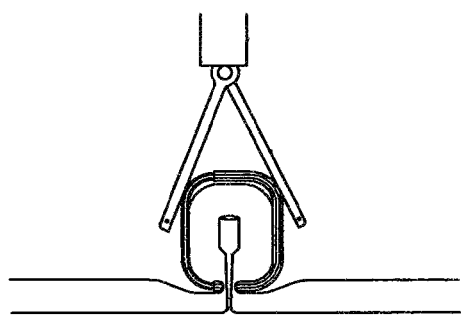
Figure 14D:
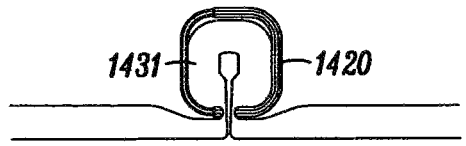

Once the tissue has been drawn into space between the jaws of the deployment device and the grasper position is locked, the jaws of the deployment device can be fully actuated, engaging the tissue fold between the ends of the plication clip, as shown in FIG. 11F. The exemplary clip device 1300 shown in this embodiment is a two-piece device with the penetrating component held in the upper jaw and the base or locking component held in the lower jaw. The individual components are held into position at the distal tip of the jaw either using a snap-fit or mechanical locking mechanism that can be released by simple actuation at the proximal handle. The penetrating component has two arms that are tapered to allow for easy penetration through the soft tissue to be plicated. By fully engaging the deployment device jaws, the two-piece clip device will lock into position, plicating the tissue together. The clip device is then released from the deployment device and deployment device withdrawn from the site. The deployment device can be reloaded with an additional clip device and subsequent plication performed using the methods described above.

The exemplary clip shown in FIG. 11 shows the plication clip oriented perpendicular to the axis of the plication clamp such that the penetration sites of the clip are parallel to the capsule plane. It should be noted that the plication clip can alternatively be oriented along the plication clamp axis such that the penetration sites are perpendicular to the capsular plane and are oriented vertical along the plicated tissue fold. Further, the plication clamp jaws can be curved (or rotatable as described above) and the plication clip oriented along this curved axis such that the penetration sites are located parallel to the capsule plane. The plication clip embodiment in FIG. 11 is shown with two clip penetration sites through the folded tissue. It should be noted that as few as a single penetration site and up to as many as 6 or more penetration sites can be incorporated into a single plication clip. Similarly, in FIG. 23 an alternative embodiment is shown with a different grasping mechanism 2330, but with plication clips 2311 oriented perpendicular to the axis of the plication clamp. FIG. 24 shows a variation in the distal tip embodiment with the plication clip embedded in the jaws of the device. Dimensions of the device shown in FIG. 24 will accommodate the dimensions required for clinical device delivery and tissue fold plication.

FIGS. 11A to 11H show an exemplary plication clip supported at the distal tip of the deployment jaws. It should be noted that various one-piece and two-piece clip device embodiments can be used to plicate the soft tissue and are described in the subsequent Figure descriptions. Moreover, although FIGS. 10 and 11 depict the centerline grasper having two arms, various embodiments may have additional arms or even as few as one arm. The various embodiments for grasping tissue and pulling the tissues into the deployment device jaws are described in subsequent Figure descriptions. It is important to note that in some instances the centerline grasping mechanism is not the ideal orientation and off-center grasping methods are preferred. In such instances, most of the described grasping embodiments can be adapted to off-center grasping positions. For example, in the instance where one of the jaws of the deployment device is stationary, an off-center grasping mechanism, with respect to the jaws may be required.

The deployment device shown in FIGS. 10 and 11 shows an embodiment with two articulating jaws, in some embodiments only one articulating jaw may be desirable. In the single articulating jaw instances, either the upper or low jaw will be fixed, while the opposing jaw will have the ability to pivot into the open and closed position (See, for example, FIGS. 16 and 17).

The exemplary deployment device embodiment shown in FIG. 12 shows the distal jaws of the device and in some aspects is similar to that described with respect to FIG. 8. However in this embodiment the suture tips 1212 (which are the penetrating spikes/needles) can be passed between jaws of the device by a locking mechanism located on the opposite jaw. The embodiment in FIG. 12 shows a single suture strand 1220 with two suture tips 1221 and 1222 oriented at the ends of the strands. It should be noted that from 1 to 6 or more suture tips may be utilized and located at any combination of suture ends or segments located along the length of a complete suture strand. For example, three suture tips can be incorporated with two located at the ends of the suture and one at the mid-point between the ends of the suture.

The suture tip transfer mechanism incorporated in the plication clamp jaws can comprise a simple lock-fit/snap fit (as shown in FIG. 12), or can incorporate magnetic components that facilitate passing the suture tips from one clamp jaw to the other. For example, the receiving end of the jaws can be magnetized to attract the suture tip (either complementary magnetized or fabricated from an appropriate metal or alloy) of the opposing side after the jaws have been engaged. Additional embodiments can include receiving ends with bi-leaflet, tri-leaflet, or other multi-leaflet configurations that allow for a frictional lock of the suture tips to hold or capture the suture on the clamping jaw after passing through the tissue fold. These receiving slots can be positioned along the jaw in various orientations and numbers. The slots can span the width of the jaw or have multiple slots in series and parallel along the jaw. Moreover, the edges of the leaflet coaption points can have stress-relieving edges to allow for expansion of the orifice to catch the sutures. In the snap fit, frictional lock or magnetized scenarios, the suture ends would be withdrawn from the site along with the suture tips. The suture ends are retrieved and standard sliding knots are tightened and locked by pulling the free end of the suture and advancing the knot. Alternatively, anchors can be passed over the suture ends to eliminate the need for manually creating and passing knots. In the case of multiple suture tips, the discrete suture ends associated with each tip can be tied together or individually tied to create the desired attachment of the plication.

In the embodiment shown in FIG. 12 the phalanges of the jaws are intended to aid in the agitation of the synovium. Variations of these embodiments include roughed surfaces (e.g., rasp) and spikes 1211 with variable sizes for penetration. These embodiments may be static or can also be actuated both in the open or closed position of the jaws. In one instance, as tissue is withdrawing into the jaws using the grasping mechanism, the tissue would rub along the roughened embodiments or be pulled passed the roughened embodiments to irritate the synovium. In an instance where the roughened surface is actuated, after engagement with the jaws of the device, the phalange roughened area can move relative to the surrounding jaw, resulting in a localized irritation of the synovium.

More specifically, as shown in FIG. 12, various embodiments of the deployment device jaws can include mechanism for roughening, abrading, or penetrating the plicated tissue fold to elicit a biological healing response, as described previously. These embodiments can include mechanical methods such as sharpen needle points, blunt points, rasping elements, or elements which can produce the desired abrasion, roughening, or penetration to elicit the desired biological healing response. These embodiments can also include non-mechanical mechanisms such as thermal, chemical, x-ray, electrical, ultrasonic, ultraviolet light, or microwave signal mechanisms to cause the localized tissue damage to the synovium that would also elicit the biological healing response that is desired.

In the exemplary embodiment shown in FIGS. 13 and 14, the procedural application of a hinged clip device is shown with and without the use of a grasper 1311. The distal end of the deployment device 1300 is shown in FIG. 13 where in (A) a portion 1331 of the ligament tissue 1330 is captured by the grasper mechanism, in (B) pulled into the jaws of the deployment device, in (C) penetrated by the clip device and plicated, and in (D) the deployment device removed. This embodiment is shown to exemplify the stepwise procedure in deploying one of the clip devices 1320. For simplicity, the element for abrading, roughening, penetrating, or exciting the biological healing response of the synovium are not shown, but may be similar to that shown in FIG. 12.

In some embodiments, a surgeon may agitate the synovium with a general rasping arthroscopic instrument in the region of interest prior to positioning of the deployment device and deployment of the plication clip. Furthermore, unlike the embodiment shown in FIGS. 10 and 11, the placement of the clip device is positioned along the jaws of the deployment device, not specifically at the distal tip. The advantage of the placement of this device in this position along the jaw of the deployment device can be appreciated in FIG. 14 where the embodiment shown does not utilize a grasper to draw the tissue into the jaws of the deployment device. In various embodiments of the clip device, hinged or pivoted actuation of the clip may allow for plication of the ligament or soft tissue without the need of the grasper to bring the tissue into position.

In FIGS. 13 and 14 the clip device is snapped into its locked configuration, clip released, and deployment device removed. In FIG. 13 the level of plication would be dictated by position (e.g., pull back) of the grasping mechanism. With this hinged embodiment, the limitation to the plication length will be limited to the size of the clip design. Specifically, as shown in FIG. 13D, the clip device will surround the area of plication. Noting that in the embodiment shown, the centerline grasper and the jaws of the deployment device may be off-set from each other. Specifically, certain embodiments, if within the jaws of the deployment device, may require the grasper to be stacked either adjacent of the jaws or on one side of the jaws (non-center).

As shown in FIGS. 13 and 14, there may be instances where the general capsular volume or excessive laxity will allow for plication of the tissue fold without the need for a grasper to bring the tissues into position. In such instances a simplified plication deployment device may prove to be advantageous. However, it is anticipated that the advantage gained with respect to adjustment in the length of plication, alignment and drawing of the tissue into the deployment device jaws may dictate the need for a grasping mechanism. As indicated previously, the length of plication of this hinged embodiment will be limited to the size of the clip device. However, other embodiments (as described elsewhere in this disclosure) will not have these sizing limitations. The primary emphasis of FIG. 14 is to demonstrate that the clip designs themselves can act as jaws that can grasp tissue without the need of a dedicated grasping mechanism.

Figure 15A:
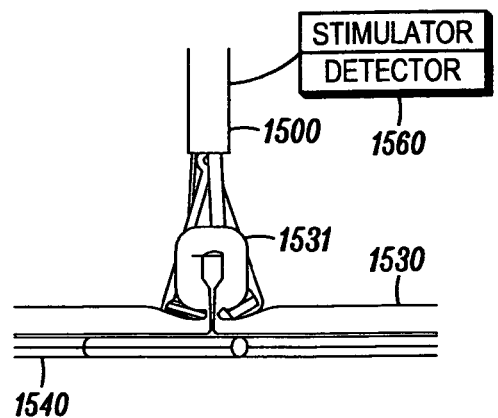
FIGS. 15A to 15C show a procedural use of a neurostimulator to verify the position of the axillary nerve relative to the area of plication according to an exemplary embodiment of the present invention.
Figure 15B:
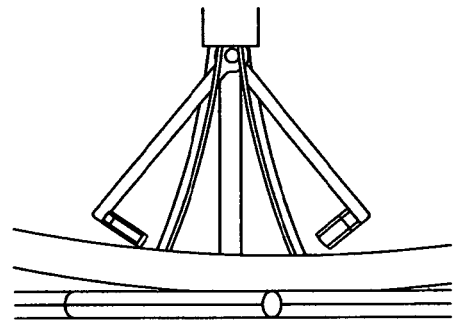
Figure 15C:
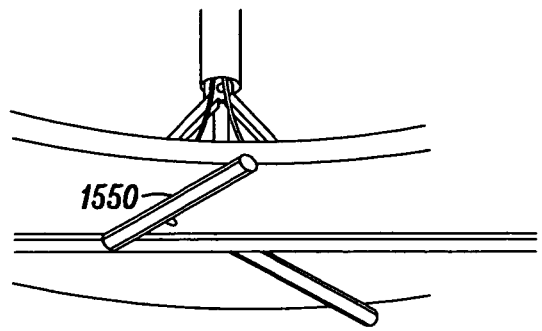

The embodiment shown in FIG. 15 shows the use of neuro-stimulation as a verification tool indicating the proximity of neurovascular structures, in particular the axillary nerve 1540. Similar neuro-stimulation application can be applied to some of the exemplary embodiments, for example the devices shown in FIGS. 23-33. Hence, the delivery and suture plication devices shown in FIGS. 23-33 can contain a centralized or non-centralized grasping element that can carry the neuro-stimulating signal to allow for verification of the proximity of neurovascular structures, in particular the axillary nerve. As discussed earlier, the position of the axillary nerve relative to the inferior capsule is within approximately 1 cm. The close proximity of this nerve raises concerns when applying any plication method to the capsule. An exemplary embodiment of the deployment device includes the incorporation of a neuro-stimulation probe to excite the region of plication prior to engagement of the plication clip. The probe element can comprise either the grasping mechanism and/or the deployment device jaw. An external energy source capable of delivering pacing stimuli having an amplitude from 0.1 mA to 50 mA is connected to the probe element 1550 and stimulator/detector 1560 (e.g., the grasper, plication clamp jaws, or independent electrode probe) to transmit the electrical stimulation to the capsular tissue in direct proximity to the grasper and/or plication clamp.

Activation of the axillary nerve 1540 (or other nerve or muscle tissue) would be caused if the grasper or plication clamp jaw is too close to the axillary nerve (or other nerve or muscle tissue). Activated response would be observed by twitching of muscles associated with the neurovascular structure. For example, activation of the axillary nerve will result in a muscle response from the deltoid muscles. The intended neuro-stimulation is intended to provide minimal excitation for positional identification only, not for diagnostic or treatment purposes.

Stimulation of the axillary nerve (or other nerve or muscle tissue) provides a clear warning that the grasper and/or plication clamp jaws are at risk of damaging the axillary nerve and indicates the physician should move the plication device to another location, thereby avoiding unwanted nerve (or muscle) damage.

Commercially available stimulators can be utilized to delivery the 0.1 mA to 50 mA pacing pulse. The waveform can be monophasic, biphasic, or other pattern known to evoke stimulation of nerve or muscle tissue. The pulse duration can vary between 1 msec to 500 msec. The amplitude determines the proximity of the probe element to the stimulated nerve or muscle. For example, a plication device that stimulates the axillary nerve by delivering a biphasic pacing pulse having a duration of 10 msec and an amplitude of 1 mA is closer to the axillary nerve than a plication device that requires 10 mA to stimulate the axillary nerve with the waveform and duration being the same. As such, the proximity of the axillary nerve can be determined by the amplitude of the pacing pulse thereby ensuring that plication does not damage the axillary nerve (or other nerve or muscle), and/or mapping the location of the axillary nerve to plan the location of tissue plications.

Although the exemplary embodiment of the invention as shown in FIG. 15 is described with respect to the shoulder capsule and the axillary nerve, one having ordinary skill in the art would be cognizant that the same technique may be applied to other tissues or tissue systems having other nerves passing therethrough.

Figure 16A:
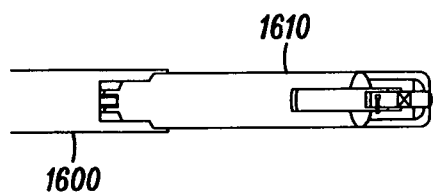
FIGS. 16A to 16C show a top, side and prospective views of a deployment device containing a single armed anchoring device and a suture retrieval mechanism according to an exemplary embodiment of the present invention.
Figure 16B:
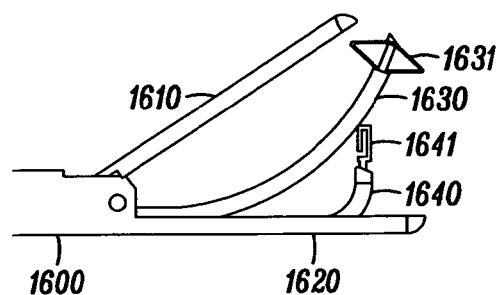
Figure 16C:
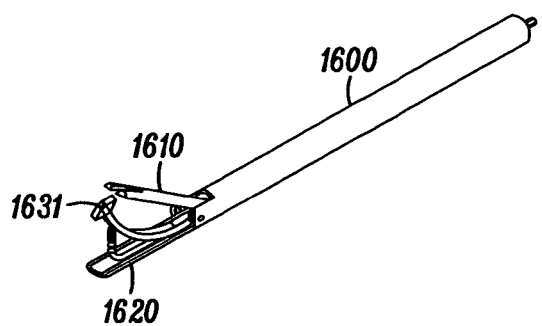

The exemplary embodiments shown in FIGS. 16 and 17 illustrate a device that has a grasper mechanism 1631, a suture retrieving mechanism 1641, and a jaw mechanism 1610. This device configuration has a hinged distal jaw 1610 with one jaw 1620 in a fixed configuration. Similar to previously described grasper mechanisms, this single armed grasper is shown in a deformed configuration, but can also be oriented into any angular position (including a straight configuration) by pre-deforming the grasper shaft. The grasper embodiment shown includes two primary components: an exterior guiding tube 1630 and an interior deployment anchor 1631. The anchor 1631 begins within the guiding tube sheet in an undeployed/low profile configuration. The distal tip of the anchor 1631 is tapered to allow for penetration through soft tissue layers. The surface of the guiding tube 1630 is smooth or can be lubricated or coated (e.g., hydrophilic coatings) to allow for easy penetration and passage through tissues.

The guiding tube 1631 can be advanced beyond the jaws as illustrated in FIG. 17A. After penetration of the anchor 1631 and guiding tube through the tissue layers 1650, deployment/advancement of the anchor and subsequently deployment of the anchor wings (to prevent pull out) is performed. Once anchor 1631 is fully deployed, the grasping mechanism is drawn back into the jaw of the device, pulling a tissue fold 1651 into the jaws. Once the grasping mechanism is withdrawn, the jaws are engaged. The suture retrieving mechanism also includes two components: an outer guiding tube 1640 and an inner suture grabber 1641. During engagement of the jaws, the outer guiding tube 1640 penetrates the folded tissue 1651. Once fully engaged, the suture grabber 1641 is deployed.

Once the suture is engaged, the jaws are released, and suture pulled through the tissue layers. The grasping mechanism may be maintained in position or released depending on the surgeon's preference. In some instances, the surgeon may elect to keep the grasping mechanism in position to maintain the tissue pleat until final plication is finished. Repeated passing of the suture is performed and knots tied to secure the region of plication. Coordinated movements of the jaws and deployment of the suture grabber add to the simplicity of the device embodiment. Various embodiments can be included in the jaws of this deployment device embodiment to accommodate the use of clip devices at the distal tip, as exemplified in FIGS. 10 and 11.

The anchor wings may be made from metals, shape memory metals, polymers and shape memory polymers that can be deployed and retraced into the guiding tube. The shape of the wing deployment can vary (e.g., elliptical, spherical, triangular, corkscrew, hook). The primary purpose of the wing shape is to provide an anchoring point to pull the tissue into the grasper. Other embodiments of the anchor deployment may also include inflation of balloon anchors of various configurations and materials (e.g., silicone, polyurethane, PET, Nylon, etc.). An advantage of the single armed grasping embodiment is the ability to leave the device engaged while releasing and rotating the overall device. This motion is allowable because of the wing shape or balloon tip anchoring mechanism, which is does not actively grasp the tissue as shown in FIGS. 10 and 11.

An embodiment of the deployment device has a total length (including the actuating handle) to be about 20-100 cm with the shaft of the device being about 12-92 cm of the length. The range in maximal width or maximum diameter of the shaft and working end of the device will range between 4.0 to 8.0 mm. The length of the deployment device jaws will range from 10 to 40 mm in length.

Grasper embodiments 1800 and 1900 shown in FIGS. 18 and 19 depict variations of the grasping mechanism described for other embodiments, such as those shown in FIGS. 3 and 4. Engaged and unengaged illustrations are shown for two pronged and three pronged embodiments. As indicated in the figures, the ends 1810 and 1910 of the grasper embodiment can include tips 1820 and 1920 that are triangular in shape or another similar tooth-like structure that would allow for gripping or engaging of soft tissues when engaged. These tips could also include reverse hook configurations (similar shape to knitting needles). Additional embodiments that include additional prongs can also be included as well as an embodiment containing only one arm. The single armed embodiment will include a similar distal tip that can hook and engage soft tissues, allowing for grasping and drawing of the device into the jaws of the deployment device.

Grasper embodiments 2000, 2100 and 2200 shown in FIGS. 20, 21 and 22 depict variations of a single armed grasping mechanism using an anchoring system. In addition to the embodiment described in FIGS. 16 and 17, the embodiments shown in FIGS. 20, 21, and 22 show a method for grasping tissue using a deployed anchoring system. In FIG. 20 the undeployed grasper is held within the guiding tube. The distal tips 2010, 2110 and 2210 of the grasper embodiments are a tapered or sharpened point that allow for tissue penetration. The shaft of the guiding tube as well as the grasper device are polished or coated to allow for easy passage through tissues. The diameter size of these devices can range from 0.5 to 3.0 mm. Once the grasper penetrates the tissue layers, the grasper is advanced beyond the guiding tube to allow for deployment of the anchor. The embodiments shown are hook and corkscrew configurations; however, the shape and deployment can vary as described for FIGS. 16 and 17. The materials used to accommodate these distal configuration changes can include shape memory metals/polymers or other specified metals or polymer materials. An advantage of these embodiments is the ability to adjust the shape to make the device more compatible with surrounding structures (e.g., axillary nerve) as well as improve the ability to adequately grasp the tissue and pull the tissue into the jaws of the deployment device.

Alternative graspers include balloons incorporated at the distal tip of a central tube that can be expanded once positioned through or into the capsular tissue. The balloon can be oriented proximal to a needle or can incorporate a central lumen such that a separate needle can pass. Alternatively, a tube coupled to a vacuum source can be used as the grasper such that as suction is applied through the tube the tissue is pulled into engagement with the tube and can be manipulated by the vacuum grasper. To augment the vacuum grasper, a flexible flange can be incorporated to enlarge the vacuum orifice and better secure the vacuum grasper to the tissue surface. This flange can solely comprise a flexible silicone or polyurethane membrane (or other flexible polymer) or can incorporate strips of support material formed in an outward fashion and covered by a flexible membrane. The strips expand the flexible membrane outward as they are released from the confines of the guiding tubes and compress the flexible membrane as they are retracted into the guiding tubes. The enlarged opening increases the surface area of tissue that is contacted by the vacuum grasper increasing the grasping force.

The grasper embodiments shown can be connected to an external simulator for neuro-stimulation to verify the location and position of the plication relative to neurovascular structures (e.g., axillary nerve), in a similar way as that shown for FIG. 15. Once the plication has been effected, the grasper anchor is released from engagement to the plicated tissue and is drawn back into the guiding tube. The low profile and simplicity of deploying these anchors to grasp tissue provides a mechanism that is reproducible, can have a secondary function of irritating the synovium (eliciting a biological healing response) by penetrating the tissue layer in local proximity to the plication, and provide a sturdy anchoring system that the surgeon can pull back the tissue pleat into the jaws of the deployment device.

Figure 23:
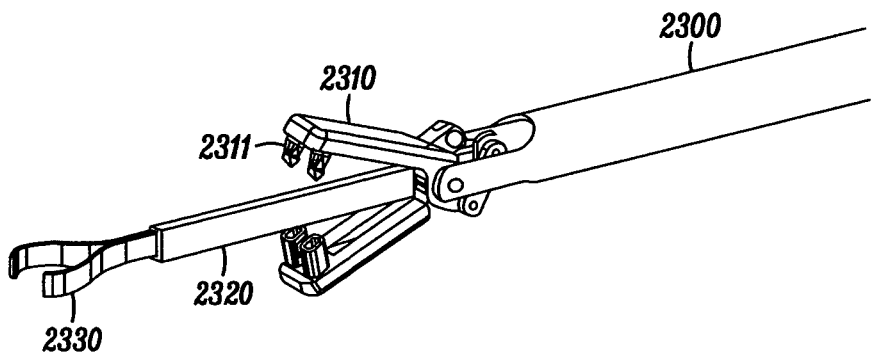
FIG. 23 shows a distal tip and shaft of a plication deployment device according to an exemplary embodiment of the present invention.
Figure 24A:
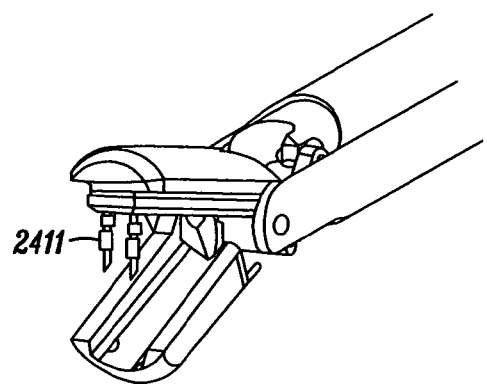
FIGS. 24A to 24B show an embodiment of a distal tip and shaft of a plication deployment device according to an exemplary embodiment of the present invention.
Figure 24B:
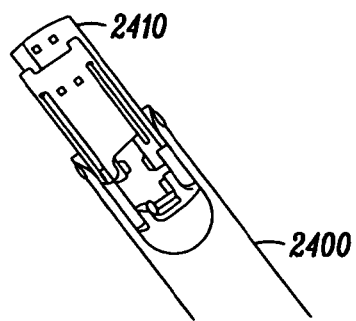
Figure 25A:
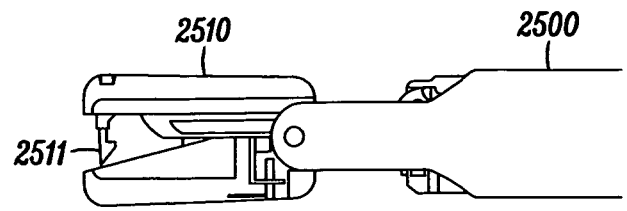
FIGS. 25A to 25C show an embodiment of a distal tip and shaft of a plication deployment device according to an exemplary embodiment of the present invention: (a) from the side; (b) view from bottom jaw looking toward top jaw; and (c) a perspective view.
Figure 25B:
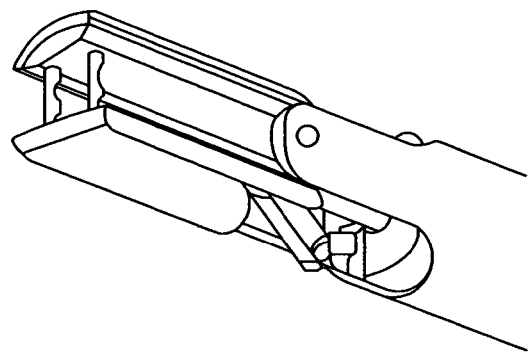
Figure 25C:
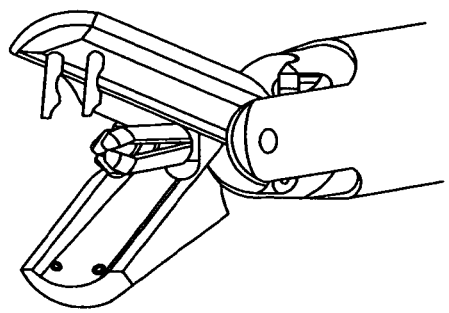

Grasper embodiment 2300 shown in FIG. 23 depicts a variation in the grasping mechanism with an outer sleeve in which an inner element with a pre-shaped distal tip 2330 is located. The purpose of the pre-shaped distal tip is that it can be drawn by shaft 2320 into the outer sleeve to close the jaws 2310 of the grasper. This mechanism provides the ability to advance and withdraw the grasper independent of the closing of the jaws.

In FIG. 23 an alternative embodiment is shown with a grasping mechanism with plication clips 2311 oriented perpendicular to the axis of the plication clamp. FIG. 24 shows a variation in the distal tip embodiment with the plication clip 2411 embedded in the jaws of the device. Dimensions of the device shown in FIG. 43 will accommodate the dimensions required for clinical device delivery and tissue fold plication.

Figure 26:
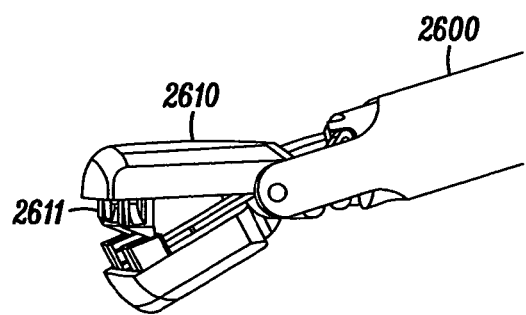
FIG. 26 shows a distal tip and shaft of a plication deployment device according to an exemplary embodiment of the present invention.
Figure 29A:
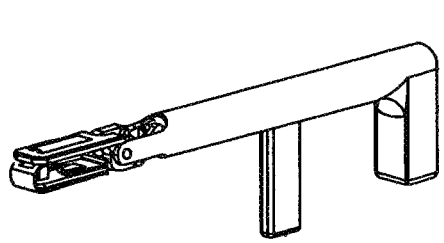
FIGS. 29A to 29F show a plication delivery device according to an exemplary embodiment of the present invention with a distal tip in the closed and open positions and a bottom flange having a flexible member that may be displaced to expose a penetrating element.
Figure 29B:
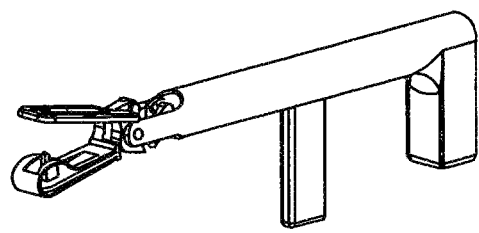
Figure 29C:
Figure 29D:
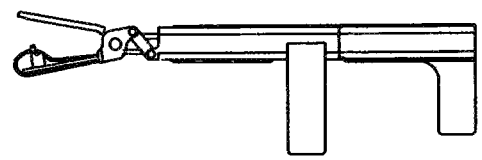
Figure 29E:
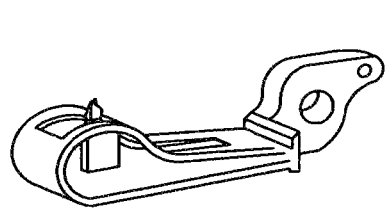
Figure 29F:
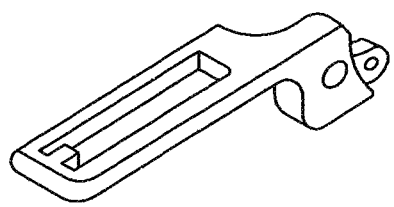
Figure 31A:
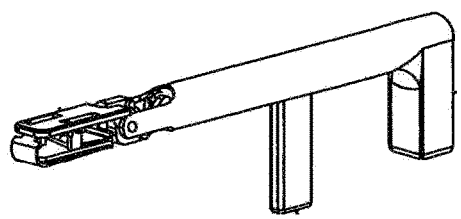
FIGS. 31A to 31D show a plication delivery device according to an exemplary embodiment of the present invention with a distal tip in the closed and open positions and a bottom flange having a flexible member that may be displaced to expose a penetrating element.
Figure 31B:
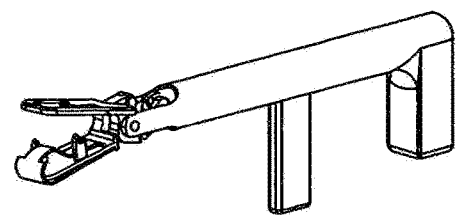
Figure 31C:
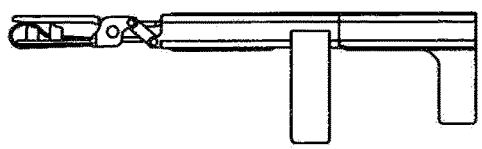
Figure 31D:
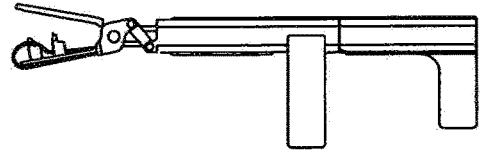

FIGS. 25A to 25C and FIG. 26 show exemplary embodiments 2500 and 2600 of a distal tip of a suture delivery device intended for the same purposes and functions as described for the embodiments in FIGS. 4-9. The grasping embodiment shown in FIG. 26 can be substituted with any of the grasping embodiments presented within this disclosure. The penetrating suture elements can be one or greater in number. In FIGS. 25 and 26, two suture penetrating elements are shown as 2511 and 2611 within jaws 2510 and 2610. In these embodiments the suture is held on one side of the jaw and the penetrating elements on the opposite jaw. The suture side holds the suture in a manner that allows for engagement of the penetrating elements to catch the suture and during engagement and pull the suture back through the tissue fold when released. The suture can be freely advanced through the tissue fold during withdrawal of the device. It should be noted that 1 to, for example, 6 suture tips oriented at the ends of the strands and located at any combination of suture ends or segments located along the length of the complete suture strand. For example, three suture tips can be incorporated with two located at the ends of the suture and one at the mid-point between the ends of the suture. The suture side of the jaw can be removable and replaceable for use as a cartridge for additional sutures.

In various embodiments, different suture lengths can be incorporated to allow for delivery of one or more suture plications. The penetrating suture tips can have a variety of embodiments that allow for catching of the suture. As shown in FIG. 26, the penetrating element 2611 can have a hook edge along the axis that allow for capture of the suture as it passes through the suture holding side of the jaw. The shape and geometry of the hook edge is inverted as to minimize the potential for catching on tissue during the withdrawal of the penetrating elements while enabling capture of the suture for withdrawal. Additional embodiments of these suture tips can include variations that have flexible latches that cover the hook edge and allow for capture of the suture as well as securing of the suture while providing a smooth transition along the penetrating element axis (reducing the potential for catching of the tissue during withdrawal). Other embodiments can include deeper and more curved J-hooked edges that have smooth edges and allow for capture of the suture while reducing the possibility of tissue catching during withdrawal. Once the suture end is captured and retrieved, standard sliding knots are tightened and locked by pulling the free end of the suture and advancing the knot. Alternatively, anchors can be passed over the suture ends to eliminate the need for manually creating and passing knots.

Similar to previously described embodiments, the jaws of the device can also incorporate roughed surfaces (e.g., rasp) and spikes with variable sizes for penetration. These embodiments may be static or can also be actuated both in the open or closed position of the jaws. In one instance, as tissue is withdrawing into the jaws using the grasping mechanism, the tissue would rub along the roughened embodiments or be pulled passed the roughened embodiments to irritate the synovium. In another instance, after engagement of the jaws, the device will penetrate the tissue, resulting in localized irritation of the synovium along distinct roughened or spiked locations along the flange of the jaw.

In addition, similar to that described for the embodiment shown in FIG. 15, neuro-stimulation can be added to these device tips either through the grasping mechanism or through the penetrating elements. The primary purpose would be for verification of the proximity of neurovascular structures, in particular the axillary nerve.

FIGS. 27-31 show various alternative embodiments of the distal tip of a suture plication delivery device. As shown, single or multiple sutures can be passed at the device tip in various orientations. Not shown, but included in these embodiments is a central or non-central grasping mechanism. Any of the grasping mechanisms described for the devices in this document can be utilized in this embodiment. Similarly, as described for the embodiment shown in FIG. 15, neuro-stimulation can be added to these device tips either through the grasping mechanism or through the penetrating elements. A primary purpose would be for verification of the proximity of neurovascular structures, in particular the axillary nerve.

A purpose of presenting FIGS. 27-31 is to demonstrate various non-limiting distal tip embodiments for suture passing where one side of the jaw holds the suture and the opposite side has the penetrating and suture capture element. Similar to that described in FIGS. 25 and 26, the suture side holds the suture in a manner that allows for engagement of the penetrating elements to catch the suture and during engagement and pull the suture back through the tissue fold when released. The suture can be freely advanced through the tissue fold during withdrawal of the device. It should be noted that 1 to, for example, 6 suture tips may be oriented at the ends of the strands and located at any combination of suture ends or segments located along the length of the complete suture strand. For example, three suture tips can be incorporated with two located at the ends of the suture and one at the mid-point between the ends of the suture.

The suture side of the jaw can be removable and replaceable for use as a cartridge for additional sutures. In various embodiments, different suture lengths can be incorporated to allow for delivery of one or more suture plications. The penetrating suture tips can have a variety of embodiments that allow for catching of the suture. As shown in FIG. 27-31, the penetrating element can have a hook edge along the axis that allow for capture of the suture as it passes through the suture holding side of the jaw. The shape and geometry of the hook edge is inverted as to minimize the potential for catching on tissue during the withdrawal of the penetrating elements while enabling capture of the suture for withdrawal. Additional embodiments of these suture tips can include variations that have flexible latches that cover the hook edge and allow for capture of the suture as well as securing of the suture while providing a smooth transition along the penetrating element axis (reducing the potential for catching of the tissue during withdrawal). Other embodiments can include deeper and more curved J-hooked edges that have smooth edges and allow for capture of the suture while reducing the possibility of tissue catching during withdrawal. Once the suture end is captured and retrieved, standard sliding knots are tightened and locked by pulling the free end of the suture and advancing the knot. Alternatively, anchors can be passed over the suture ends to eliminate the need for manually creating and passing knots.

An additional element shown with the exemplary embodiments in FIGS. 27-31 is a flexible cantilever, flexible bow, or guard on the penetrating element flange that allows the opposing flange to rest without engagement of the suture and the penetrating element. In this resting position, the device can be introduced through a standard 5, 6, or 8 mm cannula without engagement.

Various embodiments show that different shapes and configuration with variable numbers of penetrating elements and position of penetrating elements can be chosen and not limited to those shown in FIGS. 27-31. A common element of these embodiments is the ability to engage the suture and penetrating element by further engaging the jaws. The additional engagement, achieved by closing the jaws by applying additional pressure, will result in deformation, bending, or shifting of the cantilever, flexible bow, or guard to expose the penetrating element. The exposure of the penetrating element allows for penetration of through the tissue fold and engagement of the element with the suture. The subsequent opening of the jaw results in pulling of the suture back through the tissue fold and return of the cantilever, flexible bow, or guard to its original position.

Similar to previously described embodiments, the jaws of the device can also incorporate roughed surfaces (e.g., rasp) and spikes with variable sizes for penetration. These embodiments may be static or can also be actuated both in the open or closed position of the jaws. For example, as tissue is withdrawing into the jaws using the grasping mechanism, the tissue would rub along the roughened embodiments or be pulled passed the roughened embodiments to irritate the synovium. In another example, after engagement of the jaws, the device will penetrate the tissue, resulting in localized irritation of the synovium along distinct roughened or spiked locations along the flange of the jaw.

In addition, similar to that described for the embodiment shown in FIG. 15, neuro-stimulation can be added to these device tips either through the grasping mechanism or through the penetrating elements. A primary purpose would be for verification of the proximity of neurovascular structures, in particular the axillary nerve.

Figure 32:
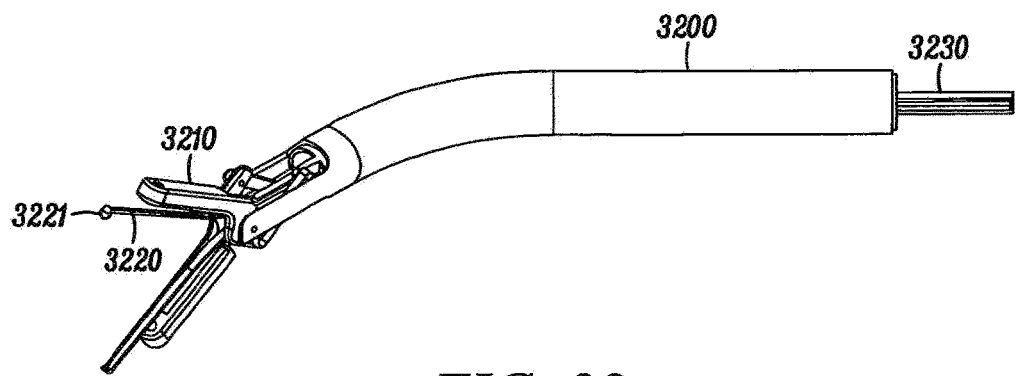
FIG. 32 shows a flexible delivery device shaft according to an exemplary embodiment of the present invention to allow for approaching plication surface at various angles.

The exemplary embodiment in FIG. 32 shows a repair device 3200 having a flexible shaft to allow for insertion, movement and manipulation through contoured body geometry to access the necessary target tissue. An internal slide mechanism 3230 allows for manual or automated manipulation of the jaws 3210 to allow the gripper 3220 to pierce the penetrating point 3221 into the target tissue. An abraded surface and/or neuro-stimulator may also be added to this exemplary embodiment to enhance the tissue repair process and nerve avoidance, respectively.

Figure 33A:
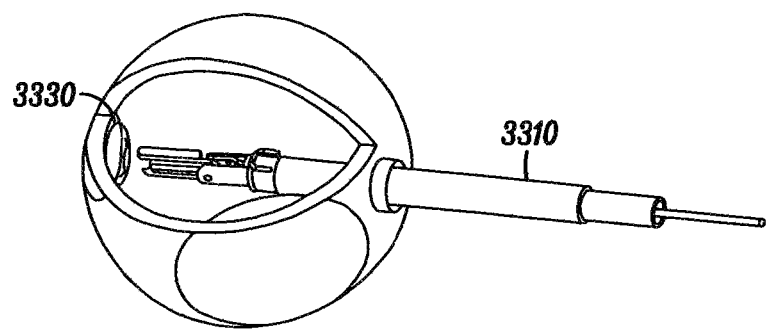
FIGS. 33A and 33B show an internal capsular plication according to an exemplary embodiment of the present invention by grasping the tissue and sliding a plicating clip over the tissue fold and the final plication with clip in position.
Figure 33B:
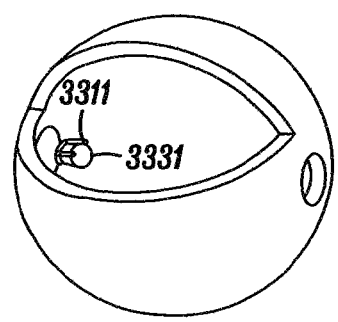
Figure 34A:
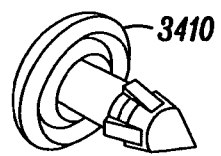
FIGS. 34A to 34D show perspective, top, and side views of a two component plication device according to an exemplary embodiment of the present invention that contains a single point of penetration.
Figure 34B:
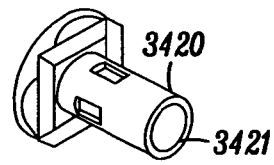
Figure 34C:
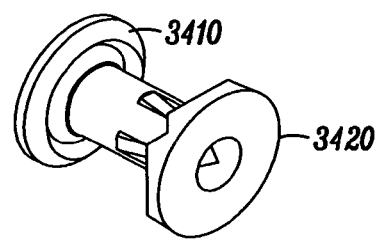
Figure 34D:
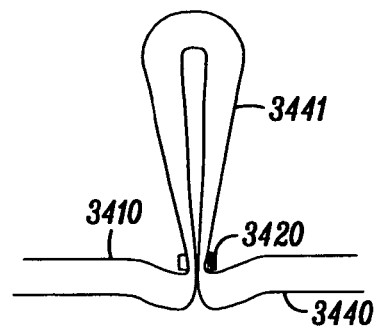

FIG. 33 illustrates another exemplary embodiment of the delivery device in which the plicating suture or clip is delivered over the outside of the device shaft. In this embodiment, the tissue 3330 is grabbed to form the tissue fold 3331. Then the plication suture or clip is advanced down the shaft of the device. Once in position, the tissue is released. The suture element can be a pre-tied embodiment or an elastic band embodiment. The plication clip can be of the forms shown in FIGS. 43 and 44.

Various plication devices were disclosed by example within the exemplary embodiments described above. Such plication devices may have a number of different shapes and sizes, which are all within the scope of the present disclosure. Various specific shapes and sizes will be discussed herein but the present invention is not limited to such exemplary embodiments.

The exemplary embodiment shown in FIG. 34 depicts a plication clip device that includes a penetrating base 3410 and a locking base 3420. The overall device shown is circular in cross-section as an example. However this cross section could also be square, rectangular, triangular, or any other geometric cross-section. The penetrating base 3410 of the clip device has a distal tip that is sharpened or tapered to allow for easy passage through tissue 3440. Just below the distal tip are multiple protruding tapered, outwardly extending locking elements that mate with corresponding holes 3421 on the locking base 3420. The number of locking elements can range from 1 to, for example, 6. When engaged together, the plication clip locks into position, securing the tissue pleat 3441. This embodiment or variation can be delivered through plication clamps described above.

The embodiment shown in FIG. 35 depicts a two-component plication clip system having a dual arm penetrating tubular U-shaped component 3510 and a locking base 3520. Both ends of the penetrating component are tapered to allow for easy penetration through soft tissue. In addition, locking tabs are positioned at the distal tips and extend outward for mating and securing of the U-shaped component to the locking base. The locking base 3520 has two sets of through-holes 3521 for the U-shaped component to engage and lock to the base. The bottom set of through-holes are smaller in diameter to allow for seating of the distal tips of the U-shaped component, but does not allow the device to slip through. The width of the device can range from 2 to 30 mm; and more specifically from 2 to 10 mm. The height of the device can range from 2 to 20 mm; and more specifically 2 to 6 mm. The thickness of the device clip members can range from 0.25 mm to 3 mm.

The embodiment shown in FIG. 36 depicts a three-component plication clip system: a dual arm penetrating tubular U-shaped component 3610, an outer covering for the U-shaped component 3611, and a locking base 3620. Both ends of the penetrating component are tapered to allow for easy penetration through soft tissue. The locking tabs are positioned at the distal tips for mating and securing of the U-shaped component to the locking base. These locking tabs are tapered to allow for easy sliding into the holes 3621 of the locking base. The locking base has two sets of through-holes 3621 for the U-shaped component to engage and lock with the base. The holes in the locking base have tapered and shaped holes, such as the star shaped holes used in the figure, that allow for easy engagement of the lock mechanism. The bottom of the locking base includes through-holes for the U-shaped distal tips to seat, but does not allow the device to slip through the locking base.

The outer covering can be fabricated form a resorbable material or a polymer such as polypropylene or other suture materials to cover the central support that can be fabricated from a metal or alloy, or a polymer with sufficient structural properties to engage the locking base and prevent release of the two components once engaged. The width of the device can range from 2 to 30 mm; more specifically from 2 to 10 mm. The height of the device can range from 2 to 20 mm; more specifically 2 to 6 mm. The thickness of the device components can range from 0.25 to 3 mm.

Figure 37A:
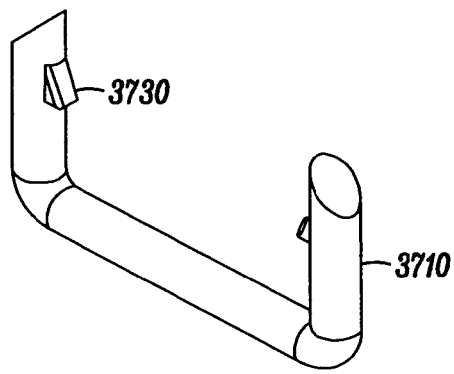
FIGS. 37A to 37C show perspective, top, and side views of a two component plication device according to an exemplary embodiment of the present invention that has two points of penetration, extending the region of attachment and distributing the stresses on the device.
Figure 37B:
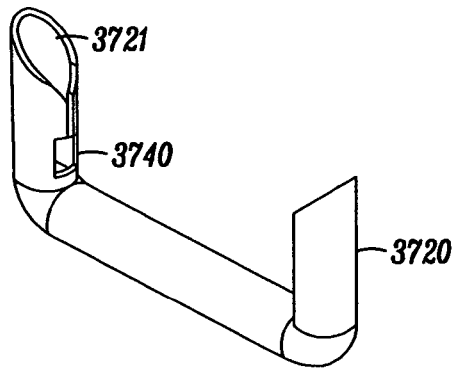
Figure 37C:
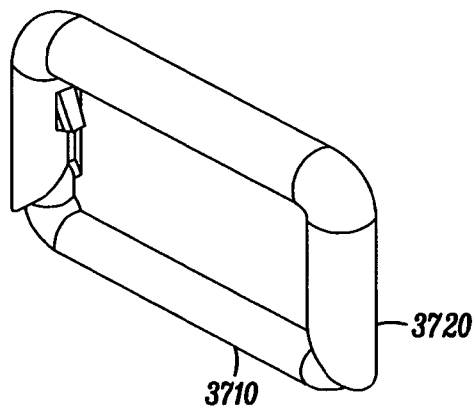
Figure 38A:
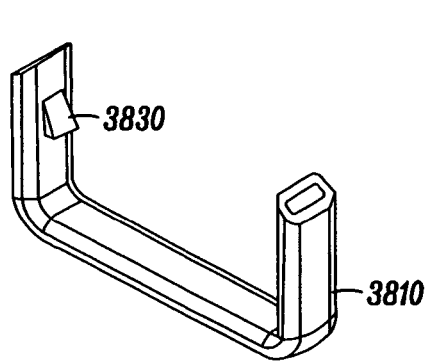
FIGS. 38A to 38E show perspective, top, and side views of a two component plication device according to an exemplary embodiment of the present invention that has two points of penetration, extending the region of attachment and distributing the stresses on the device.
Figure 38B:
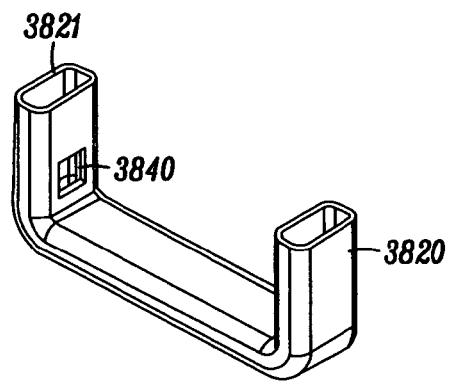
Figure 38C:
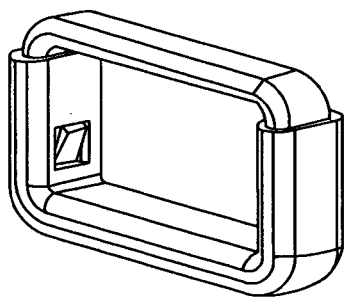
Figure 38D:
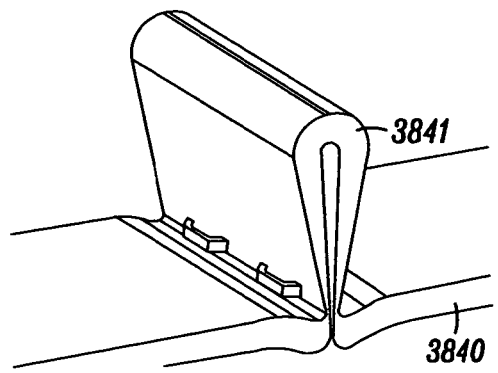
Figure 38E:
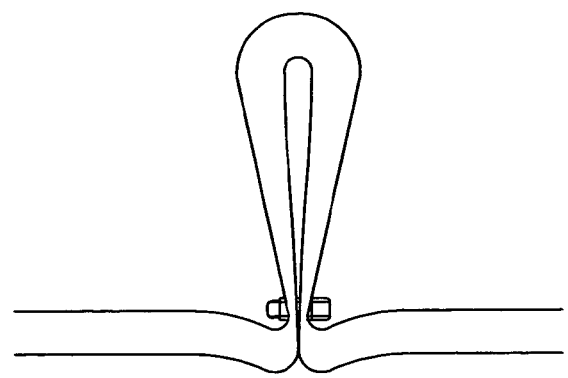

The embodiments 3710 and 3810 shown in FIGS. 37 and 38 depict two-component plication clip systems having a dual arm 3720/3721 and 3820/3821 penetrating tubular U-shaped component and a dual arm tubular locking base. Various embodiments of these devices can include circular, rectangular, square, or other geometric cross-sections. Both ends of the penetrating component are tapered/sharpened to allow for easy penetration through soft tissue. Alternatively, one end can be blunt while the other end sharpened. The locking tabs, extending outwardly, are positioned near the distal tips for mating and securing of the U-shaped components to the locking bases. In each embodiment, the penetrating component slides into the locking base arms and tabs securely lock the devices together when engaged together.

The embodiment in FIG. 37 incorporates a rigid tab 3730 that extends outwardly with a locking component that incorporates a slot 3740 from the distal tip to the locking opening. This allows radial expansion of the base around the locking tab 3730 until the locking tab is situated in the opening where the base returns to its original shape locking the tab within the opening. The embodiment in FIG. 37 can be fabricated completely from polymers (e.g., polypropylene, other suture material, or other biocompatible polymer) since the tab of the base does not need to deflect and spring back to its preformed shape but can be rigid since the larger diameter lock expands during engagement of the two components.

The embodiment in FIG. 38 incorporates an outwardly extending tab 3830 to the clip base that engages an opening 3840 in the clip lock. As such the tab 3830 must deflect during insertion of the base into the lock and return to its original orientation once positioned within the opening of the lock to secure the base to the lock. As such, the tab must incorporate enough spring such that the thin member can deflect and return once the confining forces are removed, commiserate with placing the tabs into the opening of the clip lock. In this embodiment the base can comprise a metal tube cut and formed into the illustrated shape or short metal inserts that are insert molded inside a polymer to reduce the surface area and volume of metal incorporated in the device thereby reducing the radiopacity. Alternatively, the base can comprise a polymer with sufficient thickness and rigidity to define a hinge over which the tab can flex and define enough of a spring constant to engage the opening of the clip lock once positioned into engagement.

The embodiments in FIGS. 37 and 38 penetrate both the base and lock into the plicated tissue thereby reducing the height of each component (base and lock) from the crossbar to the distal tip. As such, the profile of the clip on the deployment device is reduced and the locking point is positioned within the plicated tissue. The width of the device can range from 2 to 30 mm; more specifically 2 to 10 mm. The height of the device can range from 2 to 20 mm; more specifically 2 to 7 mm. The thickness of the device components can range from 0.25 to 3 mm.

Figure 39A:
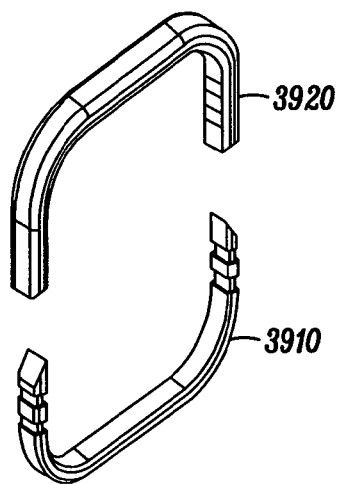
FIGS. 39A to 39C show perspective views of a two component plication device according to an exemplary embodiment of the present invention that includes two locking positions.
Figure 39B:
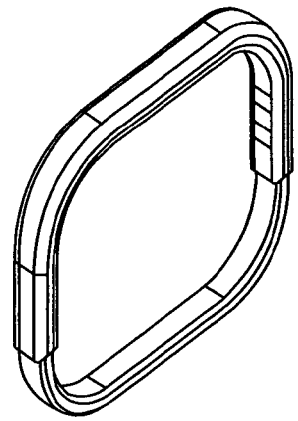
Figure 39C:
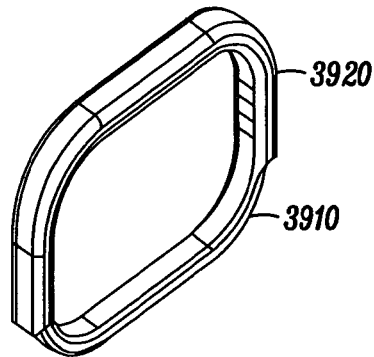

FIG. 39 depicts an alternative embodiment that can be incorporated in any of the U-shaped components which have a multiple stage locking mechanism. The purpose of the multiple stage locking mechanism is to provide a method to increase the tightness of the plication. Although this embodiment shows only two stages or components 3910 and 3920 of locking, the number of locking stages or components can be increased until full engagement or overlap of the cross bars is achieved.

Similarly, the embodiment shown in FIG. 41 shows a two-component plication clip system with penetrating elements 4111 on each component 4110. Opposing sides of the components have tapered penetrating components 4111 to allow for easy penetration though soft tissue. In addition, locking tabs 4112 are positioned at the distal tips of the penetrating elements for mating and securing of the U-shaped components to engage the opposing base. Two positions of locking are demonstrated in the illustrations; however in other embodiments the number of positions can be increased. Moreover, the distance between each locking point is adjustable from 0.001 mm to 1.0 cm. A purpose of the multiple stage locking mechanism is to provide a method to increase the tightness of the plication. The width of the device can range from 2 to 6 mm. The height of the device can range from 2 to 5 mm. The thickness of the device can range from 1 to 3 mm.

The exemplary embodiment shown in FIG. 40 presents a U-shaped plication clip device with a hinge attachment 4030 that the device pivots around. The hinge is shown as a pivoting mechanism. Alternatively a flexible hinge inherent to an integrated, unitary device can be utilized. One end 4010 of the clip device has a distal tip that is tapered to allow for tissue penetration while the proximal end 4020 is bevel shaped to accept the distal tip. As shown, the distal tip 4010 of the device has a locking region 4040 that inserts and engages the proximal end. Other embodiments of this clip can include variations on the hinge mechanism, variations in cross-sectional geometry (e.g., circular, rectangular, square and other geometric shapes), and variations in height, width, and length of the device.

Another embodiment is shown in FIG. 42 as a U-shaped repair clip device that can be used with and without a pledget element 4220, shown in FIG. 42C. In the deformed delivery position 4210, FIG. 42A, the clip device can be delivered through the tissue using an introducer deployment mechanism (e.g., dual tapered needles) or tapering of the clip feet. In the undeformed position 4211, FIG. 42B, the clip device engages the tissue by deploying feet anchors 4213, as shown in FIG. 42F. Another embodiment of this includes the use of a backing or pledget component 4220 that is used as the locking base of the clip device. The clip device would be deployed as above, however, the locking base would be used to insure adequate locking of the tissue. The locking base would be supported by one jaw of the plication clamp while the deformed clip is advanced through the tissue and through openings in the locking base with the second jaw of the plication clamp. Once positioned, the clip is released locking the clip into the base through the plicated tissue.

Another embodiment is shown in FIG. 42 as a U-shaped repair clip device that can be used with and without a pledget element 4220, shown in FIG. 42C. In the deformed delivery position 4210, FIG. 42A, the clip device can be delivered through the tissue using an introducer deployment mechanism (e.g., dual tapered needles) or tapering of the clip feet. In the undeformed position 4211, FIG. 42B, the clip device engages the tissue by deploying feet anchors 4213, as shown in FIG. 42F. Another embodiment of this includes the use of a backing or pledget component 4220 that is used as the locking base of the clip device. The clip device would be deployed as above, however, the locking base would be used to insure adequate locking of the tissue. The locking base would be supported by one jaw of the plication clamp while the deformed clip is advanced through the tissue and through openings in the locking base with the second jaw of the plication clamp. Once positioned, the clip is released locking the clip into the base through the plicated tissue.

An alternative reverse plication clip embodiment 4310 is shown in FIG. 43 where the centralized crossbar 4312 is made of a coiled shaped configuration that can act as a spring or the centralized crossbar could also be made of an elastic material. Deployment of the device would be similar to that described for FIG. 42, including the use with pledget. The embodiment in FIG. 43 enables expansion of the spring during position of the two locking legs 4311 such that when release the tissue is folded away from the coiled shaped crossbar. Additional embodiments of this device can include suture or polymer elements with distal tip collapsible polymer umbrella shaped elements. Upon deployment the collapsed polymer can be pushed through an introducer needle to the opposite side of the tissue layer to be plicated, introducer needle removed and polymer umbrella shape allowed to naturally expand. Both sides of this embodiment would be deployed simultaneously. Attachment of the suture or polymer connection elements to the polymer umbrella shape would be at the central position of the umbrella. The umbrella element would be flexible, but stiff enough and large enough that it will not pull back through the tissue easily. The suture or polymer connection will have a degree of elasticity to allow for temporary stress relief. Visually this may appear as a contact lens with a center tether. The advantage of such an embodiment include the ability to plicate soft tissues with materials and shapes that will be atraumatic to the tissues if failure occurs, as well as have elastic properties that allow for temporary stress relief.

Further embodiments would include the use of shape memory metals or shape memory polymer to deploy umbrella or various anchor shapes to plicate the tissue, achieving the same effect as described in the previous examples.

Figure 45A:
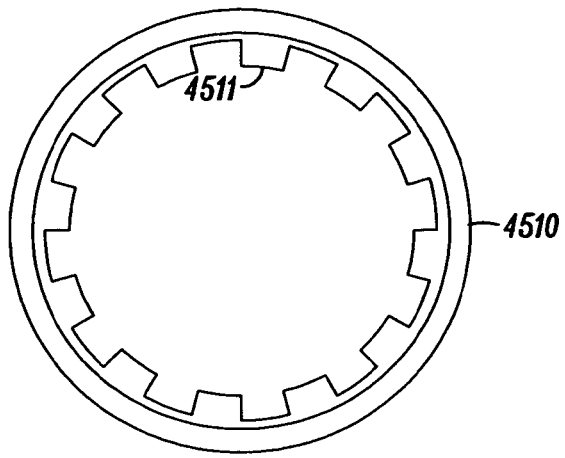
FIG. 45A to 45C show a perspective and top views of a single component plication device according to an exemplary embodiment of the present invention.
Figure 45B:
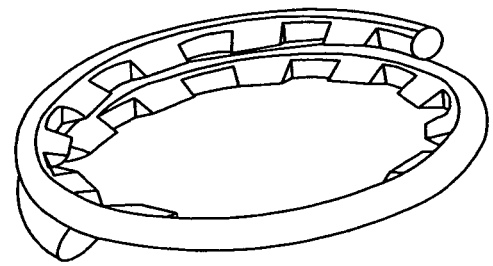
Figure 45C:
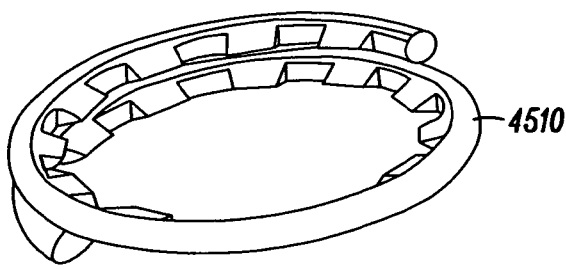
Figure 46A:
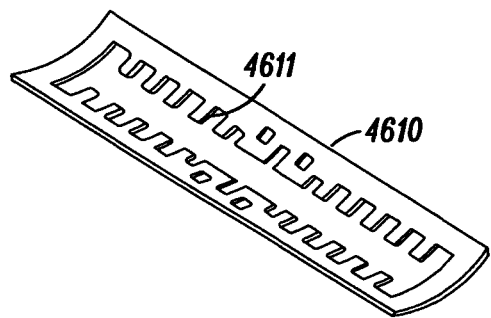
FIG. 46A to 46D show a perspective and side views of a single component plication device according to an exemplary embodiment of the present invention.
Figure 46B:
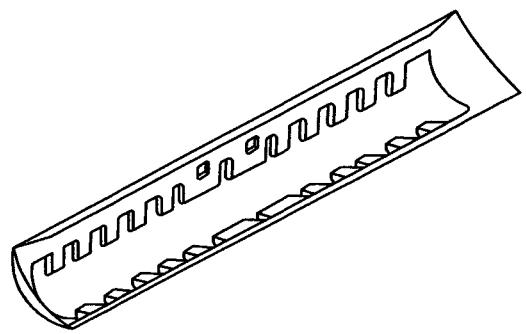
Figure 46C:
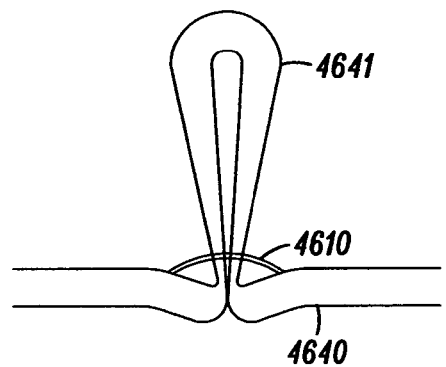
Figure 46D:
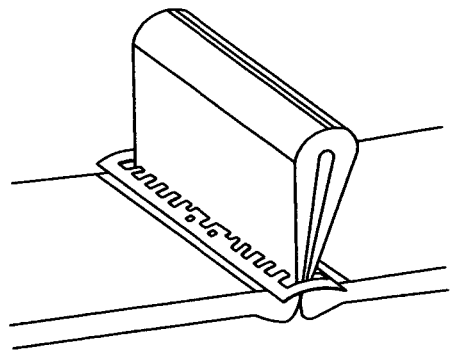

The exemplary embodiments shown in FIGS. 44 and 45 are single component plication clip devices 4410 and 4510. Both of these embodiments are circular rings with internal tooth elements 4411 and 4511 that are flat or can be layered in rows (as in FIG. 45) or concave inward. The primary purpose of the tooth elements 4411 and 4511 is to engage the tissue and prevent slipping of the tissue. Plication with these clips is performed as follows. A portion 4441 of tissue 4440 is grasped using the deployment device, the tissue is wrung in either a clockwise or counterclockwise direction for several rotations. As the tissue begins to bunch up, the circular plication element 4410 is advanced over the tissue 4441 down to the base of the plication region. The tissue 4441 is then released and allowed to expand. The expansion of this tissue locks the clip into place, thereby holding the tissue in a plicated state. The outer diameter of these rings can range from 2 to 20 mm and the inner diameter from 1 to 18 mm.

The embodiment depicted in FIG. 46 is a single component clip device 4610. This embodiment is a rectangular device that can be flat or curved in either the in-plane and out-of-plane directions, making tissue conformity better. A purpose of the tooth elements 4611 is to engage the tissue and prevent slipping of the tissue. Plication with these clips is performed as follows. A portion 4641 of tissue 4640 is engaged with the grasping mechanism of the deployment device 4610. Tissue 4641 is then drawn into the plication clip 4610 as the plication clip (deflected to expand the clip opening) is advanced over the tissue pleat to the base of the plication. The tissue and/or the plication clip are then released. The expansion of this tissue locks the clip into place, thereby holding the tissue in a plicated state. Moreover, the direction of the teeth can be oriented to allow for the tissue to easily pass through the device during plication. However, once deployed, the teeth 4611 will engage the tissue 4641 when tension in applied to pull the tissue out. As a result, the clip will maintain a lock on the tissue ensuring that the clip will be able to maintain the plication of the tissue. The outer dimensional ranges of the rectangular element are: length (2 to 40 mm) and width (1 to 10 mm). The inner dimensional ranges of the rectangular element are: length (1 to 38 mm) and width (0.5 to 9 mm).

Figure 47A:
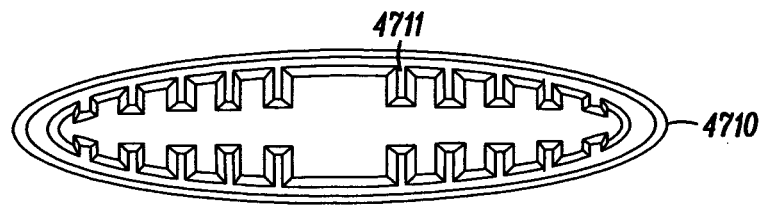
FIG. 47A to 47C show a perspective and top views of a single component plication device according to an exemplary embodiment of the present invention.
Figure 47B:
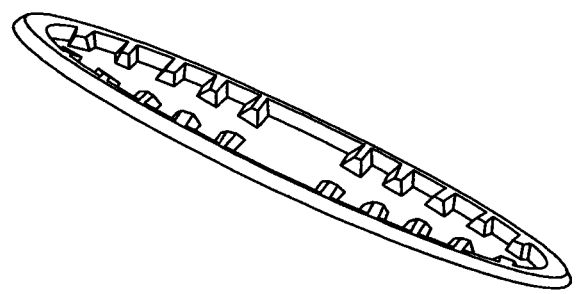
Figure 47C:
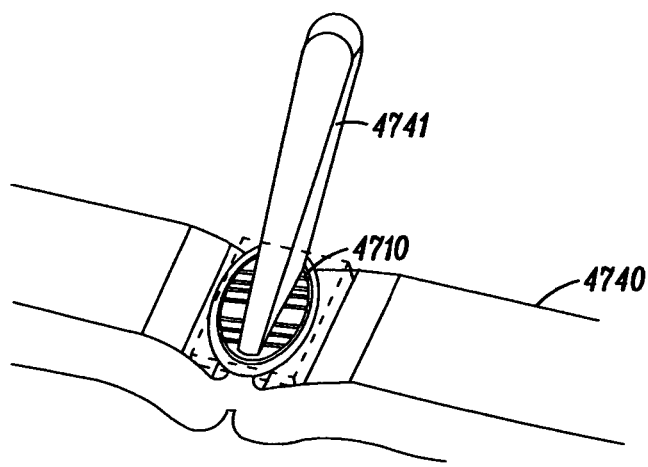

Variations of this embodiment are illustrated in FIGS. 47 to 51. FIG. 47 illustrates an oval shaped plication clip 4710 with a center region that can be used to pass the clip into position, pass the grasper element through the clip and draw the tissue pleat into the clip. This clip can be deformed to have curvature in the in-plane and out-of-plane directions to allow for conformity with the tissue pleat. The teeth 4711 in this embodiment and others described can have various shapes and patterns that allow for tissue engagement or added friction to the tissue. Moreover, the teeth 4711 can also consist of various other embodiments that allow for frictional as well as active engagement of the tissue pleat, for example bristles, flaps, or spikes. The size, width, pitch, depth of the teeth can be adjusted to optimize the holding strength and degree of engagement with the tissues.

Figure 48A:
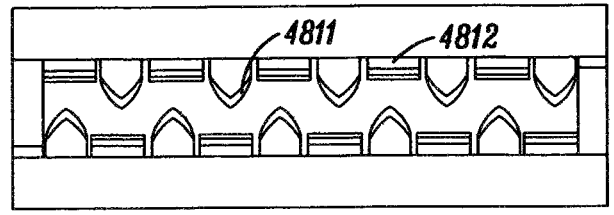
FIG. 48A to 48C show perspective, top, and side views of a single component plication device according to an exemplary embodiment of the present invention.
Figure 48B:
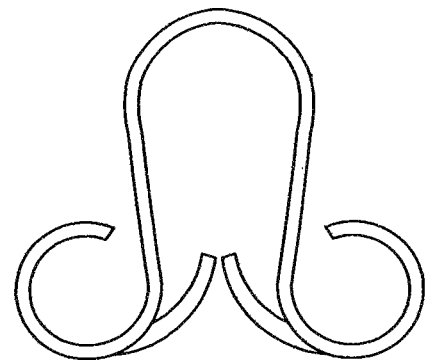
Figure 48C:
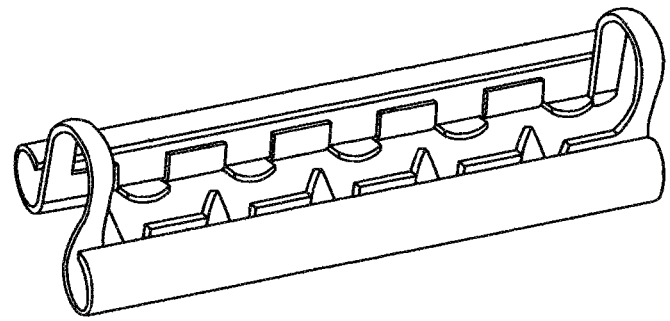
Figure 49A:
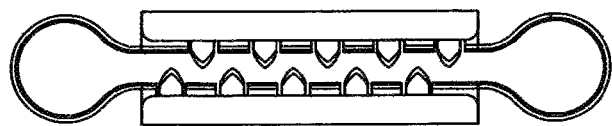
FIG. 49A to 49E show perspective, top, and side views of a single component plication device according to an exemplary embodiment of the present invention.
Figure 49B:
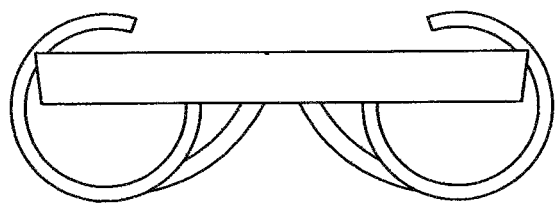
Figure 49C:
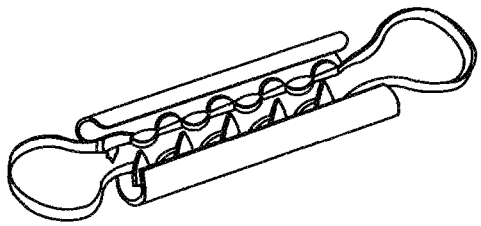
Figure 49D:
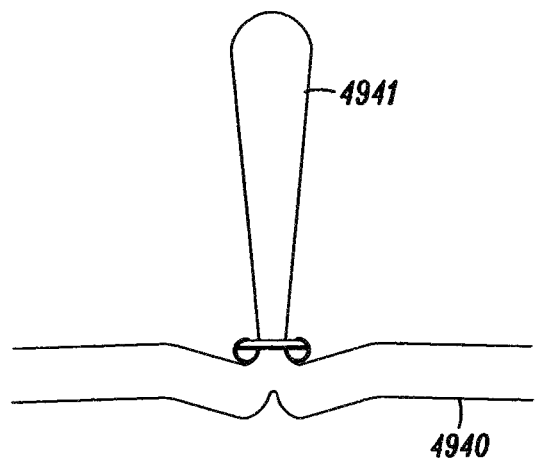
Figure 49E:
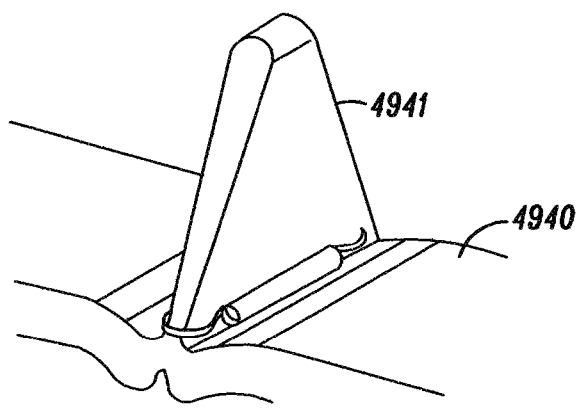
Figure 50A:
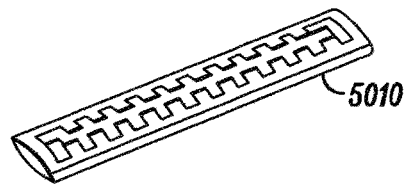
FIG. 50A to 50F show perspective, top, and side views of a single component plication device according to an exemplary embodiment of the present invention.
Figure 50B:
Figure 50C:
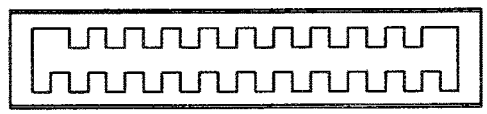
Figure 50D:
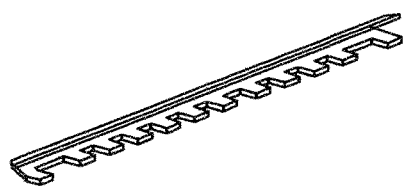
Figure 50E:
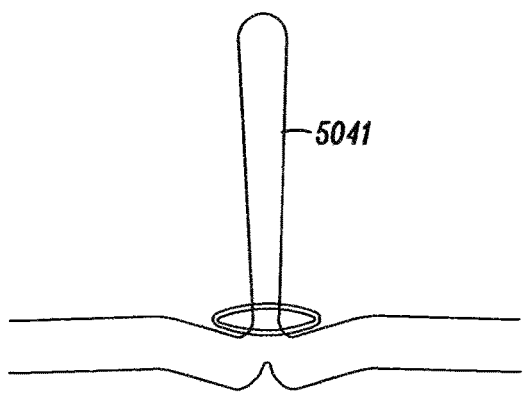
Figure 50F:
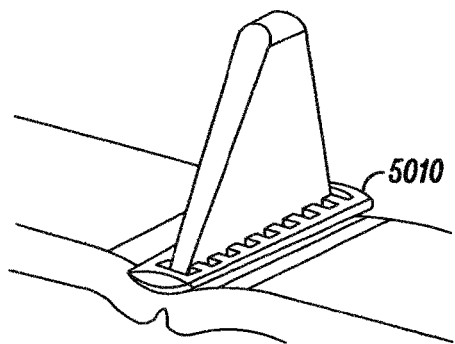

FIG. 48 shows an embodiment with variable teeth sizes and shapes 4811 and 4812. The general shape of the plication clip embodiment has curved edges to reduce the local stress on the tissue pleat caused by the clip. Moreover, the direction of the clip teeth are positioned to allow for engaging of the teeth into the tissue pleat if the pleat is tensioned (e.g., pulled) from the bottom, thus preventing release of the tissue pleat. The side rails of the embodiment are intended to allow for better conformity between the clip and the tissue pleat.

Figure 51A:
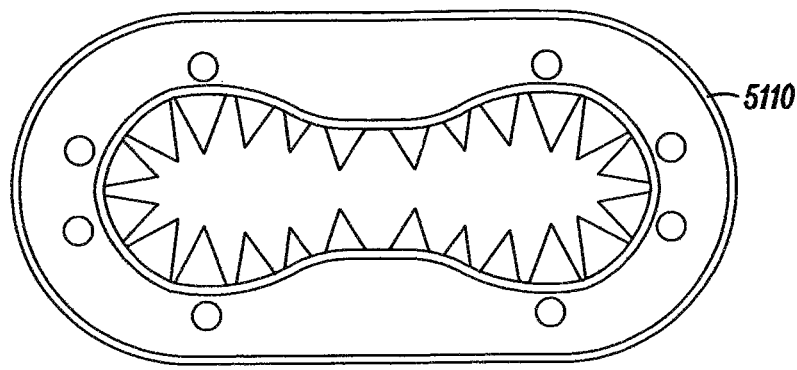
FIG. 51A to 51C show a perspective and top views of a single component plication device according to an exemplary embodiment of the present invention.
Figure 51B:
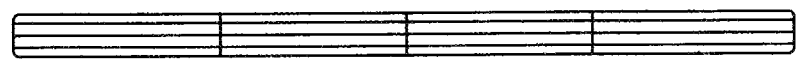
Figure 51C:
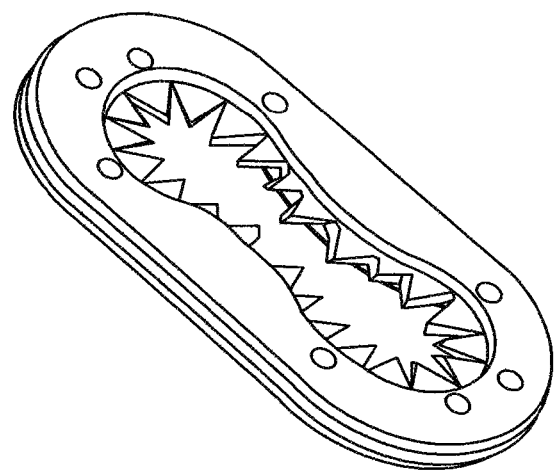

FIG. 49 shows a variation of the embodiment shown in FIG. 48 where the rails are positioned in the axis parallel to the tissue plane. The embodiments shown in FIGS. 50 and 51 are additional variations in embodiments for methods to engage the tissue with the locking clips. Benefits of all of these clip designs includes irritation of the synovium which will elicit a favorable biologic healing response. The design of the clip teeth can be optimized to take full advantage of this characteristic. Furthermore, each of these above designs can be manufactured from various material combinations or single materials (e.g., metals, polymers, shape memory alloys, etc.).

Figure 52A:
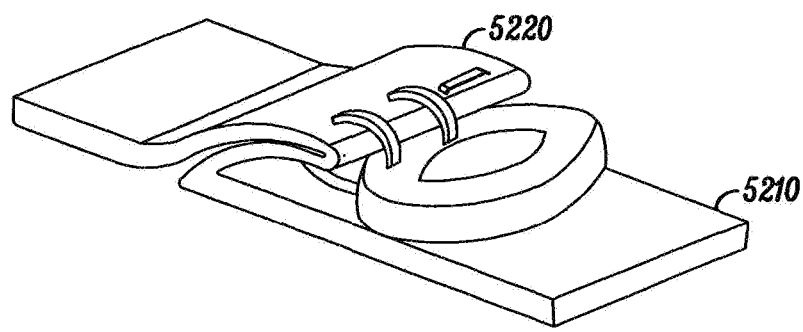
FIGS. 52A to 52C show a plication of the capsule to the labrum using device clip devices according to an exemplary embodiment of the present invention.
Figure 52B:
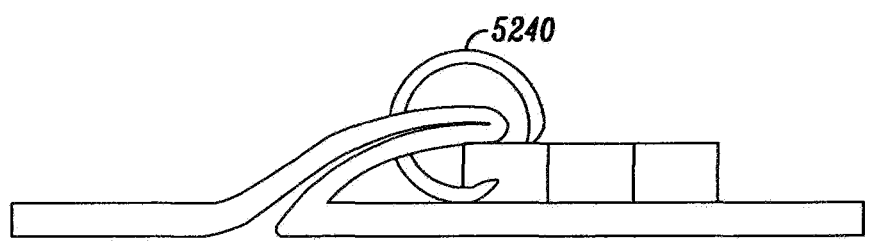
Figure 52C:
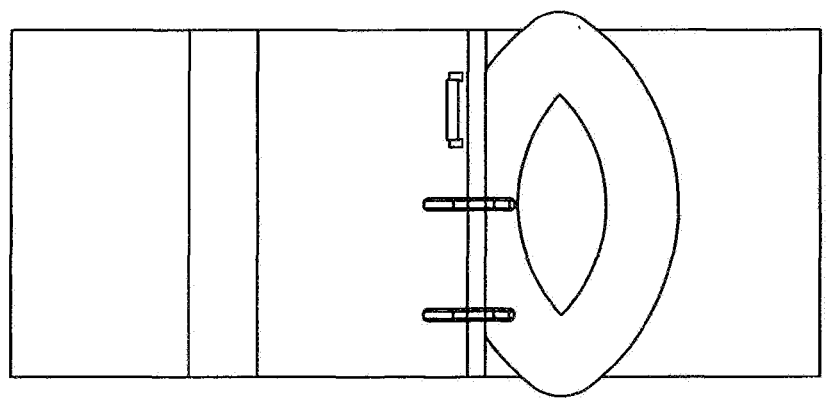

The embodiment shown in FIG. 52 is an example of using the plication clip devices for the treatment of capsule to labrum plication. Shown are top, side, and profile views of the plicated capsule to labrum tissues. The embodiments shown in the figure include the use of U-shaped plication clips 5240 in two orientations. Various other plication clip design described above can be used to achieve similar plication as shown. Primary factors that are considered for embodiments for this plication include the potential for abrasion or interaction with the articular surfaces as well as potential for loosening of the device. The position of the device relative to the glenoid articulating surface will be sufficiently lateral as not to interact. Furthermore, the embodiment of the plication clip will be of small enough as not to protrude into the glenoid articulating space. Additionally, the material used for the plication clip in this application will have ideal characteristics relative to stiffness and strength.

In operation, the plication clamp is used to grasp the capsule and pull a fold of capsular tissue into the clamp jaws. The clamp jaws are then used to position the plication clip with one jaw passing through the capsular fold and the other jaw passing through the labrum and then the capsular fold. It should be noted that the capsule to labrum plication can be executed as a separate operation after placating the capsule (e.g., attached the already plicated capsule distal end to the labrum), a simultaneous step of placating the capsule directly to the labrum (as shown in FIG. 52), or a simultaneous reverse plication where a region of the capsule is pulled into direct contact with the labrum pushing the fold away from the jaws of the clamp.

Various appropriate materials may be used to construct the elements or various parts of the elements that comprise the exemplary embodiments shown and described in this disclosure. For example, the locking base and arms of clips, spikes, needle, grasper, or deployment device components that require the ability to have elastic properties relative to being able to be deformed and deployed (returned to intended shape) using arthroscopic devices can be fabricated from various materials, including, but not limited to shape memory alloys (e.g., nickel titanium (Nitinol), shape memory polymers, polymers (e.g., PTFE, polyurethane, urethane, silicone, polyimide, polypropylene, Polylactic Acid, Polyglycolic Acid, or other thermoset or thermoplastic, or elastomeric materials) and metals (e.g., titanium, CoCrMo, stainless steel, nickel titanium, etc).

In some embodiments, the device clips or sutures may be resorbable, in other embodiments, the device components will have limited or no resorption characteristics. The clips components described in this disclosure can be made in part or solely of one material. Alternatively, the structures of the clips can be composed of metal and/or polymer components fabricated into composite devices. For example, low surface area and thin metal or metal alloy components that define the puncturing and/or locking components of the cups can be insert molded with a polymer (e.g., polypropylene) to produce a composite device that has very little radiopacity but exhibits excellent puncturing and locking characteristics. Some embodiments may include parts that are resorbable and some that are not.

Fabrication of these clip components can be performed using techniques familiar with manufacturing methods by those skilled in the art of metals, polymers, shape memory alloys, shape memory polymers, or composite materials. Sample techniques include, but are not limited to, extrusion, casting, press-forging, rolling, or pressing methods for the fabrication of parts for the above materials. In specific instances, the use of techniques related to modification of polymer chemistry to adjust the shape memory characteristics related to thermal conditions and elastic properties of the polymer will be utilized. With respect to shape memory metal materials, one skilled in the art will utilize the thermal characteristics of the specified composition to fabricate components with the geometry and features required for the device component. Proper thermal forming and quenching is required to process the material and is generally known to one skilled in the art of using, processing, and fabricating components out of shape memory materials.

In some embodiments several components may require parts using standard machining techniques typically known to one skilled in the art of machining. For example, use of CNC, EDM, laser cutting, water jet cutting, polishing methods, and other machining techniques. Several embodiments may also require bonding or welding of components and include adhesives, laser welding, soldering, or other means of attachment.

Clip components that include spikes or needles may be fabricated from any stock materials typically known to one skilled in the art of medical device manufacturing. Attachment of suture or other clip materials to these embodiments can be performed by tying, welding, bonding, clamping, embedding, or use of other such means for securing the spike or needle to the suture or other clip materials. In some embodiments, these spikes or needles can be mechanically polished or electropolished to produce smooth surfaces.

Various embodiments of the clip components described can be coated with or encapsulated with a covering of a polymer material that can allow for the use of anti-proliferative, antibiotic, angiogenic, growth factors, anti-cancer, or other pharmacological substances that may provide a benefit related to inhibiting or promoting biological proliferation. These substances would be loaded into the encapsulating coatings and be allowed to elute into the surrounding matrix, tissues, or space that it sits. The time course of delivery can be tailored to the intended application by varying the polymer or the characteristics of the coating. Such coatings with pharmacological substances can act as anti-proliferative treatments or can aid in the healing response of the tissue being treated. Furthermore, these coatings can act to reduce the local coagulation or hyperplastic response near the chip.

Various examples of surgical procedures using the devices, systems and methods of the present invention will be described in the non-limiting examples provided below.

In each example described, one or more of the various embodiments shown in FIGS. 2-52 may be used.

Example A

Arthroscopic Repair of Bankart Lesion with Arthroscopic Suture Plication of Associated Anterior Capsular Laxity Following examination under anesthesia and standard surgical prepping and draping, standard anterior and posterior glenohumeral arthroscopy portal are established. The patient may be positioned either in the lateral decubitus position or in a beach chair position. Following completion of diagnostic arthroscopy, attention is first focused on repair of the Bankart lesion. After the Bankart repair has been performed, residual anterior capsular laxity is assessed. The surgeon subsequently places the humerus in the desired position (in terms of external rotation and abduction; this will vary according to patient demand and individual surgeon preference). With the shoulder placed in the desired position, capsular redundancy is addressed via performing a suture plication. The capsular plication deployment device is introduced through a standard anterosuperior portal. Capsular grasper is deployed to create a capsular pleat delivering the capsular pleat into the jaws of the clip passing device. The clip device is subsequently deployed. Typically, two to four separate clip implant devices will be placed in a sequential posteroinferior to anterosuperior direction along the capsule. Additional clips may be placed to ensure that capsular redundancy has been adequately rectified. The amount of capsule delivery into the jaws of the clip passing device (and hence, the amount of capsular tightening) will vary according to surgeon preference and the amount of capsular laxity and patient demand. Of note, the Bankart repair must be conducted first in order to adequately assess the amount of residual amount of capsular laxity and determine the ideal required amount of capsular tightening. One of the advantages of exemplary devices according to the present invention is their ability to tighten the capsule a variable amount based upon individual situations. Following completion of placement of the desired plications, the arthroscopic probe is introduced and each of the plications is individually probed to confirm that the clip devices have been deployed in a stable fashion. The shoulder is place through a trial range of motion while the tensioned portion of the capsule is visualized to, once again, confirm that adequate fixation of each of the capsular plications has been achieved.

Example B

Capsular Laxity without an Associated Bankart Lesion (e.g., Anterior Unidirectional Atraumatic Instability)

Following examination under anesthesia, standard anterior and posterior glenohumeral arthroscopic portals are established. A thorough diagnostic glenohumeral arthroscopy is performed with specific attention to determining the extent and distribution of capsular laxity. With the shoulder positioned in the desired amount of abduction and external rotation, the anterior capsule is tensioned via placement of anterior capsular plications in a posteroinferior to anterosuperior sequence via the anterosuperior portal. The sequence of placement of successive plication devices in a posteroinferior to anterosuperior direction is determined by virtue of the fact that if the anterosuperior capsule is tensioned first then placement of the capsular plication deployment device more inferiorly and posteriorly will be more difficult. However, tensioning the axillary pouch (posteroinferior section) first does not limit access further anteriorly and superiorly on the inferior glenohumeral ligament. Following completion of placement of the desired plications, the arthroscopic probe is introduced and each of the plications is individually probed to confirm that the exemplary clip devices have been deployed in a stable fashion. The shoulder is placed through a trial range of motion while the tensioned portion of the capsule is visualized to, once again, confirm that adequate fixation that each of the capsular plications has been achieved.

Example C

Multidirectional Instability (MDI)

Following examination under anesthesia, standard anterosuperior and posterior glenohumeral arthroscopic portals are established and a through diagnostic arthroscopy is performed. The redundant posterior capsule and posteroinferior capsule is tightened first. This is accomplished via visualization through an accessory anterior portal. The capsular plication deployment device is introduced through the standard anterosuperior portal. The posterior capsule is visualized via placement of the arthroscope through the accessory anterior portal. Posterior capsular redundancy is reduced via placement of successive capsular plications posteriorly (in an inferior to superior sequence). The arthroscope is subsequently reintroduced through the standard posterior glenohumeral viewing portal and the standard anterosuperior portal is utilized to perform the capsular plications. The inferior and anterior glenohumeral capsule is tensioned via placement of sequentially clip devices according to exemplary embodiments of the present invention in an inferior to superior direction. Following completion of placement of the desired plications, the arthroscopic probe is introduced and each of the plications is individually probed to confirm that the clip devices have been deployed in a stable fashion. The shoulder is place through a trial range o motion while the tensioned portion of the capsule is visualized to, once again, confirm that adequate fixation that each of the capsular plications has been achieved.

Example D

Lung Volume Reduction Surgery (LVRS)

Figure 53:
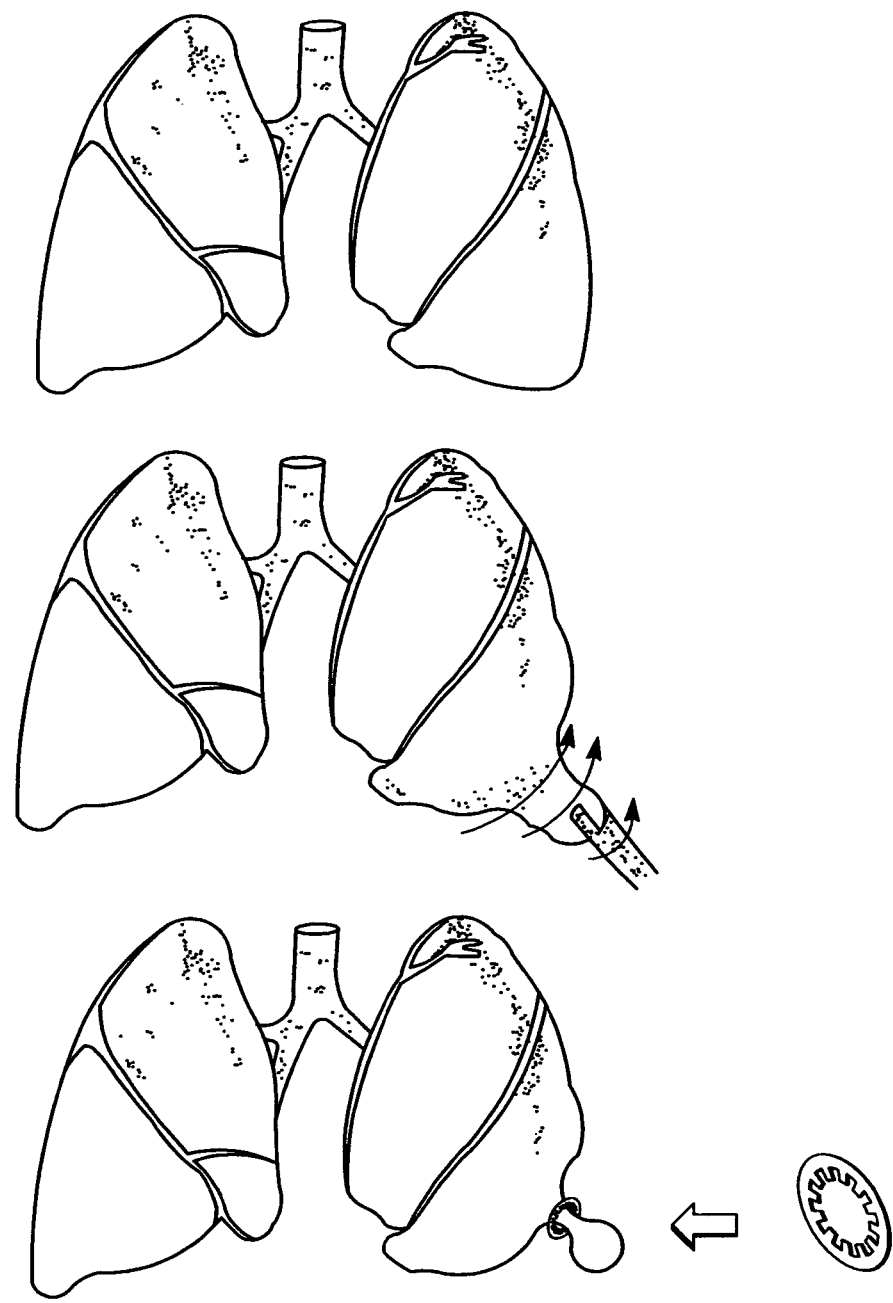
FIG. 53 shows lung volume reduction application with suture or clip tissue fixation according to an exemplary embodiment of the present invention.
Figure 54A:
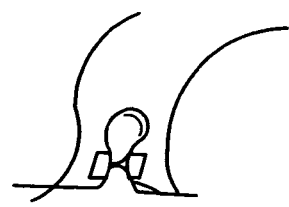
FIG. 54 shows a laparoscopic gastric fundoplication with laparoscopic suture or clip tissue fixation according to an exemplary embodiment of the present invention.
Figure 54B:
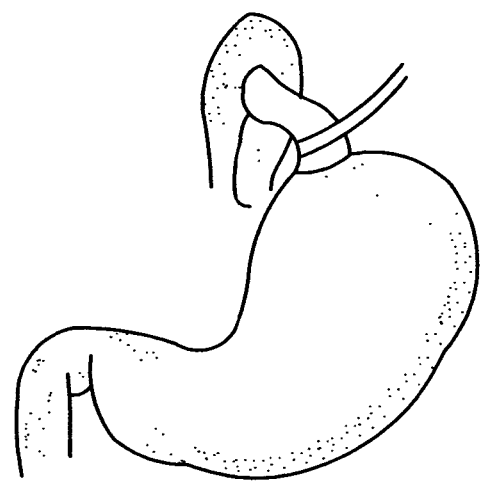
Figure 54C:
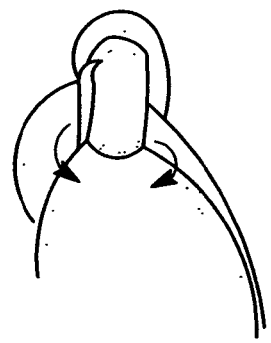
Figure 54D:
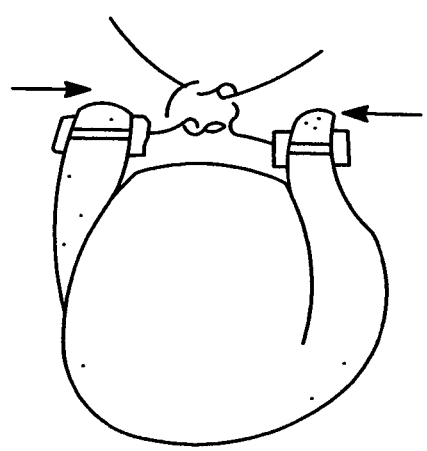
Figure 54E:
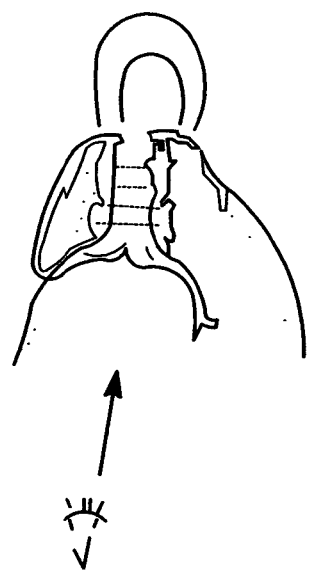

Preoperative imaging (e.g., radiographs, computed tomography) is performed to identify the segments of the lung requiring volume reduction. Following anesthesia induction, the patient is position in the lateral decubitus position to allow placement of thorascope as well as another access port for the plication delivery device positioning. The lung is collapsed using standard techniques. Using the plication delivery device grasping mechanism, the region of lung tissue to be reduced can be retracted into the device. Care is taken in the placement of the access port for the plication device to insure that when the device is engaged with the lung tissue that the tissue is not deformed or stressed to a point where excessive trauma occurs. The identified lung tissue section to be reduced is grasped by the device jaws. Axial rotation of the device jaw will result in wringing of the lung tissue, FIG. 53. The wringing of the lung tissue will draw tissue surrounding the point of grasping to be circumferentially pulled into the center. Once sufficient lung tissue is determined to be reduced, the plication clip is advanced into position down the shaft of the delivery device. Advancement of the plication clip is continued until it is positioned at the base of the wrung region, such as shown in FIG. 53. Typical advancement of the plication clip will range from 0.5 to 25.4 centimeters from the tip to the base of the wrung lung tissue. The plication is examined to insure proper alignment and deployment. The result of this plication will result in a reduced volume capacity of the lung, minimizing the effects of the diseased section of the lung. Once the plication clip is fully deployed, the grasper is released and plication device withdrawn. Additional regions of plication can also be addressed at the same time. The use of these plication clips should not result in the generation of air leaks of any significance. Furthermore, upon reinflation of the lung, evaluation of whether or not sufficient lung volume reduction is achieved can be evaluated. If necessary, standard chest tubes can be positioned anteriorly and posteriorly to the apex of the lung and suction initiated to remove excess fluid from the pleural cavity. Multiple plication clips are expected to be used to adequately reduce the lung volume.

Figure 55:
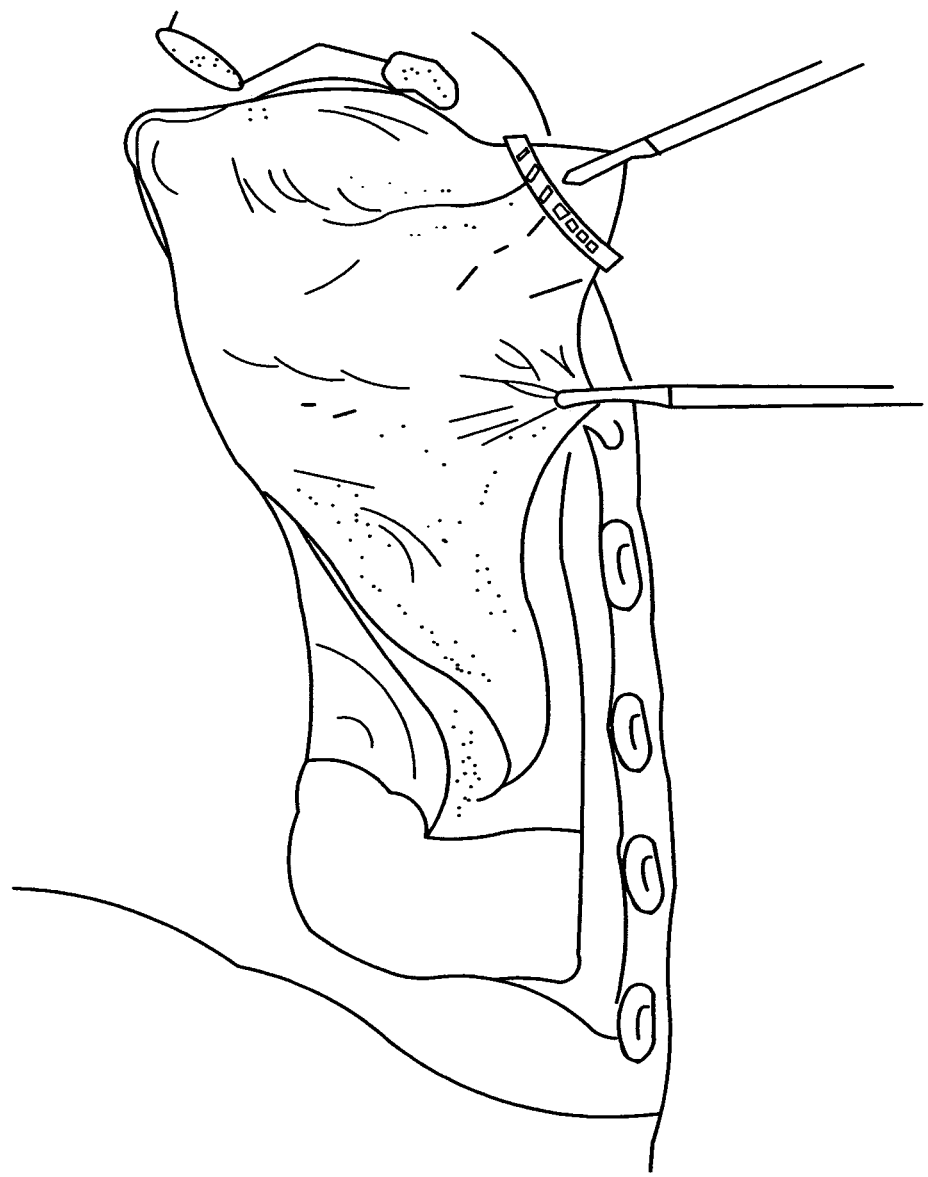
FIG. 55 shows a thorascopic lung reduction procedure with thorascopic suture or clip tissue fixation according to an exemplary embodiment of the present invention.

Variations in the plication clip delivery may not require wringing of the tissue but rather only grasping of the tissue and then advancement of the clip over the tissue, as shown in the lung reduction procedure shown in FIG. 55. In these types of embodiments, the same range of advancement can be achieved (0.5 to 25.4 centimeters). Similarly, multiple devices can be deployed until adequate lung volume reduction can be achieved.

Example E

Laparoscopic Gastric Fundoplication with Laparoscopic Suture or Clip Tissue Fixation Following anesthesia induction, the patient is positioned, prepped and draped in the standard fashion for an upper abdominal laparoscopic procedure. Using standard laparoscopic technique, a trocar is introduced through the abdominal wall and a laparoscope is advanced into the abdomen to provide visualization. Additional trocars (3-4) are inserted to accommodate required instrumentation. Under direct laparoscopic visualization, the surgeon elevates the liver to expose the junction between the stomach and the esophagus. Using sharp and blunt dissection, the hiatal hernia is reduced by freeing the esophagus and the stomach of surrounding soft tissue connections around the diaphragmatic hiatus and pulling the stomach and about 5 or 6 cm of the esophagus down into the abdomen. A space is created behind the esophagus and the fundus of the stomach, exposing the diaphragmatic hiatus. The size of the hiatus (defined by the arches of the left and right crural fiber bands) is reduced by approximating the muscles of the left and right crura behind the esophagus. The laparoscopic tissue fixation device is inserted through a trocar and advanced to the hiatus. Using a laparoscopic forcep through another trocar, the crural fibers are pulled so they are adjacent. The tissue grasper is deployed from the fixation device, and the adjacent fiber bands grasped together and pulled between the jaws of the fixation device. The fixation device is activated, securing the crural fibers with a suture, clip or other point fixation device. The process is repeated, until the opening of the hiatus is adequately reduced, usually requiring two or three adjacent fixations, as shown in FIG. 54.

Using sharp dissection, the fundus of the stomach is freed of its connections, such as the short gastric vessels to the spleen and small ligaments connecting it to the left diaphragm. This mobilization creates a window behind the esophagus. The redundant portion of the stomach fundus on the left side is then pulled behind the esophagus to the right side and then around the front of the esophagus, forming a wrap, as shown in FIG. 54. Depending on the type of procedure, the wrap may be secured partially or completely around the esophagus. For a partial wrap, laparoscopic forceps are used to position the ends of the wrap next to the anterior wall of the esophagus, and prepared for the fixation device. The approximated tissues are grasped together using the tissue grasper, and the tissues pulled into the jaws of the device. The fixation device is activated, securing the crural fibers with a suture, clip or other point fixation device. The process is repeated until the edge of the wrap is secured, usually requiring 2-4 fixations. The fixation is repeated in a similar fashion for the other edge of the wrap. For a complete wrap, laparoscopic forceps are used to position the ends of the wrap next to each other in front of the anterior wall of the esophagus. The wrap is prepared for fixation by grasping both left and right edges of the wrap with a pleat of anterior esophageal wall sandwiched in between. The approximated tissues are grasped together using the tissue grasper, and the tissues pulled into the jaws of the device. The fixation device is activated, securing the wrap and esophageal tissues with a suture, clip or other point fixation device. The process is repeated until the edge of the wrap is secured, usually requiring 2-4 fixations.

Example F

Laparoscopic Hernia Repair with Laparoscopic Suture or Clip Tissue Fixation

Following anesthesia induction, the patient is positioned, prepped and draped in the standard fashion for an abdominal laparoscopic procedure. Using standard laparoscopic technique, a trocar is introduced through the abdominal wall and a laparoscope is advanced into the abdomen to provide visualization. Additional trocars (2-3) are inserted to accommodate required instrumentation. Under direct laparoscopic visualization, the hernia contents are reduced by taking down the adhesions to the abdominal wall and within the hernia sack itself. Once the abdominal wall is free, a tightly rolled prosthetic patch or mesh is inserted through one of the ports into the abdomen, where it is unrolled and positioned under the defect. The patch may be placed on the peritoneum or the peritoneum may be opened and the patch placed between the peritoneum and abdominal fascia. Several sutures may be used to anchor the patch in place to the abdominal fascia. The laparoscopic tissue fixation device is inserted through a trocar and advanced to the patch. Using a laparoscopic forcep through another trocar, the edge of the patch and peritoneum or fascia are pulled so they are adjacent. The tissue grasper is deployed from the fixation device, and the edge of the patch and peritoneum or fascia are grasped together and pulled between the jaws of the fixation device. The fixation device is activated, securing the patch to the peritoneum or fascia with a suture, clip or other point fixation device. The process is repeated, until the edges of the entire patch are secured to the peritoneum or fascia at 1 cm intervals to prevent internal hernia. The patch size is usually 8 to 10 cm larger than the defect, in effect reconstructing the abdominal wall. If the peritoneum was opened, this is now closed over the patch.

Example G

Thoracoscopic Mitral Valve Repair with Thoracoscopic Suture or Clip Tissue Fixation Following anesthesia induction, the patient is positioned, prepped and draped in the standard fashion for a right chest thoracoscopic procedure. Using standard thoracoscopic technique, a trocar is introduced through the thoracic wall and a thoracoscope is advanced into the right pleural space to provide visualization. Additional trocars (2-4) are inserted to accommodate required instrumentation. $CO_2$ insufflation may be used to displace the left lung and enhance visualization. A small intercostal incision may be used as a working portal in addition to the trocar ports.

Mitral valve reconstruction may be performed alone or as a part of another thoracoscopic cardiac procedure. Under direct thoracoscopic visualization, the pericardium is opened anterior to and parallel to the right phrenic nerve using scissors. The patient is systemically anticoagulated and cardiopulmonary bypass is instituted by cannulation by femoral approach or by direct cannulation through the thoracic incisions. The heart is arrested and vented.

Figure 56:
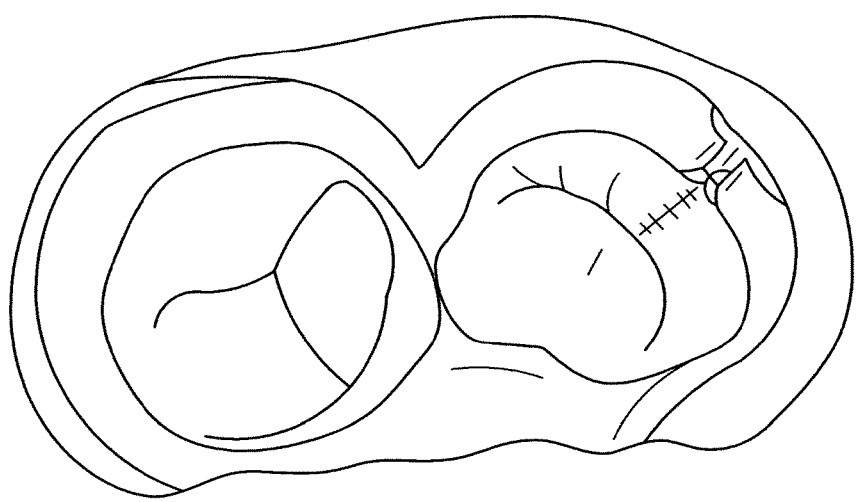
FIG. 56 shows a thorascopic mitral valve repair with thorascopic suture or clip tissue fixation according to an exemplary embodiment of the present invention.

Using sharp dissection, the left atrium is entered by incision either anterior to the right pulmonary veins or through exposure through the atrial septum. The mitral valve is exposed with retractors and inspected. Leaflet resection and repair may be performed as indicated by the underlying pathology. For example, isolated posterior leaflet cusp prolapse may be treated by a triangular or quadrangular resection. After resection of the flail cusp using scissors, the annulus diameter is reduced adjacent to the defect by plicating the annulus. Using a thoracoscopic forcep, the annular tissue is grasped and elevated. The tissue grasper is deployed from the fixation device, and the elevated annular tissue is grasped and pulled between the jaws of the fixation device. The fixation device is activated, plicating the annulus together with a suture, clip or other point fixation device. One or more adjacent plication points may be required to create sufficient annular reduction. Using a forcep, the cut edges of the valve leaflet are approximated. The tissue grasper is deployed from the fixation device, and the adjacent edges of the valve is grasped and pulled between the jaws of the fixation device. The fixation device is activated, securing the edges of the leaflet together with a suture, clip or other point fixation device. Two or more adjacent fixation points may be required to create a continuous line of fixation, FIG. 56.

The valve repair is then reinforced with a partial or complete circumferential annuloplasty ring. A forcep is used to bring the ring to the annulus adjacent to one of the commissures, and the combination is gripped by the tissue grasper in the fixation device and pulled between the jaws of the fixation device. The fixation device is activated, securing the ring to the annulus with a suture, clip or other point fixation device. This is repeated at the other commissure. Using forceps to adjust the relative spacing, additional adjacent fixation points are serially fashioned to create a continuous line of attachment between the ring and the annulus. The valve is then tested to assure competency. The atriotomy edges are approximated, then grasped and secured using the fixation device. This is repeated at adjacent points along the edges until the incision satisfactorily closed. The heart is de-aired, reperfused, normal rhythm restored, and cardiopulmonary bypass terminated.

Example H

Figure 57A:
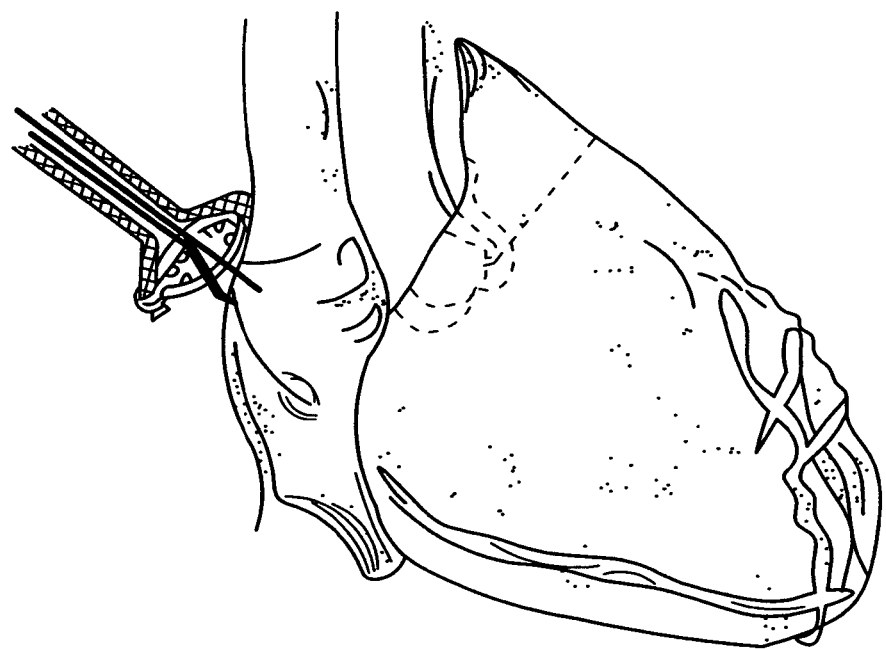
FIGS. 57A and 57B show an exemplary atrial appendage isolation (or removal) procedure on the heart according to an embodiment of the present invention.
Figure 57B:
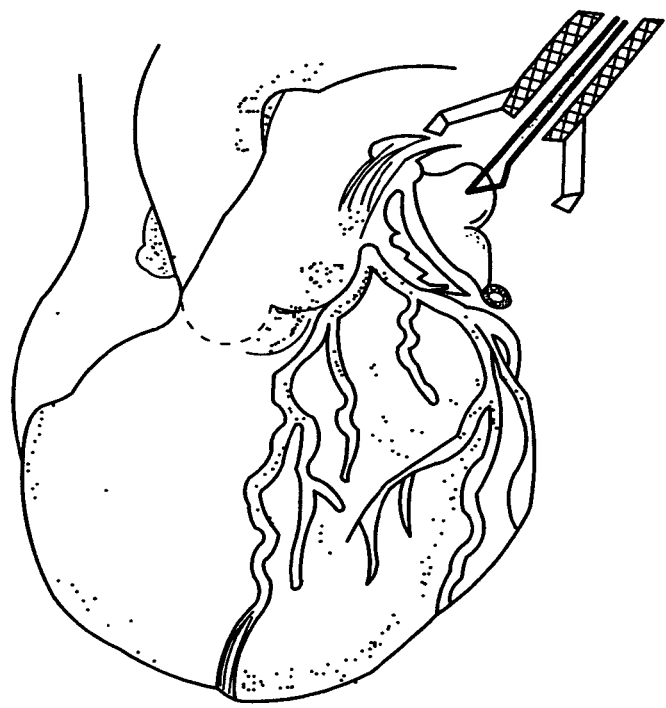

Thoracoscopic Left Atrial Appendage Ligation with Thoracoscopic Suture or Clip Tissue Fixation Following anesthesia induction, the patient is positioned, prepped and draped in the standard fashion for a left chest thoracoscopic procedure. Using standard thoracoscopic technique, a trocar is introduced through the thoracic wall and a thoracoscope is advanced into the left pleural space to provide visualization. Additional trocars (2-4) are inserted to accommodate required instrumentation. $CO_2$ insufflation may be used to displace the left lung and enhance visualization. Left atrial appendage ligation may be performed alone or as a part of another thoracoscopic procedure. Under direct thoracoscopic visualization, the pericardium is opened anterior to and parallel to the left phrenic nerve using scissors, FIGS. 57A and 57B. The appendage of the left atrium is identified, and mobilized using sharp and/or blunt dissection. Using a thoracoscopic forcep introduced through a trocar, the tip of the appendage is gently manipulated so that the base of the appendage can be visually inspected to determine the location for the ligation line. The tissue grasper is deployed from the fixation device, and the edge of the atrial appendage is grasped and pulled between the jaws of the fixation device. The fixation device is activated, securing walls of the appendage together with a suture, clip or other point fixation device. One or more adjacent fixation points may be required to create a continuous line of ligation. The fixation device jaws are opened, the tissue released, the device is repositioned and the process repeated until the walls of the appendage are completely secured from edge-to-edge along the planned line of ligation. The appendage ligation line is inspected for hemostasis, and a soft drain may be brought through an opening in the chest wall and directed into the pericardial space.

Using a thoracoscopic forcep, the edges of the opening in the pericardium are brought into approximation. The tissue grasper is deployed from the fixation device, and the pericardial edges are grasped and pulled between the jaws of the fixation device. The fixation device is activated, securing the pericardial edges together with a suture, clip or other point fixation device. One or more adjacent fixation points may be required to adequately re-approximate the pericardium. A drain may be brought through an opening in the chest wall and directed into a dependent area of the thoracic space for postoperative pleural drainage.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. In particular, the many examples shown above that relate to the shoulder capsule and plication are not limited to such, and may be applied to any tissue or tissue structure as well as any type of repair performed thereon. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

We claim:

1. A system for repair of soft tissue, the system comprising:
   a first jaw element for securing and moving a portion of soft tissue that is to be repaired, the first jaw element having an undeployed retracted state and a deployed extended state;
   a second jaw element comprising a jaw portion and a spike portion affixed to the jaw portion, the spike portion extending from the jaw portion such that when the jaw portion clamps down on the portion of soft tissue, the spike portion penetrates the portion of soft tissue to retain the portion of soft tissue for the soft tissue repair;
   at least one fixation component comprising a suture or clip structure, where the at least one fixation component is pre-loaded into a portion of the second element and configured to penetrate the portion of soft tissue with the spike portion, where the at least one fixation component is removably located within the second element to remain within the portion of soft tissue;
   a third element comprising a trigger for actuating the first jaw element and the second element in turn for performing the soft tissue repair;
   wherein the first jaw element is disposed within the jaw portion of the second element when it is in its undeployed retracted state, and is disposed outside of the jaw portion of the second element when it is in its deployed extended state; and
   upon opening of the jaw portion of the second element, the second element, with the spike portion remaining affixed to the jaw portion, disengages from the soft tissue, leaving the at least one fixation component secured to the soft tissue and detached from the second element and the spike portion.

2. The system as recited in claim 1, wherein the first jaw element, in its deployed state, captures the portion of soft tissue and then is retracted to its undeployed state to bring the portion of soft tissue to a location within the jaw portion of the second element.

3. The system as recited in claim 1, wherein the portion of soft tissue comprises an interior concave surface of a capsular body, and the soft tissue repair comprises plication.

4. The system as recited in claim 1, and further comprising a neuro-stimulator for stimulating nerves near the portion of soft tissue, so that a user is signaled of the presence of a nearby nerve.

5. The system as recited in claim 4, wherein said neuro-stimulator comprises a probe element which comprises a portion of said first jaw element.

6. The system as recited in claim 1, wherein at least one of the first and second elements includes abrading tools for abrading the portion of soft tissue in order to irritate the tissue and aid in natural tissue repair.

7. The system as recited in claim 1, wherein the fixation component comprises a suture to repair the portion of soft tissue.

8. The system as recited in claim 7, wherein the suture is configured to be automatically released from the second element after the tissue is repaired and the jaw portion of the second element are opened.

9. The system as recited in claim 1, wherein the fixation component comprises a tissue locking mechanism to repair the portion of soft tissue.

10. The system as recited in claim 9, wherein the tissue locking mechanism comprises: an anchor element having a shaft with two penetrating ends for penetrating the soft tissue, wherein each penetrating end has a movable anchor stop which permits the end to penetrate tissue initially, and then turns to lock the anchor stop on the side of the portion of soft tissue that is opposite to the side of the shaft.

* * * * *